United States Patent
Velasquez et al.

(10) Patent No.: US 10,676,748 B2
(45) Date of Patent: *Jun. 9, 2020

(54) APTAMERS FOR CONSUMER PRODUCT COMPOSITIONS

(71) Applicant: The Procter & Gamble Company, Cincinnati, OH (US)

(72) Inventors: Juan Esteban Velasquez, Cincinnati, OH (US); Amy Violet Trejo, Oregonia, OH (US); Paul Albert Sagel, Maineville, OH (US); Gregory Allen Penner, Lond (CA)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/059,396

(22) Filed: Aug. 9, 2018

(65) Prior Publication Data

US 2019/0048348 A1    Feb. 14, 2019

Related U.S. Application Data

(60) Provisional application No. 62/542,936, filed on Aug. 9, 2017.

(51) Int. Cl.
| | | |
|---|---|---|
| *C12N 15/115* | (2010.01) | |
| *A61K 8/00* | (2006.01) | |
| *A61K 9/51* | (2006.01) | |
| *A61K 31/7125* | (2006.01) | |
| *A61Q 11/00* | (2006.01) | |
| *C11D 1/00* | (2006.01) | |
| *A61K 8/60* | (2006.01) | |
| *C11D 1/90* | (2006.01) | |
| *A61K 9/16* | (2006.01) | |
| *A61K 31/4706* | (2006.01) | |
| *A61K 31/522* | (2006.01) | |
| *A61K 47/14* | (2017.01) | |
| *A61K 47/26* | (2006.01) | |
| *A61K 47/54* | (2017.01) | |
| *B82Y 5/00* | (2011.01) | |

(52) U.S. Cl.
CPC ............ *C12N 15/115* (2013.01); *A61K 8/606* (2013.01); *A61K 9/1676* (2013.01); *A61K 9/51* (2013.01); *A61K 31/4706* (2013.01); *A61K 31/522* (2013.01); *A61K 31/7125* (2013.01); *A61K 47/14* (2013.01); *A61K 47/26* (2013.01); *A61Q 11/00* (2013.01); *C11D 1/90* (2013.01); *A61K 47/549* (2017.08); *B82Y 5/00* (2013.01); *C12N 2310/16* (2013.01); *C12N 2310/313* (2013.01); *C12N 2310/314* (2013.01); *C12N 2310/315* (2013.01); *C12N 2310/3125* (2013.01); *C12N 2310/321* (2013.01); *C12N 2310/3341* (2013.01)

(58) Field of Classification Search
None
See application file for complete search history.

(56) References Cited

U.S. PATENT DOCUMENTS

| | | | | |
|---|---|---|---|---|
| 2013/0323242 A1* | 12/2013 | Everett | .............. | A61K 39/3955 424/134.1 |
| 2016/0326530 A1 | 11/2016 | Dausse et al. | | |

FOREIGN PATENT DOCUMENTS

| | | |
|---|---|---|
| CN | 105441213 A | 3/2016 |
| WO | WO9960167 A1 | 11/1999 |
| WO | WO2007149310 A2 | 12/2007 |
| WO | WO2015140722 A1 | 9/2015 |

OTHER PUBLICATIONS

Database WPI, XP002785798, Week 201649, 2016, Thomson Scientific, London GB, AN 2016-20069A.

* cited by examiner

*Primary Examiner* — Tracy Vivlemore

(74) *Attorney, Agent, or Firm* — James E Oehlenschlager

(57) ABSTRACT

Consumer product compositions comprise a surfactant and a nucleic acid aptamer. The nucleic acid aptamer comprises at least one oligonucleotide comprising: deoxyribonucleotides, ribonucleotides, derivatives of deoxyribonucleotides, derivatives of ribonucleotides, or mixtures thereof. The nucleic acid aptamer has a binding affinity for an epitope of a surface being treated with the consumer product composition.

32 Claims, 5 Drawing Sheets (5 of 5 Drawing Sheet(s) Filed in Color)

Specification includes a Sequence Listing.

US 10,676,748 B2

APTAMERS FOR CONSUMER PRODUCT COMPOSITIONS

FIELD OF INVENTION

The present invention generally relates to nucleic acid aptamers that have a high binding affinity and specificity for consumer product applications. This invention also relates to the use of such aptamers as delivery vehicles of active ingredients in consumer product compositions.

BACKGROUND OF THE INVENTION

Aptamers are short single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and π-π stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of aptamers typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method was first introduced in 1990 when single stranded RNAs were selected against low molecular weight dyes (Ellington, A. D., Szostak, J. W., 1990. Nature 346: 818-822). A few years later, single stranded DNA aptamers and aptamers containing chemically modified nucleotides were also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues have been selected. A compilation of examples from the literature is included in the database at the website: http://www.aptagen.com/aptamer-index/aptamer-list.aspx. However, a need still exists for aptamers that have a high binding affinity and specificity for consumer product applications, especially those containing surfactant.

SUMMARY OF THE INVENTION

The present invention relates to consumer product compositions comprising a surfactant and a nucleic acid aptamer. The nucleic acid aptamer comprises at least one oligonucleotide comprising: deoxyribonucleotides, ribonucleotides, derivatives of deoxyribonucleotides, derivatives of ribonucleotides, or mixtures thereof. The nucleic acid aptamer has a binding affinity for an epitope of a surface being treated with the consumer product composition.

In one aspect, the nucleic acid aptamer comprises at least one oligonucleotide comprising SEQ ID NO 1, SEQ ID NO 9, SEQ ID NO 25, SEQ ID NO 112, SEQ ID NO 120, or SEQ ID NO 136.

In another aspect, the consumer product composition further comprises an active ingredient, wherein the nucleic acid aptamer is covalently or non-covalently attached to the active ingredient. In this regard, the nucleic acid aptamer aids in delivery of the active ingredient to the surface being treated with the consumer product composition.

In another aspect, the present invention relates to a method for delivering one or more active ingredients to the surface being treated with a consumer product composition comprising a surfactant, a nucleic acid aptamer, and an active ingredient, wherein the nucleic acid aptamer is covalently or non-covalently attached to the active ingredient.

In another aspect, the consumer product composition further comprises a nanomaterial, wherein the nucleic acid aptamer is covalently or non-covalently attached to the nanomaterial.

BRIEF DESCRIPTION OF THE DRAWINGS

The patent or application file contains at least one drawing/photograph executed in color. Copies of this patent or patent application publication with color drawing(s)/photograph(s) will be provided by the Office upon request and payment of the necessary fee.

For a more complete understanding of the disclosure, reference should be made to the following detailed description and drawing FIGS.

DETAILED DESCRIPTION OF THE INVENTION

Figure 1:
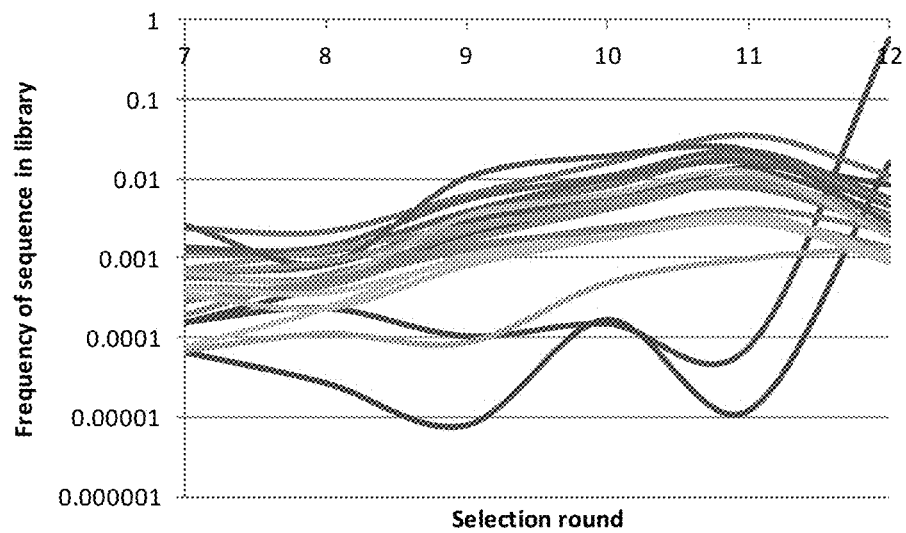
FIG. 1 illustrates the enrichment trajectories of the top twenty sequences in terms of copy number across different selection rounds for Experiment A.

The present invention relates to consumer product compositions comprising one or more aptamers, wherein the aptamers are designed to bind to specific targets, such as epitopes of surfaces being treated with the consumer product compositions. Active ingredients may be included in the consumer product compositions, with the actives being bound to the aptamers thereby allowing the actives to be delivered to the specific target, allowing for greater efficiency and affect.

Definitions

As used herein, the term "aptamer" refers to a single stranded oligonucleotide or a peptide that has a binding affinity for a specific target.

As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleotide" usually refers to a compound consisting of a nucleoside esterified to a monophosphate, polyphosphate, or phosphate-derivative group via the hydroxyl group of the 5-carbon of the sugar moiety. Nucleotides are also referred as "ribonucleotides" when the sugar moiety is D-ribose and as "deoxyribonucleotides" when the sugar moiety is 2-deoxy-D-ribose.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred as "ribonucleosides" when the sugar moiety is D-ribose and as "deoxyribonucleosides" when the sugar moiety is 2-deoxy-D-ribose.

As used herein, the term "nucleobase", refers to a compound containing a nitrogen atom that has the chemical properties of a base. Non-limiting examples of nucleobases are compounds comprising pyridine, purine, or pyrimidine moieties, including, but not limited to adenine, guanine, hypoxanthine, thymine, cytosine, and uracil.

As used herein, the term "oligonucleotide" refers to an oligomer composed of nucleotides.

As used herein, the term "identical" or "sequence identity," in the context of two or more oligonucleotides, nucleic acids, or aptamers, refers to two or more sequences that are the same or have a specified percentage of nucleotides that are the same, when compared and aligned for maximum correspondence, as measured using sequence comparison algorithms or by visual inspection.

As used herein, the term "substantially homologous" or "substantially identical" in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein, the term "motif" refers to the sequence of contiguous, or series of contiguous, nucleotides occurring in a library of aptamers with binding affinity towards a specific target (e.g. teeth) and that exhibit a statistically significant higher probability of occurrence than would be expected compared to a library of random oligonucleotides. The motif sequence is frequently the result or driver of the aptamer selection process.

As used herein the term "binding affinity" may be calculated using the following equation: Binding Affinity=Amount of aptamer bound to a specified target/Total amount of aptamer incubated with the specified target.

By "consumer product composition", as used herein, it is meant compositions for treating hair (human, dog, and/or cat), including bleaching, coloring, dyeing, conditioning, growing, removing, retarding growth, shampooing, and styling; personal cleansing; color cosmetics; products relating to treating skin (human, dog, and/or cat), including creams, lotions, ointments, and other topically applied products for consumer use; products relating to orally administered materials for enhancing the appearance of hair, skin, and/or nails (human, dog, and/or cat); shaving; body sprays; fine fragrances such as colognes and perfumes; compositions for treating fabrics, hard surfaces and any other surfaces in the area of fabric and home care, including air care, car care, dishwashing, fabric conditioning (including softening), fabric freshening, laundry detergents, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps; products relating to oral care compositions including toothpastes, tooth gels, mouth rinses, denture adhesives, and tooth whitening; personal health care medications; products relating to grooming including shave care compositions and composition for coating, or incorporation into, razors or other shaving devices; and compositions for coating, or incorporation into, wet or dry bath tissue, facial tissue, disposable handkerchiefs, disposable towels and/or wipes, incontinence pads, panty liners, sanitary napkins, and tampons and tampon applicators; and combinations thereof.

By "oral care composition", as used herein, is meant a product, which in the ordinary course of usage, is not intentionally swallowed for purposes of systemic administration of therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, the term "oral cavity" means the part of the mouth including the teeth and gums and the cavity behind the teeth and gums that is bounded above by the hard and soft palates and below by the tongue and mucous membrane.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Nucleic Acid Aptamers

Nucleic acid aptamers are single-stranded oligonucleotides, with specific secondary and tertiary structures, that can bind to targets with high affinity and specificity. In certain aspects of the present invention, a nucleic acid aptamer comprises at least one oligonucleotide comprising: deoxyribonucleotides, ribonucleotides, derivatives of deoxyribonucleotides, derivatives of ribonucleotides, or mixtures thereof; wherein said aptamer has a binding affinity for an epitope of a surface being treated.

In another aspect, nucleic acid aptamer includes at least one oligonucleotide comprising oligonucleotides with at least 50% nucleotide sequence identity to sequences that are at least one of SEQ ID NO 1 to SEQ ID NO 222. In another aspect, a nucleic acid aptamer includes at least one oligonucleotide comprising oligonucleotides with at least 70% nucleotide sequence identity to sequences including SEQ ID NO 1 to SEQ ID NO 222. In yet another aspect, a nucleic acid aptamer comprises at least one oligonucleotide having at least 90% nucleotide sequence identity to at least one of SEQ ID NO 1 to SEQ ID NO 222. In another aspect, a nucleic acid aptamer comprises at least one oligonucleotide having at least 20 contiguous nucleotides from at least one of SEQ ID NO 1 to SEQ ID NO 222. In another aspect, a nucleic acid aptamer comprises at least one oligonucleotide having at least 40 contiguous nucleotides from at least one of SEQ ID NO 1 to SEQ ID NO 222. In another aspect, a nucleic acid aptamer comprises at least one oligonucleotide having at least 60 contiguous nucleotides from at least one of SEQ ID NO 1 to SEQ ID NO 222. In another aspect, a nucleic acid aptamer comprises at least one oligonucleotide having at least 70 contiguous nucleotides from at least one of SEQ ID NO 1 to SEQ ID NO 222. In another aspect, a nucleic acid aptamer comprises at least one oligonucleotide having at least 80 contiguous nucleotides from at least one of SEQ ID NO 1 to SEQ ID NO 222.

In another aspect, a nucleic acid aptamer comprises at least one oligonucleotide comprising SEQ ID NO 1, SEQ ID NO 9, SEQ ID NO 25, SEQ ID NO 112, SEQ ID NO 120, or SEQ ID NO 136. In another aspect, a nucleic acid aptamer comprises at least one oligonucleotide having at least 50% nucleotide sequence identity to at least one of SEQ ID NO 1, SEQ ID NO 9, SEQ ID NO 25, SEQ ID NO 112, SEQ ID NO 120, or SEQ ID NO 136. In another aspect, a nucleic acid aptamer comprises at least one oligonucleotide having at least 70% nucleotide sequence identity to at least one of SEQ ID NO 1, SEQ ID NO 9, SEQ ID NO 25, SEQ ID NO 112, SEQ ID NO 120, or SEQ ID NO 136. In another aspect, a nucleic acid aptamer comprises at least one oligonucleotide having at least 90% nucleotide sequence identity to at least one of SEQ ID NO 1, SEQ ID NO 9, SEQ ID NO 25, SEQ ID NO 112, SEQ ID NO 120, or SEQ ID NO 136. Non-limiting examples of oligonucleotides with at least 90% nucleotide sequence identity to SEQ ID NO 1 are SEQ ID NO 49, SEQ ID NO 69, and SEQ ID NO 75. A non-limiting example of an oligonucleotide with at least 50% nucleotide sequence identity to SEQ ID NO 9 is SEQ ID NO 14.

In another aspect, the fluorinated pyrimidine nucleotides of SEQ ID NO 1 to SEQ ID NO 111 are substituted by the corresponding natural non-fluorinated pyrimidine nucleotides.

Other suitable nucleic acid aptamers include those described in a detail in co-pending U.S. application Ser. No. 16/059,597, filed Aug. 9, 2018, entitled "APTAMERS FOR ORAL CARE APPLICATIONS", including SEQ ID NO 223-244 described therein.

Chemical modifications can introduce new features into the aptamers such as different molecular interactions with the target, improved binding capabilities, enhanced stability of oligonucleotide conformations, or increased resistance to nucleases. In certain aspects, an oligonucleotide of a nucleic acid aptamer comprises natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In certain aspects, the nucleosides of oligonucleotides are linked by a chemical motif that is at least one of: natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, or mixtures thereof. In another aspect, the nucleosides of oligonucleotides may be linked by natural phosphate diesters.

In another aspect, the sugar moiety of the nucleosides of oligonucleotides may be at least one of: ribose, deoxyribose, 2'-fluoro deoxyribose, 2'-O-methyl ribose, 2'-O-(3-amino) propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, or mixtures thereof.

In another aspect, said derivatives of ribonucleotides or derivatives of deoxyribonucleotides may be at least one of: locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, or mixtures thereof.

In another aspect, the nucleotides at the 5'- and 3'-ends of an oligonucleotide are inverted. In another aspect, at least one nucleotide of an oligonucleotide is fluorinated at the 2' position of the pentose group. In another aspect, the pyrimidine nucleotides of an oligonucleotide are fluorinated at the 2' position of the pentose group. In another aspect, the nucleic acid aptamer further comprises at least one polymeric material, wherein the polymeric material may be covalently linked to an oligonucleotide; wherein the polymeric material may be polyethylene glycol.

In another aspect, an oligonucleotide may be between about 10 and about 200 nucleotides in length. In another aspect, an oligonucleotide may be less than about 100 nucleotides in length. In yet another aspect, an oligonucleotide may be less than about 50 nucleotides in length.

Aptamers can also be peptides that bind to targets with high affinity and specificity. These peptide aptamers can be part of a scaffold protein. Peptide aptamers can be isolated from combinatorial libraries and improved by directed mutation or rounds of variable region mutagenesis and selection. In certain aspects of the present invention, a nucleic acid aptamer may comprise at least one peptide or protein; wherein the nucleic acid aptamer has a binding affinity for an epitope of a surface treated with the consumer product composition.

Methods of Designing Nucleic Acid Aptamers

The method of designing nucleic acid aptamers known as *Systematic Evolution of Ligands by Exponential Enrichment* (SELEX) has been broadly studied and improved for the selection of aptamers against small molecules and proteins (WO 91/19813). In brief, in the conventional version of SELEX, the process starts with the synthesis of a large library of oligonucleotides consisting of randomly generated sequences of fixed length flanked by constant 5'- and 3'-ends that serve as primers. The oligonucleotides in the library are then exposed to the target ligand and those that do not bind the target are removed. The bound sequences are eluted and amplified by PCR to prepare for subsequent rounds of selection in which the stringency of the elution conditions is usually increased to identify the tightest-binding oligonucleotides. In addition to conventional SELEX, there are improved versions such as capillary electrophoresis-SELEX, magnetic bead-based SELEX, cell-SELEX, automated SELEX, complex-target SELEX, among others. A review of aptamer screening methods is found in "Kim, Y. S. and M. B. Gu (2014). Advances in Aptamer Screening and Small Molecule Aptasensors. Adv. Biochem. Eng./Biotechnol. 140 (Biosensors based on Aptamers and Enzymes): 29-67" and "Stoltenburg, R., et al. (2007). SELEX-A (r)evolutionary method to generate high-affinity nucleic acid ligands. Biomol. Eng. 24(4): 381-403," the contents of which are incorporated herein by reference. Although the SELEX method has been broadly applied, it is neither predictive nor standardized for every target. Instead, a method must be developed for each particular target in order for the method to lead to viable aptamers.

Despite the large number of selected aptamers, SELEX has not been routinely applied for the selection of aptamers with binding affinities towards macroscopic materials and surfaces, especially in the presence of surfactants. Surfactants are well-known to interact with biological materials leading to conformational changes in the three-dimensional structure and making the aptamer selection process more challenging. For the successful selection of aptamers with high binding affinity and specificity against macroscopic materials, the epitope should be present in sufficient amount and purity to minimize the enrichment of unspecifically binding oligonucleotides and to increase the specificity of the selection. Also, the presence of positively charged groups (e.g. primary amino groups), the presence of hydrogen bond donors and acceptors, and planarity (aromatic compounds) in the macroscopic target facilitate the selection of aptamers. In contrast, negatively charged molecules (e.g. containing phosphate groups) make the selection process more difficult. Unexpectedly, in spite of the potential detrimental interactions of surfactants with aptamers that make the selection challenging, the inventors have found that SELEX can be used for the design of aptamers with high binding affinity and specificity for different surfaces.

Selection Library

In SELEX, the initial candidate library is generally a mixture of chemically synthesized DNA oligonucleotides, each comprising a long variable region of n nucleotides flanked, at the 3' and 5' ends, by conserved regions or primer recognition regions for all the candidates of the library. These primer recognition regions allow the central variable region to be manipulated during SELEX, in particular by means of PCR.

The length of the variable region determines the diversity of the library, which is equal to $4^n$ since each position can be occupied by one of four nucleotides A, T, G or C. For long variable regions, huge library complexities arise. For instance, when n=50, the theoretical diversity is $4^{50}$ or $10^{30}$, which is an inaccessible value in practice as it corresponds to more than $10^5$ tons of material for a library wherein each sequence is represented once. The experimental limit is around $10^{15}$ different sequences, which is that of a library wherein all candidates having a variable region of 25 nucleotides are represented. If one chooses to manipulate a library comprising a 30-nucleotide variable region whose theoretical diversity is about $10^{18}$, only 1/1000 of the possibilities will thus be explored. In practice, that is generally sufficient to obtain aptamers having the desired properties.

Additionally, since the polymerases used are unreliable and introduce errors at a rate on the order of $10^{-4}$, they contribute to significantly enrich the diversity of the sequence pool throughout the SELEX process: one candidate in 100 will be modified in each amplification cycle for a library with a random region of 100 nucleotides in length, thus leading to the appearance of $10^{13}$ new candidates for the overall library.

In certain aspects of the present invention, the starting mixture of oligonucleotides may comprise more than about $10^6$ different oligonucleotides or from between about $10^{13}$ to about $10^{15}$ different oligonucleotides. In another aspect of the present invention, the length of the variable region may be between about 10 and about 100 nucleotides. In another aspect, the length of the variable region may be between about 20 and about 60 nucleotides. In yet another aspect, the length of the variable region is about 40 nucleotides. Random regions shorter than 10 nucleotides may be used, but may be constrained in their ability to form secondary or tertiary structures and in their ability to bind to target molecules. Random regions longer than 100 nucleotides may also be used but may present difficulties in terms of cost of synthesis. The randomness of the variable region is not a constraint of the present invention. For instance, if previous knowledge exists regarding oligonucleotides that bind to a given target, libraries spiked with such sequences may work as well or better than completely random ones.

In the design of primer recognition sequences care should be taken to minimize potential annealing among sequences, fold back regions within sequences, or annealing of the same sequence itself. In certain aspects of the present invention, the length of primer recognition sequences may be between about 10 and about 40 nucleotides. In another aspect, the length of primer recognition sequences may be between about 12 and about 30 nucleotides. In yet another aspect, the length of primer recognition sequences may be between about 18 and about 26 nucleotides, i.e., about 18, 19, 20, 21, 22, 23, 24, 25 or 26 nucleotides. The length and sequence of the primer recognition sequences determine their annealing temperature. In certain aspects, the primer recognition sequences of oligonucleotides may have an annealing temperature between about 60° C. and about 72° C.

Aptamers can be ribonucleotides (RNA), deoxynucleotides (DNA), or their derivatives. When aptamers are ribonucleotides, the first SELEX step may consist in transcribing the initial mixture of chemically synthesized DNA oligonucleotides via the primer recognition sequence at the 5' end. After selection, the candidates are converted back into DNA by reverse transcription before being amplified. RNA and DNA aptamers having comparable characteristics have been selected against the same target and reported in the art. Additionally, both types of aptamers can be competitive inhibitors of one another, suggesting potential overlapping of interaction sites.

New functionalities, such as hydrophobicity or photoreactivity, can be incorporated into the oligonucleotides by modifications of the nucleobases before or after selection. Modifications at the C-5 position of pyrimidines or at the C-8 or N-7 positions of purines are especially common and compatible with certain enzymes used during the amplification step in SELEX. In certain aspects of the present invention, said oligonucleotides comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2- naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, 5-bromouracil, 5-iodouracil, and mixtures thereof. Some non-natural nucleobases, such as 5-bromouracil or 5-iodouracil, can be used to generate photo-cross-linkable aptamers, which can be activated by UV light to form a covalent link with the target.

In another aspect, the nucleosides of said oligonucleotides are linked by a chemical motif selected from the group comprising: natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In yet another aspect, the nucleosides of said oligonucleotides are linked by natural phosphate diesters.

In another aspect, the sugar moiety of the nucleosides of said oligonucleotides may be selected from the group comprising: ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy) ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In another aspect, said derivatives of ribonucleotides or said derivatives of deoxyribonucleotides are selected from the group comprising: locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

When using modified nucleotides during the SELEX process, they should be compatible with the enzymes used during the amplification step. Non-limiting examples of modifications that are compatible with commercial enzymes include modifications at the 2' position of the sugar in RNA libraries. The ribose 2'-OH group of pyrimidine nucleotides can be replaced with 2'-amino, 2'-fluoro, 2'-methyl, or 2'-O-methyl, which protect the RNA from degradation by nucleases. Additional modifications in the phosphate linker, such as phosphorothionate and boranophosphate, are also compatible with the polymerases and confer resistance to nucleases.

In certain aspects of the present invention, at least one nucleotide of said oligonucleotides is fluorinated at the 2' position of the pentose group. In another aspect, the pyrimidine nucleotides of said oligonucleotides are at least partially fluorinated at the 2' position of the pentose group. In yet another aspect, all the pyrimidine nucleotides of said oligonucleotides are fluorinated at the 2' position of the pentose group. In another aspect, at least one nucleotide of said oligonucleotides is aminated at the 2' position of the pentose group.

Another approach, recently described as two-dimensional SELEX, simultaneously applies in vitro oligonucleotide selection and dynamic combinatorial chemistry (DCC), e.g., a reversible reaction between certain groups of the oligonucleotide (amine groups) and a library of aldehyde compounds. The reaction produces imine oligonucleotides which are selected on the same principles as for conventional SELEX. It was thus possible to identify for a target hairpin RNA modified aptamers that differ from natural aptamers.

A very different approach relates to the use of optical isomers. Natural oligonucleotides are D-isomers. L-analogs are resistant to nucleases but cannot be synthesized by polymerases. According to the laws of optical isomerism, an L-series aptamer can form with its target (T) a complex having the same characteristics as the complex formed by the D-series isomer and the enantiomer (T') of the target (T). Consequently, if compound T' can be chemically synthesized, it can be used to perform the selection of a natural aptamer (D). Once identified, this aptamer can be chemically synthesized in an L-series. This L-aptamer is a ligand of the natural target (T).

Selection Step

Single stranded oligonucleotides can fold to generate secondary and tertiary structures, resembling the formation of base pairs. The initial sequence library is thus a library of three-dimensional shapes, each corresponding to a distribution of units that can trigger electrostatic interactions, create hydrogen bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets $K_d$ values below $10^{-9}$ M are not rare.

Selection in each round occurs by means of physical separation of oligonucleotides associated with the target from free oligonucleotides. Multiple techniques may be applied (chromatography, filter retention, electrophoresis, etc.). The selection conditions are adjusted (relative concentration of target/candidates, ion concentration, temperature, washing, etc.) so that a target-binding competition occurs between the oligonucleotides. Generally, stringency is increased as the rounds proceed in order to promote the capture of oligonucleotides with the highest affinity. In addition, counter-selections or negative selections are carried out to eliminate oligonucleotides that recognize the support or unwanted targets (e.g., filter, beads, etc.).

The SELEX process for the selection of target-specific aptamers is characterized by repetition of five main steps: binding of oligonucleotides to the target, partition or removal of oligonucleotides with low binding affinity, elution of oligonucleotides with high binding affinity, amplification or replication of oligonucleotides with high binding affinity, and conditioning or preparation of the oligonucleotides for the next cycle. This selection process is designed to identify the oligonucleotides with the greatest affinity and specificity for the target material.

In certain aspects of the present invention, a method of designing a nucleic acid aptamer comprises the step of contacting: a) a mixture of oligonucleotides, b) a selection buffer, and c) a target material. In another aspect of the present invention, said mixture of oligonucleotides comprises oligonucleotides selected from the group consisting of deoxyribonucleotides, ribonucleotides, derivatives of deoxyribonucleotides, derivatives of ribonucleotides, and mixtures thereof.

SELEX cycles are usually repeated several times until oligonucleotides with high binding affinity are identified. The number of cycles depends on multiple variables, including target features and concentration, design of the starting random oligonucleotide library, selection conditions, ratio of target binding sites to oligonucleotides, and the efficiency of the partitioning step. In certain aspects, said contacting step is performed at least 5 times. In another aspect, said contacting step is performed between 6 and 15 times. In another aspect, said method further comprises the step of removing the oligonucleotides that do not bind said target material during said contacting step.

Oligonucleotides are oligo-anions, each unit having a charge and hydrogen-bond donor/acceptor sites at a particular pH. Thus, the pH and ionic strength of the selection buffer are important and should represent the conditions of the intended aptamer application. In certain aspects of the present invention, the pH of said selection buffer is between about 2 and about 9. In another aspect, the pH of said selection buffer is between about 6 and about 8. In yet another aspect, the pH of said selection buffer is between about 2 and about 5. Selection buffers with low pH can be important if the aptamers are expected to have good binding affinities in acidic environments.

Cations can facilitate the proper folding of the oligonucleotides and provide benefits in the particular application. In certain aspects of the present invention, said selection buffer comprises cations. Non-limiting examples of cations are $Ca^{2+}$, $Mg^{2+}$, $Sn^{2+}$, $Sn^{4+}$, $Zn^{2+}$, $Al^{3+}$, $Cu^{2+}$, $Fe^{2+}$, and $Fe^{3+}$.

In order for the aptamers to maintain their structures and function during their application, the in vitro selection process can be carried out under conditions similar to those for which they are being developed. In certain aspects of the present invention, said selection buffer comprises a surfactant, as described hereinbelow as an ingredient in a consumer product composition.

In another aspect, the selection buffer further comprises one or more carrier/solvent, as described hereinbelow as an ingredient in a consumer product composition.

In another aspect, said selection buffer further comprises one or more rheology modifiers, including polymeric materials, as described hereinbelow as an ingredient in a consumer product composition.

In another aspect, the selection buffer further comprises one or more chelating agents, as described hereinbelow as an ingredient in a consumer product composition. In another aspect, the selection buffer further comprises one or more silicones, as described hereinbelow as an ingredient in a consumer product composition.

Negative selection or counter-selection steps can minimize the enrichment of oligonucleotides that bind to undesired targets or undesired epitopes within a target. In certain aspects of the present invention, said method of designing a nucleic acid aptamer further comprises the step of contacting: a) a mixture of oligonucleotides, b) a selection buffer, and c) one or more undesired target materials. During the negative selection or counter-selection, the undesired target materials can be either unbound or immobilized to a support. Methods for negative selection or counter-selection of aptamers against unbound targets have been published in WO201735666, the content of which is incorporated herein by reference.

In certain aspects of the present invention, the method of designing a nucleic acid aptamer may comprise the steps of: a) synthesizing a mixture of oligonucleotides; b) contacting: i. said mixture of oligonucleotides, ii. a selection buffer, and iii. a target material, to produce a target suspension; c) removing the liquid phase from said target suspension to produce a target-oligonucleotide mixture; d) contacting said target-oligonucleotide mixture with a washing buffer and removing the liquid phase to produce a target-aptamer mixture; and e) contacting said target-aptamer mixture with an elution buffer and recovering the liquid phase to produce an aptamer mixture. In another aspect, said steps are performed repetitively at least 5 times. In another aspect, said steps are performed between 6 and 15 times.

In another aspect, a method of designing a nucleic acid aptamer comprising the steps of: a) synthesizing a random mixture of deoxyribonucleotides comprising oligonucleotides consisting of: i. a T7 promoter sequence at the 5'-end, ii. a variable 40-nucleotide sequence in the middle, and iii. a conserved reverse primer recognition sequence at the 3'end; b) transcribing said random mixture of deoxyribonucleotides using pyrimidine nucleotides fluorinated at the 2' position of the pentose group and natural purine nucleotides and a mutant T7 polymerase to produce a mixture of fluorinated ribonucleotides; c) contacting: i. said mixture of fluorinated ribonucleotides, ii. a selection buffer, and iii. a target material, to produce a target suspension; d) removing the liquid phase from said target suspension to produce a target-oligonucleotide mixture; e) contacting said target-oligonucleotide mixture with a washing buffer and removing the liquid phase to produce a target-aptamer mixture; f) contacting said target-aptamer mixture with an elution buffer and recovering the liquid phase to produce an RNA aptamer mixture; g) reserve transcribing and amplifying said RNA aptamer mixture to produce a DNA copy of said RNA aptamer mixture; and h) sequencing said DNA copy of said RNA aptamer mixture.

Post-Selection Modification

To enhance stability of the aptamers, chemical modifications can be introduced in the aptamer after the selection process. For instance, the 2'-OH groups of the ribose moieties can be replaced by 2'-fluoro, 2'-amino, or 2'-O-methyl groups. Furthermore, the 3'- and 5'-ends of the aptamers can be capped with different groups, such as streptavidin-biotin, inverted thymidine, amine, phosphate, polyethylene-glycol, cholesterol, fatty acids, proteins, enzymes, fluorophores, among others, making the oligonucleotides resistant to exonucleases or providing some additional benefits. Other modifications are described in previous sections of the present disclosure.

Unlike backbone modifications which can cause aptamer-target interaction properties to be lost, it is possible to conjugate various groups at one of the 3'- or 5'-ends of the oligonucleotide in order to convert it into a delivery vehicle, tool, probe, or sensor without disrupting its characteristics. This versatility constitutes a significant advantage of aptamers, in particular for their application in the current invention. In certain aspects of the present invention, one or more active ingredients are covalently attached to the 3'-end of an oligonucleotide. In another aspect, one or more active ingredients are covalently attached to the 5'-end of an oligonucleotide. In yet another aspect, one or more active ingredients are covalently attached to random positions of an oligonucleotide.

Incorporation of modifications to aptamers can be performed using enzymatic or chemical methods. Non-limiting examples of enzymes used for modification of aptamers are terminal deoxynucleotidyl transferases (TdT), T4 RNA ligases, T4 polynucleotide kinases (PNK), DNA polymerases, RNA polymerases, and other enzymes known by those skilled in the art. TdTs are template-independent polymerases that can add modified deoxynucleotides to the 3' terminus of deoxyribonucleotides. T4 RNA ligases can be used to label ribonucleotides at the 3'-end by using appropriately modified nucleoside 3',5'-bisphosphates. PNK can be used to phosphorylate the 5'-end of synthetic oligonucleotides, enabling other chemical transformations (see below). DNA and RNA polymerases are commonly used for the random incorporation of modified nucleotides throughout the sequence, provided such nucleotides are compatible with the enzymes.

Non-limiting examples of chemical methods used for modification of aptamers are periodate oxidation of ribonucleotides, EDC activation of 5'-phosphate, random chemical labeling methods, and other chemical methods known by those skilled in the art, incorporated herein as aspects of the current invention.

During periodate oxidation, meta- and ortho-perdionates cleave the C—C bonds between vicinal diols of 3'-ribonucleotides, creating two aldehyde moieties that enable the conjugation of labels or active ingredients at the 3'-end of RNA aptamers. The resulting aldehydes can be easily reacted with hydrazide- or primary amine-containing molecules. When amines are used, the produced Schiff bases can be reduced to more stable secondary amines with sodium cyanoborohydride ($NaBH_4$).

When EDC activation of 5'-phosphate is used, the 5'-phosphate of oligonucleotides is frequently activated with EDC (1-Ethyl-3-[3-dimethylaminopropyl]carbodiimide hydrochloride) and imidazole to produce a reactive imidazolide intermediate, followed by reaction with a primary amine to generate aptamers modified at the 5'end. Because the 5' phosphate group is required for the reaction, synthetic oligonucleotides can be first treated with a kinase (e.g. PNK).

Random chemical labeling can be performed with different methods. Because they allow labeling at random sites along the aptamer, a higher degree of modification can be achieved compared to end-labeling methods. However, since the nucleobases are modified, binding of the aptamers to their target can be disrupted. The most common random chemical modification methods involve the use of photoreactive reagents, such as phenylazide-based reagents. When the phenylazide group is exposed to UV light, it forms a labile nitrene that reacts with double bonds and C—H and N—H sites of the aptamers.

Additional information about methods for modification of aptamers is summarized in "Hermanson G. T. (2008). Bioconjugate Techniques. 2nd Edition. pp. 969-1002, Academic Press, San Diego.", the content of which is incorporated herein by reference.

After selection, in addition to chemical modifications, sequence truncations can be performed to remove regions that are not essential for binding or for folding into the structure. Moreover, aptamers can be linked together to provide different features or better affinity. Thus, any truncations or combinations of the aptamers described herein are incorporated as part of the current invention.

Consumer Product Compositions Comprising Nucleic Acid Aptamers

The aptamers of the current invention can be used in consumer product compositions to provide one or more benefits. In certain aspects of the present invention, a consumer product composition comprises at least one nucleic acid aptamer; preferably wherein said at least one nucleic acid aptamer has a binding affinity for an epitope of a surface being treated with the consumer product composition.

The consumer product composition of the present invention comprises a surfactant and a nucleic acid aptamer as described herein.

Consumer product compositions are described hereinabove. The consumer product compositions are utilized to treat surfaces, such as hair, skin (including scalp, dermis, epidermis, and the like), teeth, internal body parts or organs, teeth, gums, tongues, throat soft tissue, microorganisms, fabrics, dishware, hard surfaces (floors, countertops, and the like, such as ceramic material, polymeric material, metallic material, composite material, natural stone material, and the like), tissues or paper towels, and components (e.g. topsheets, absorbent cores, backsheets, and the like) of absorbent articles (e.g. diapers, sanitary napkins, tampons, wipes, incontinence pads, training pants, and the like).

In another aspect, for example, the consumer product composition is an oral care composition comprising at least one nucleic acid aptamer; wherein said at least one nucleic acid aptamer has a binding affinity for an oral cavity component selected from the group comprising: tooth, enamel, dentin, and any other surfaces in the oral cavity. In another aspect, the oral care composition comprises at least one nucleic acid aptamer; wherein said at least one nucleic acid aptamer has a binding affinity for tooth.

The consumer product compositions of the present invention can be in different forms. Non-limiting examples of said forms are: dentifrices (including dentifrices and toothpowders), mouthwashes, mouthrinses, flosses, brushes, strips, sprays, patches, paint on, dissolvables, edibles, lozenges, gums, chewables, soluble fibers, insoluble fibers, putties, waxes, denture adhesives, denture cleansers, liquids, pastes, granules, beads, Newtonian or non-Newtonian fluids, gels, and sols.

Surfactants

The consumer product compositions of the present invention may comprise greater than about 0.1% by weight of a surfactant or mixture of surfactants. Surfactant levels cited herein are on a 100% active basis, even though common raw materials such as sodium lauryl sulphate may be supplied as aqueous solutions of lower activity.

Suitable surfactant levels are from about 0.1% to about 25%, from about 0.25% to about 10%, or from about 0.5% to about 5% by weight of the total composition. Suitable surfactants for use herein include anionic surfactants, amphoteric surfactants, nonionic surfactants, zwitterionic surfactants, cationic surfactants, and mixtures thereof, though anionic, amphoteric, nonionic and zwitterionic surfactants (and mixtures thereof) are preferred.

Useful anionic surfactants herein include the water-soluble salts of alkyl sulphates and alkyl ether sulphates having from 10 to 18 carbon atoms in the alkyl radical and the water-soluble salts of sulphonated monoglycerides of fatty acids having from 10 to 18 carbon atoms. Sodium lauryl sulphate and sodium coconut monoglyceride sulphonates are examples of anionic surfactants of this type.

Suitable cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; benzalkonium chloride; cetyl trimethylammonium bromide; di-isobutylphenoxyethyl-dimethylbenzylammonium chloride; coconut alkyltrimethyl-ammonium nitrite; cetyl pyridinium fluoride; etc. Certain cationic surfactants can also act as germicides in the compositions disclosed herein.

Suitable nonionic surfactants that can be used in the compositions of the present invention can be broadly defined as compounds produced by the condensation of alkylene oxide groups (hydrophilic in nature) with an organic hydrophobic compound which may be aliphatic and/or aromatic in nature. Examples of suitable nonionic surfactants include the poloxamers; sorbitan derivatives, such as sorbitan di-isostearate; ethylene oxide condensates of hydrogenated castor oil, such as PEG-30 hydrogenated castor oil; ethylene oxide condensates of aliphatic alcohols or alkyl phenols; products derived from the condensation of ethylene oxide with the reaction product of propylene oxide and ethylene diamine; long chain tertiary amine oxides; long chain tertiary phosphine oxides; long chain dialkyl sulphoxides and mixtures of such materials. These materials are useful for stabilising foams without contributing to excess viscosity build for the consumer product composition.

Zwitterionic surfactants can be broadly described as derivatives of aliphatic quaternary ammonium, phosphonium, and sulphonium compounds, in which the aliphatic radicals can be straight chain or branched, and wherein one of the aliphatic substituents contains from about 8 to 18 carbon atoms and one contains an anionic water-solubilising group, e.g., carboxy, sulphonate, sulphate, phosphate or phosphonate.

Surfactants can provide a desirable foaming quality. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.1% to about 25%, preferably from about 0.5% to about 8%, and most preferably from about 1% to about 6%, by weight of the composition.

Active Ingredients

In another aspect, a nucleic acid aptamer may be covalently or non-covalently attached to one or more active ingredients contained in a consumer product composition. Suitable active ingredients include any material that is generally considered as safe for use and provides benefits to the treated surface. Examples of suitable active ingredients include those selected from the group comprising: can include perfumes, perfume microcapsules, brighteners, dyes, insect repellants, silicones, waxes, flavors, vitamins, sunscreen agents, anti-acne agents (e.g. salicylic acid or benzylperoxide) conditioning agents (e.g. fabric conditioning agents or hair conditioning agents), skin care agents, enzymes, anti-bacterial agents, bleaches, whitening agents, brightening agents, anti-stain agents, anti-cavity agents, anti-erosion agents, anti-tartar agents, anti-calculus agents, anti-plaque agents, teeth remineralizing agents, anti-fracture agents, strengthening agents, abrasion resistance agents, anti-gingivitis agents, anti-microbial agents, anti-bacterial agents, anti-fungal agents, anti-yeast agents, anti-viral, anti-malodor agents, breath freshening agents, sensates (e.g. cooling agents), taste enhancement agents, olfactory enhancement agents, anti-adherence agents, smoothness agents, surface modification agents, anti-tooth pain agents, anti-sensitivity agents, anti-inflammatory agents, gum protecting agents, periodontal actives, tissue regeneration agents, anti-blood coagulation agents, anti-clot stabilizer agents, salivary stimulant agents, salivary rheology modification agents, enhanced retention agents, soft/hard tissue targeted agents, tooth/soft tissue cleaning agents, antioxidants, pH modifying agents, H-2 antagonists, analgesics, natural extracts and essential oils, dyes, optical brighteners, cations, phosphates, fluoride ion sources, peptides, nutrients, mouth and throat products, and mixtures thereof.

In another aspect, a nucleic acid aptamer is non-covalently attached to one or more active ingredients, via molecular interactions. Examples of molecular interactions are electrostatic forces, van der Waals interactions, hydrogen bonding, and π-π stacking interactions of aromatic rings.

In another aspect, a nucleic acid aptamer may be covalently attached to said one or more active ingredients, for example, using one or more linkers or spacers. Non-limiting examples of linkers are chemically labile linkers, enzyme-labile linkers, and non-cleavable linkers. Examples of chemically labile linkers are acid-cleavable linkers and disulfide linkers. Acid-cleavable linkers take advantage of low pH to trigger hydrolysis of an acid-cleavable bond, such as a hydrazone bond, to release the active ingredient or payload. Disulfide linkers can release the active ingredients under reducing environments. Examples of enzyme-labile linkers are peptide linkers that can be cleaved in the present of proteases and β-glucuronide linkers that are cleaved by glucuronidases releasing the payload. Non-cleavable linkers can also release the active ingredient if the aptamer is degraded by nucleases.

Active ingredients suitable herein are described hereinbelow in more detail in the context of adjunct ingredients. When such ingredients are covalently or non-covalently attached to a nucleic acid aptamer, such ingredients are considered active ingredients for purposes of the present invention. When such ingredients are not attached to a nucleic acid aptamer, such ingredients are considered adjunct ingredients for purposes of the present invention.

Examples of other active ingredients suitable include the following: anti-caries agents (e.g., water soluble fluoride salts, fluorosilicates, fluorozirconates, fluorostannites, fluoroborates, fluorotitanates, fluorogermanates, mixed halides and casine); anti-tartar agents; anti-calculus agents (e.g.

alkali-metal pyrophosphates, hypophosphite-containing polymers, organic phosphocitrates, phosphocitrates, polyphosphates); anti-bacterial agents (e.g., bacteriocins, antibodies, enzymes); anti-bacterial enhancing agents; antimicrobial agents (e.g., Triclosan, chlorhexidine, copper-, zinc- and stannous salts such as zinc citrate, zinc sulfate, zinc glycinate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenbis-(4-chloro-6-bromophenol)); desensitizing agents (e.g., potassium citrate, potassium chloride, potassium tartrate, potassium bicarbonate, potassium oxalate, potassium nitrate and strontium salts); whitening agents (e.g., bleaching agents such as peroxy compounds, e.g. potassium peroxydiphosphate); anti-plaque agents; gum protecting agents (e.g., vegetable oils such as sunflower oil, rape seed oil, soybean oil and safflower oil, and other oils such as silicone oils and hydrocarbon oils). The gum protection agent may be an agent capable of improving the permeability barrier of the gums. Other active ingredients include wound healing agents (e.g., urea, allantoin, panthenol, alkali metal thiocyanates, chamomile-based actives and acetylsalicylic acid derivatives, ibuprofen, flurbiprofen, aspirin, indomethacin etc.); tooth buffering agents; demineralization agents; anti-inflammatory agents; anti-malodor agent; breath freshening agents; and agents for the treatment of oral conditions such as gingivitis or periodontitis.

Nanomaterials

In another aspect, a nucleic acid aptamer may be covalently or non-covalently attached to one or more nanomaterials. In another aspect, a nucleic acid aptamer and one or more active ingredients may be covalently or non-covalently attached to one or more nanomaterials. In another aspect, one or more active ingredients are carried by one or more nanomaterials. Non-limiting examples of nanomaterials are gold nanoparticles, nano-scale iron oxides, carbon nanomaterials (such as single-walled carbon nanotubes and graphene oxide), mesoporous silica nanoparticles, quantum dots, liposomes, poly (lactide-co-glycolic acids) nanoparticles, polymeric micelles, dendrimers, serum albumin nanoparticles, and DNA-based nanomaterials. These nanomaterials can serve as carriers for large volumes of active ingredients, while the aptamers can facilitate the delivery of the nanomaterials with the actives to the expected target.

Nanomaterials can have a variety of shapes or morphologies. Non-limiting examples of shapes or morphologies are spheres, rectangles, polygons, disks, toroids, cones, pyramids, rods/cylinders, and fibers. In the context of the present invention, nanomaterials may have at least one spatial dimension that is less than about 100 μm and more preferably less than about 10 μm. Nanomaterials comprise materials in solid phase, semi-solid phase, or liquid phase.

Other Adjunct Ingredients

The consumer product compositions of the present invention can comprise one or more of the following adjunct ingredients. Such adjunct ingredients can include active ingredients that are not covalently or non-covalently attached to the nucleic acid aptamer. Adjunct ingredients that may be considered active ingredients themselves and are covalently or non-covalently attached to the nucleic acid aptamer, are considered active ingredients for purposes of the present invention.

Perfume—Perfume oil can be added to the consumer product compositions to impart olfactory benefits to the composition itself or to the surfaces treated with the composition. Perfume raw materials and the resulting perfume oils are well known to those of ordinary skill in the art.

Perfume Microcapsules—Perfume microcapsules include core-shell microcapsules in which the core comprises a perfume oil and the shell comprises polymeric material such as melamine formaldehyde, polyacrylate, polyurethane, gelatin, and the like. Upon fracture of the shell of the microcapsule, the perfume oil core is released from the microcapsule.

Conditioning Agents—The consumer product compositions can comprising a conditioning agent suitable for conditioning surfaces such as hair or fabrics. Suitable conditioning agents are typically water-insoluble, non-volatile liquids. Non-limiting examples of suitable conditioning agents for use in the composition are those conditioning agents characterized generally as silicones (e.g., silicone oils, aminosilicones, cationic silicones, silicone gums, high refractive silicones, functionalized silicones, silicone resins, alkyl siloxane polymers, and cationic organopolysiloxanes), organic conditioning oils (e.g., hydrocarbon oils, polyolefins, fatty esters, metathesized unsaturated polyol esters, and silane-modified oils) or combinations thereof. Suitable conditioning agents are selected from the group consisting of silicones, organic conditioning oils, hydrocarbon oils, fatty esters, metathesized unsaturated polyol esters, silane-modified oils, other conditioning agents, and mixtures thereof.

Rheology Modifiers—Rheology modifiers suitable for use in the present invention include organic and inorganic rheology modifiers, and mixtures thereof. Inorganic rheology modifiers include hectorite and derivatives, hydrated silicas, ternary and quaternary magnesium silicate derivatives, bentonite and mixtures thereof. Preferred inorganic rheology modifiers are hectorite and derivatives, hydrated silicas and mixtures thereof. Organic rheology modifiers include xanthan gum, carrageenan and derivatives, gellan gum, hydroxypropyl methyl cellulose, sclerotium gum and derivatives, pullulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives, polyacrylates and derivatives, methyl cellulose and derivatives, ethyl cellulose and derivatives, agar and derivatives, gum arabic and derivatives, pectin and derivatives, chitosan and derivatives, resinous polyethylene glycols such as PEG-XM where X is >=1, karaya gum, locust bean gum, natto gum, co-polymers of vinyl pyrollidone with alkenes, tragacanth gum, polyacrylamides, chitin derivatives, gelatin, betaglucan, dextrin, dextran, cyclodextrin, methacrylates, microcrystalline cellulose, polyquatemiums, furcellaren gum, ghatti gum, psyllium gum, quince gum, tamarind gum, larch gum, tara gum, and mixtures thereof. Preferred are xanthan gum, carrageenan and derivatives, gellan gum, hydroxypropyl methyl cellulose, sclerotium gum and derivatives, pullulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives and mixtures thereof.

Examples of rheology modifiers also include sodium carboxymethyl-cellulose, cellulose ether, xanthan gum, carrageenan, sodium alginate, carbopol, or silicates such as hydrous sodium lithium magnesium silicate. Other examples of suitable rheology modifiers include polymers such as hydroxypropyl methylcellulose, hydroxyethyl cellulose, guar gum, tragacanth gum, karaya gum, arabic gum, Irish moss, starch, and alginate. Alternatively, the rheology modifier can include a clay, for example, a synthetic clay such as a hectorite, or a natural clay. Each of the rheology modifiers can be used alone or in combination with other rheology modifiers.

Rheology modifiers can include polymeric materials such as hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. Other suitable polymeric materials include acrylamide/ammonium acrylate copolymer (and)polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (ME-HEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate.

Non-limiting examples of other rheology modifiers include thickening silica, for example, SILODENT 15 hydrated silica, in the amount between about 4% to about 8% by weight (e.g., about 6%).

In certain aspects amounts of rheology modifiers may range from about 0.1% to about 15% or from about 0.5% to about 3% by weight of the total consumer product composition.

Sweetener—As a sweetener, saccharin sodium, sucrose, maltose, lactose, stevioside, neohesperidildigydrochalcone, glycyrrhizin, perillartine, p-methoxycinnamic aldehyde and the like may be used, in an amount of 0.05 to 5% by weight of the total composition. Essential oils such as spearmint oil, peppermint oil, salvia oil, eucalyptus oil, lemon oil, lime oil, wintergreen oil and cinnamon oil, other spices and fruit flavors as well as isolated and synthetic flavoring materials such as 1-menthol, carvone, anethole, eugenol and the like can be used as flavors. The flavor may be blended in an amount of 0.1 to 5% by weight of the total composition. Sweetening agents such as sodium saccharin, sodium cyclamate, Acesulfame K, aspartame, sucrose and the like may be included at levels from about 0.1 to 5% by weight. Other additives may also be incorporated including flavours, preservatives, opacifiers and colorants.

Flavors—Non-limiting examples of flavoring and cooling agents are menthol, menthone, methyl acetate, menthofuran, 1,8-cineol, R-(-)-carvone, limonene, dihydrocarvone, methyl salicylate, sugar alcohols or polyols (e.g. xylitol, sorbitol, and erythritol), and their derivatives. A non-limiting example of teeth remineralizing agents is hydroxyapatite nanocrystals.

Preservative—Ethyl paraoxy benzonate, butyl paraoxy benzoate, etc. may be used as the preservative.

Carrier/Solvent—The consumer product compositions of the present invention may comprise greater than about 50%, by weight of the composition, of liquid carrier. Suitable carriers/solvents are lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol. Examples of carriers include water, polyethylene glycol, glycerin, polypropylene glycol, starches, sucrose, alcohols (e.g., methanol, ethanol, isopropanol, etc.), or combinations thereof. Examples of combinations include various water and alcohol combinations and various polyethylene glycol and polypropylene glycol combinations. In general, the amount of carrier included is determined based on the concentration of any rheology modifier along with the amount of dissolved salts, surfactants, and dispersed phase.

Generally, humectants are polyols. Examples of humectants include glycerin, sorbitol propyleneglycol, xylitol, lactitol, polypropylene glycol, polyethylene glycol, hydrogenated corn syrup and mixtures thereof. In general, when humectants are included they can be present in an amount from about 10% to about 60% by weight.

Water may comprise from about 20% to about 70% or from about 30% to about 50% by weight of the total composition. These amounts of water include the free water which is added plus that which is introduced with other materials such as with sorbitol and with surfactant solutions.

Generally, the liquid carrier may further include one or more humectants. Suitable humectants include glycerin, sorbitol, and other edible polyhydric alcohols, such as low molecular weight polyethylene glycols at levels of from about 15% to about 50%. To provide the best balance of foaming properties and resistance to drying out, the ratio of total water to total humectant may be from about 0.65:1 to about 1.5:1, or from about 0.85:1 to about 1.3:1.

Ethanol may also be present in the consumer product compositions. These amounts may range from about 0.5 to about 5%, or from about 1.5 to about 3.5% by weight of the total composition. Ethanol can be a useful solvent and can also serve to enhance the impact of a flavour, though in this latter respect only low levels are usually employed. Non-ethanolic solvents such as propylene glycol may also be employed. Also useful herein are low molecular weight polyethylene glycols.

The viscosities of the consumer product compositions herein may be affected by the viscosity of Newtonian liquids, such as humectants, present in the composition. These may be either pure liquids such as glycerin or water, or a solution of a solute in a solvent such as a sorbitol solution in water. The level of contribution of the Newtonian liquid to the viscosity of the non-Newtonian composition will depend upon the level at which the Newtonian liquid is incorporated. Water may be present in a significant amount in a consumer product composition, and has a Newtonian viscosity of approximately 1 mPa·s at 25 deg. C. Humectants such as glycerin and sorbitol solutions typically have a significantly higher Newtonian viscosity than water. As a result, the total level of humectant, the ratio of water to humectant, and the choice of humectants, helps to determine the high shear rate viscosity of the compositions.

Common humectants such as sorbitol, glycerin, polyethyleneglycols, propylene glycols and mixtures thereof may be used, but the specific levels and ratios used will differ depending on the choice of humectant. Sorbitol may be used, but due to its relatively high Newtonian viscosity, in certain aspects cannot be incorporated at levels above 45% by weight of the composition, as it contributes significantly to the high shear rate viscosity of the consumer product composition. Conversely, propylene glycol may be employed at higher levels as it has a lower Newtonian viscosity than sorbitol, and hence does not contribute as much to the high shear rate viscosity of the consumer product composition. Glycerin has an intermediate Newtonian viscosity in between that of sorbitol and polyethylene glycol.

Abrasives—The consumer product compositions of the present invention may comprise an abrasive, such as those used in dentifrice compositions or hard surface cleaning compositions. Abrasives serve to polish the treated surface, remove surface deposits, or both. The abrasive material contemplated for use herein can be any material which does not excessively abrade the surface being treated. Suitable abrasives include insoluble phosphate polishing agents, such as, for example, dicalcium phosphate, tricalcium phosphate, calcium pyrophosphate, beta-phase calcium pyrophosphate, dicalcium phosphate dihydrate, anhydrous calcium phosphate, insoluble sodium metaphosphate, and the like. Also suitable are chalk-type abrasives such as calcium and magnesium carbonates, silicas including xerogels, hydrogels, aerogels and precipitates, alumina and hydrates thereof such as alpha alumina trihydrate, aluminosilicates such as calcined aluminium silicate and aluminium silicate, magnesium and zirconium silicates such as magnesium trisilicate and thermosetting polymerised resins such as particulate condensation products of urea and formaldehyde, polymethylmethacrylate, powdered polyethylene and others such as disclosed in U.S. Pat. No. 3,070,510. Mixtures of abrasives can also be used. The abrasive polishing materials generally have an average particle size of from about 0.1 to about 30 µm, or from about 1 to about 15 µm.

Silica abrasives of various types offer exceptional cleaning and polishing performance without unduly abrading the treated surface. The silica abrasive can be precipitated silica or silica gels such as the silica xerogels described in U.S. Pat. Nos. 3,538,230, 3,862,307. Silicas may be used that have an oil absorption from 30 g per 100 g to 100 g per 100 g of silica. It has been found that silicas with low oil absorption levels are less structuring, and therefore do not build the viscosity of the consumer product composition to the same degree as those silicas that are more highly structuring, and therefore have higher oil absorption levels. As used herein, oil absorption is measured by measuring the maximum amount of linseed oil the silica can absorb at 25 deg. C.

Suitable abrasive levels may be from about 0% to about 20% by weight of the total composition, in certain aspects less than 10%, such as from 1% to 10%. In certain aspects abrasive levels from 3% to 5% by weight of the total composition can be used.

Fluoride—For anticaries protection, a source of fluoride ion will normally be present in the consumer product composition, especially when the composition is an oral care composition. Fluoride sources include sodium fluoride, potassium fluoride, calcium fluoride, stannous fluoride, stannous monofluorophosphate and sodium monofluoro-phosphate. Suitable levels provide from 25 to 2500 ppm of available fluoride ion by weight of the oral care composition.

Chelating Agents—Suitable chelating agents include organic acids and their salts, such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high, resulting in tooth demineralisation. In certain aspects the chelating agents have a calcium binding constant of about 101 to about 105 to provide improved cleaning with reduced plaque and calculus formation. The amounts of chelating that may be used in the formulations of the present invention are about 0.1% to about 2.5%, from about 0.5% to about 2.5% or from about 1.0% to about 2.5%. The tartaric acid salt chelating agent can be used alone or in combination with other optional chelating agents.

Another group of agents particularly suitable for use as chelating agents in the present invention are the water soluble polyphosphates, polyphosphonates, and pyro-phosphates which are useful as anticalculus agents. The pyrophosphate salts used in the present compositions can be any of the alkali metal pyrophosphate salts. An effective amount of pyrophosphate salt useful in the present composition is generally enough to provide at least 1.0% pyrophosphate ion or from about 1.5% to about 6% of such ions. The pyrophosphate salts are described in more detail in Kirk & Othmer, Encyclopedia of Chemical Technology, Second Edition, Volume 15, Interscience Publishers (1968).

Water soluble polyphosphates such as sodium tripolyphosphate, potassium tripolyphosphate and sodium hexametaphosphate may be used. Other long chain anticalculus agents of this type are described in WO98/22079. Also preferred are the water soluble diphosphonates. Suitable soluble diphosphonates include ethane-1-hydroxy-1,1,-diphosphonate (EHDP) and aza-cycloheptane-diphosphonate (AHP). The tripolyphosphates and diphosphonates are particularly effective as they provide both anti-tartar activity and stain removal activity without building viscosity as much as much as less water soluble chemical stain removal agents and are stable with respect to hydrolysis in water. The soluble polyphosphates and diphosphonates are beneficial as destaining actives. Without wishing to be bound by theory, it is believed that these ingredients remove stain by desorbing stained pellicle from surfaces, such as enamel of a tooth. Suitable levels of water soluble polyphosphates and diphosphonates are from about 0.1% to about 10%, from about 1% to about 5%, or from about 1.5% to about 3% by weight of the consumer product composition.

Still another possible group of chelating agents suitable for use in the present invention are the anionic polymeric polycarboxylates. Such materials are well known in the art, being employed in the form of their free acids or partially or preferably fully neutralised water-soluble alkali metal (e.g. potassium and preferably sodium) or ammonium salts. Additional polymeric polycarboxylates are disclosed in U.S. Pat. Nos. 4,138,477 and 4,183,914, and include copolymers of maleic anhydride with styrene, isobutylene or ethyl vinyl ether, polyacrylic, polyitaconic and polymaleic acids, and sulphoacrylic oligomers of MW as low as 1,000 available as Uniroyal ND-2.

Antimicrobial Agents—Also useful for the present invention are antimicrobial agents. A wide variety of antimicrobial agents can be used, including stannous salts such as stannous pyrophosphate and stannous gluconate; zinc salt, such as zinc lactate and zinc citrate; copper salts, such as copper bisglycinate; quaternary ammonium salts, such as cetyl pyridinium chloride and tetradecylethyl pyridinium chloride; bis-biguanide salts; and nonionic antimicrobial agents such as triclosan. Certain flavour oils, such as thymol, may also have antimicrobial activity. Such agents are disclosed in U.S. Pat. Nos. 2,946,725 and 4,051,234. Also useful is sodium chlorite, described in WO 99/43290.

Other antimicrobial agents may include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (Merck Index, no. 2090), alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nisin preparations; zinc/stannous ion agents; bacteriocins; antibiotics such as augmentin, amoxicillin, tetracycline, doxycycline, minocycline, and metronidazole; and analogs and salts of the above anti-microbial anti-plaque agents; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite, and mixtures thereof.

Antimicrobial agents can also include p-hydroxybenzoic acid methyl, ethyl, or propyl ester, sodium sorbate, sodium benzoate, bromochlorophene, triclosan, hexetidine, phenyl silicylate, biguanides, and peroxides.

Antimicrobial agents, if present, are typically included at levels of from about 0.01% to about 10%. Levels of stannous and cationic antimicrobial agents can be kept to less than about 5% or less than about 1% to avoid staining problems.

In certain aspects antimicrobial agents are non-cationic antimicrobial agent, such as those described in U.S. Pat. No. 5,037,637. A particularly effective antimicrobial agent is 2',4,4'-trichloro-2-hydroxy-diphenyl ether (triclosan).

Silicone—An optional ingredient in the present compositions is a silicone oil. Silicone oils can be useful as plaque barriers, as disclosed in WO 96/19191. Suitable classes of silicone oils include, but are not limited to, dimethicones, dimethiconols, dimethicone copolyols and aminoalkylsilicones. Silicone oils are generally present in a level of from about 0.1% to about 15%, from about 0.5% to about 5%, or from about 0.5% to about 3% by weight.

Silicone materials can also serve as conditioning agents in the consumer product compositions, such as in fabric softening compositions or hair conditioning compositions.

Colorant—Typical colorants are D&C Yellow No. 10, FD&C Blue No. 1, FD&C Red No. 40, D&C Red No. 33 and combinations thereof. Levels of the colorant may range from about 0.0001 to about 0.1%.

Whitening Agents/Dyes—Non-limiting examples of whitening agents are dyes, optical brighteners, peroxides, metal chlorites, perborates, percarbonates, peroxyacids, and mixtures thereof. Suitable peroxide compounds include hydrogen peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. The preferred chlorite is sodium chlorite.

Non-limiting examples of dyes are triarylmethane dyes, including brilliant blue FCF (FD&C blue 1 or D&C blue 4), fast green FCF (FD&C green 3), and patent blue V; indigoid dyes, including indigo carmine (FD&C blue 2); anthraquinone dyes, including sunset violet 13 (D&C violet 2); azoic dyes; xanthene dyes; natural dyes, including chlorophylls, spirulina, and anthocyanins; their derivatives; and mixtures thereof.

Optical Brighteners—Optical brighteners, also known as fluorescent whitening agents, are organic compounds that are colorless to weakly colored in solution, absorb ultraviolet light (e.g. from daylight, ca. 300-430 nm), and reemit most of the absorbed energy as blue fluorescent light (400-500 nm). Thus, in daylight, optical brighteners can compensate for the often undesirable yellowish tone found in teeth and other materials. Furthermore, since day UV light (not perceived by the eye) is converted to visible light, the brightness of the teeth can be enhanced to produce a luminous white. Non-limiting examples of optical brighteners are derivatives of carbocyles, stilbene and 4,4'-diaminostilbene, including 4,4'-diamino-2,2'-stilbenedisulfonic acid; derivatives of distyrylbenzenes, distyrylbiphenyls, and divinylstilbenes; derivatives of triazinylaminostilbenes; derivatives of stilbenyl-2H-triazoles; derivatives of benzoxazoles, stilbenylbenzoxazoles, and bis(benzoxazoles); derivatives of furans, benzo[b]furans, benzimidazoles, bix (benzo[b]furan-2-yl)biphenyls, and cationic benzimidazoles; derivatives of 1,3-diphenyl-2-pyrazolines; derivatives of coumarins; derivatives of napthalimides; derivatives of 1,3,5-triazin-2-yl; derivatives of bis(benzoxazol-2-yl); and mixtures thereof. A review of commonly used optical brighteners is found in "Optical Brighteners" by Siegrist, A. E., Eckhardt, C., Kaschig, J. and Schmidt, E.; Ullmann's Encyclopedia of Industrial Chemistry, Wiley and Sons, 2003, the contents of which are incorporated herein by reference. In certain aspects of the present invention, said active ingredient is 4,4'-diamino-2,2'-stilbenedisulfonic acid.

Anti-Cavity Agents—Non-limiting examples of anti-cavity agents are: a) phosphorus-containing agents, including polyphosphates such as pyrophosphate, tripolyphosphate, trimetaphosphate, and hexametaphosphate; organic phosphates such as glycerophosphate, phytate, 1,6-fructose diphosphate, calcium lactophosphate, casein-phosphopeptide amorphous calcium phosphate (CPP-ACP), and sodium caseinate; phosphoproteins; phosphonates such as ethane hydroxy diphosphonate; and phosphosilicates; b) calcium-containing agents, including calcium lactate; c) anti-microbial agents; d) metals and their cations, including zinc, tin, aluminum, copper, iron, and calcium; e) other organic agents including citrate; and f) fluoride-ion sources agents, including sodium fluoride, stannous fluoride, amine fluorides such as olaflur (amine fluoride 297) and dectaflur, sodium monofluorophosphate, fluorosilicates, fluorozirconates, fluorostannites, fluoroborates, fluorotitanates, and fluorogermanates. Non-limiting examples of cations are $Ca^{2+}$, $Sn^{2+}$, $Sn^{4+}$, $Zn^{2+}$, $Al^{3+}$, $Cu^{2+}$, $Fe^{2+}$, and $Fe^{3+}$.

Anti-tartar Agents—Anti-tartar agents known for use in oral care compositions also include phosphates, such as pyrophosphates, polyphosphates, polyphosphonates and mixtures thereof. Pyrophosphates are among the best known for use in dental care products. Pyrophosphate ions delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. While any of the above-mentioned pyrophosphate salts may be used, tetrasodium pyrophosphate salt is preferred.

The pyrophosphate salts are described in more detail in Kirk & Othmer, Encyclopedia of Chemical Technology, Third Edition, Volume 17, Wiley-Interscience Publishers (1982). Additional anti-calculus agents include pyrophosphates or polyphosphates disclosed in U.S. Pat. No. 4,590,066 issued to Parran & Sakkab on May 20, 1986; polyacrylates and other polycarboxylates, such as those disclosed in U.S. Pat. No. 3,429,963 issued to Shedlovsky on Feb. 25, 1969, U.S. Pat. No. 4,304,766 issued to Chang on Dec. 8, 1981 and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989. Anti-calculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Anti-inflammatory Agents—Anti-inflammatory agents can also be present in the consumer product compositions or substances of the present invention. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as ketorolac is claimed in U.S. Pat. No. 5,626,838, issued May 6, 1997. Disclosed therein are methods of preventing and/or treating primary and reoccurring squamous cell carcinoma of the oral cavity or oropharynx by topical administration to the oral cavity or oropharynx an effective amount of an NSAID.

Nutrients—Nutrients include minerals, vitamins, oral nutritional supplements, enteral nutritional supplements, and mixtures thereof. Minerals that can be included with the compositions of the present invention include calcium, phosphorus, fluoride, zinc, magnesium, manganese, potassium and mixtures thereof. These minerals are disclosed in Drug Facts and Comparisons (loose leaf drug information service), Wolters Kluer Company, St. Louis, Mo., (c) 1997, pp 10-17. Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., (c)$_{1997}$, pp. 3-10. Oral nutritional supplements include amino acids, lipotropics, fish oil, and mixtures thereof, as disclosed in Drug Facts and Comparisons (loose leaf drug information service), Wolters Kluer Company, St. Louis, Mo., (c)$_{1997}$, pp. 54-54e. Amino acids include L-tryptophan, L-lysine, methionine, threonine, levocarnitine or L-carnitine and mixtures thereof. Lipotropics include, but, are not limited to choline, inositol, betaine, linoleic acid, linolenic acid, and mixtures thereof. Fish oil contains large amounts of omega-3 (N-3) polyunsaturated fatty acids, eicosapentaenoic acid and docosahexaenoic acid. Enteral nutritional supplements include, but, are not limited to protein products, glucose polymers, corn oil, safflower oil, medium chain triglycerides as disclosed in Drug Facts and Comparisons (loose leaf drug information service), Wolters Kluer Company, St. Louis, Mo., (c) 1997, pp. 55-57.

Enzymes—Enzymes useful in the present invention include any of the commercially available proteases, glucanohydrolases, endoglycosidases, amylases, mutanases, lipases and mucinases or compatible mixtures thereof. Preferred are the proteases, dextranases, endoglycosidases and mutanases, most preferred being papain, endoglycosidase or a mixture of dextranase and mutanase. Additional enzymes suitable for use in the present invention are disclosed in U.S. Pat. No. 5,000,939 to Dring et al.; U.S. Pat. No. 4,992,420 to Neeser; U.S. Pat. No. 4,355,022 to Rabussay; U.S. Pat. No. 4,154,815 to Pader; U.S. Pat. No. 4,058,595 to Colodney; U.S. Pat. No. 3,991,177 to Virda et al. and U.S. Pat. No. 3,696,191 to Weeks.

Antioxidants—Antioxidants are generally recognized as useful in consumer product compositions such as those of the present invention. Antioxidants are disclosed in texts such as Cadenas and Packer, The Handbook of Antioxidants, (c) 1996 by Marcel Dekker, Inc. Antioxidants that may be included in the consumer product composition of the present invention include, but are not limited to vitamin E, ascorbic acid, uric acid, carotenoids, Vitamin A, flavonoids and polyphenols, herbal antioxidants, melatonin, aminoindoles, lipoic acids and mixtures thereof.

Polishing Agents—Non-limiting examples of polishing agents include abrasive materials, such as carbonates (e.g., sodium bicarbonate, calcium carbonate) water-colloidal silica, precipitated silicas (e.g., hydrated silica), sodium aluminosilicates, silica grades containing alumina, hydrated alumina, dicalcium phosphates, calcium hydrogen phosphates, calcium pyrophosphate, calcium pyrophosphate (beta phase), hydroxyapatite, insoluble sodium metaphosphate, and magnesiums (e.g., trimagnesium phosphate). A suitable amount of polishing agent is an amount that safely provides good polishing and cleaning and which, when combined with other ingredients gives a smooth, flowable, and not excessively gritty composition. In general, when polishing agents are included, they are present in an amount from about 5% to about 50% by weight (e.g., from about 5% to about 35%, or from about 7% to about 25%).

Buffers—Examples of buffers and salts include primary, secondary, or tertiary alkali metal phosphates, citric acid, sodium citrate, sodium saccharin, tetrasodium pyrophosphate, sodium hydroxide, and the like.

The consumer product compositions of the present invention may also include one or more of other ingredients, comprising: phenolic compounds (e.g., phenol and its homologues, including 2-methyl-phenol, 3-methyl-phenol, 4-methyl-phenol, 4-ethyl-phenol, 2,4-dimethyl-phenol, and 3,4-dimethyl-phenol); sweetening agents (e.g., sodium saccharin, sodium cyclamate, sucrose, lactose, maltose, and fructose); flavors (e.g., peppermint oil, spearmint oil, eucalyptus oil, aniseed oil, fennel oil, caraway oil, methyl acetate, cinnamaldehyde, anethol, vanillin, thymol and other natural or nature-identical essential oils or synthetic flavors); preservatives (e.g., p-hydroxybenzoic acid methyl, ethyl, or propyl ester, sodium sorbate, sodium benzoate, bromochlorophene, triclosan, hexetidine, phenyl silicylate, biguanides, and peroxides); opacifying and coloring agents such as titanium dioxide or FD&C dyes; and vitamins such as retinol, tocopherol or ascorbic acid.

The consumer product composition preferably comprises at least one nucleic acid aptamer at a level where upon directed use, promotes one or more benefits without detriment to the surface it is applied to. In certain aspects of the present invention, said consumer product composition comprises between about 0.00001% to about 10% of a nucleic acid aptamer. In another aspect, said consumer product composition comprises between about 0.00005% to about 5% of a nucleic acid aptamer. In another aspect, said consumer product composition comprises between about 0.0001% to about 1% of a nucleic acid aptamer.

In another aspect, a consumer product composition comprises at least one peptide aptamer; wherein said at least one peptide aptamer has a binding affinity for an epitope of the surface being treated with the consumer product composition.

The aptamers of the present invention could provide several benefits when bound to a surface. With respect to surfaces of an oral cavity, benefits may include, but are not limited to, teeth remineralization (e.g. by improving calcium deposition on teeth), teeth acid resistance, appearance and structural changes to teeth, stain prevention (e.g. by repelling teeth staining materials such as dyes or pigments), plaque prevention, tartar prevention, and cavity prevention and treatment. As an example, if aptamers comprising fluorinated nucleotides are degraded or decomposed after binding, they could effectively deliver fluoride ions to teeth, which can provide cavity prevention benefits. Non-limiting examples of fluorinated nucleotides include fluorophosphate nucleotides, 2'-fluoro deoxyribonucleotides, and nucleotides with fluorinated nucleobases.

The combined use of aptamers that bind to different epitopes of a particular target (e.g. treated surface) could provide a greater overall target coverage and/or efficacy across different individuals. Identification of aptamers binding to different epitopes can be achieved by performing a covariance analysis for the change in oligonucleotide frequency during the rounds of SELEX selection as described in Example 3. In certain aspects of the present invention, a consumer product composition comprises at least two different nucleic acid aptamers; wherein said at least two different nucleic acid aptamers have binding affinities for different epitopes of the surface treated with the composition. In another aspect, said at least two different nucleic acid aptamers are selected from the group consisting of SEQ ID NO 1, SEQ ID NO 9, SEQ ID NO 25, SEQ ID NO 112, SEQ ID NO 120, and SEQ ID NO 136.

The aptamers of the current invention can also be formulated in consumer product compositions to effectively deliver active ingredients to surfaces being treated with the compositions.

Methods of Use

The consumer products compositions of the present invention are used to treat surfaces in order to provide various benefits to the treated surfaces. As such, the present invention further relates to a method for treating a surface, wherein the method comprises the step of contacting said surface with a consumer product composition of the present invention.

In one aspect, the methods of the present invention relate to treating surfaces comprising applying the consumer product composition of the present invention to surfaces such as hair, skin (including scalp, dermis, epidermis, and the like), teeth, internal body parts or organs, teeth, gums, tongues, throat soft tissue, microorganisms, fabrics, dishware, hard surfaces (floors, countertops, and the like, such as ceramic material, polymeric material, metallic material, composite material, natural stone material, and the like), tissues or paper towels, and components (e.g. topsheets, absorbent cores, backsheets, and the like) of absorbent articles (e.g. diapers, sanitary napkins, tampons, wipes, incontinence pads, training pants, and the like), to provide benefits such as delivering active ingredients to the treated surface, detecting skin aging markers, detecting melanin concentration in skin, binding skin receptors to inactivate or desensitize, binding bacteria for disease prevention, detection or treatment, detecting microbial contamination or infection, and the like.

The present invention further relates to a method for delivering an active ingredient to a surface, said method comprising the step of contacting said surface with a consumer product composition comprising a surfactant, an active ingredient, and a nucleic acid aptamer comprising at least one oligonucleotide comprising: deoxyribonucleotides, ribonucleotides, derivatives of deoxyribonucleotides, derivatives of ribonucleotides, and mixtures thereof. The nucleic acid aptamer is preferably covalently or non-covalently attached to the active ingredient to facilitate delivery of the active ingredient to the treated surface. The nucleic acid aptamer preferably has a binding affinity to an epitope of the treated surface to facilitate retention of the active ingredient and aptamer on the treated surface.

In another aspect, a method for delivering one or more oral care active ingredients to the oral cavity comprises administering an oral care composition comprising: at least one nucleic acid aptamer and one or more nanomaterials; wherein said at least one nucleic acid aptamer and said one or more nanomaterials are covalently or non-covalently attached; and wherein said at least one nucleic acid aptamer has a binding affinity for an oral cavity component.

In another aspect, a method for delivering one or more oral care active ingredients to the oral cavity comprises administering an oral care composition comprising: a) at least one nucleic acid aptamer; b) one or more nanomaterials; and c) and one or more oral care active ingredients; wherein said at least one nucleic acid aptamer and said one or more nanomaterials are covalently or non-covalently attached; and wherein said at least one nucleic acid aptamer has a binding affinity for an oral cavity component. In another aspect, said one or more oral care active ingredients are covalently or non-covalently attached to said one or more nanomaterials. In yet another aspect, said one or more oral care active ingredients are carried by said one or more nanomaterials.

In certain aspects of the present invention, a method for delivering one or more oral care active ingredients to the oral cavity comprises administering an oral care composition comprising at least one nucleic acid aptamer and one or more oral care active ingredients; wherein said at least one nucleic acid aptamer and said one or more oral care active ingredients are covalently or non-covalently attached; and wherein said at least one nucleic acid aptamer has a binding affinity for an oral cavity component. Examples of the oral conditions these oral care active ingredients address include, but are not limited to, appearance and structural changes to teeth, whitening, stain prevention and removal, stain bleaching, plaque prevention and removal, tartar prevention and removal, cavity prevention and treatment, inflamed and/or bleeding gums, mucosal wounds, lesions, ulcers, aphthous ulcers, cold sores, and tooth abscesses.

In another aspect, said oral cavity component in said method of delivering one or more oral care active ingredients is selected from the group comprising: tooth, enamel, dentin, and any other surfaces in the oral cavity. In another aspect, said oral cavity component is tooth.

In another aspect, a method for delivering one or more oral care active ingredients to the oral cavity comprises administering an oral care composition comprising at least one peptide aptamer and one or more oral care active ingredients; wherein said at least one peptide aptamer and said one or more oral care active ingredients are covalently or non-covalently attached; and wherein said at least one peptide aptamer has a binding affinity for an oral cavity component.

EXAMPLES

Example 1. Aptamer Synthesis

An example of synthesizing aptamers that can be used in consumer product compositions, such as oral care compositions such as dentifrice, is shown below.

Aptamer Preparation:

Aptamers SEQ ID NO 1, SEQ ID NO 9, and SEQ ID NO 25 are synthesized by enzymatic transcription from the corresponding double stranded DNA templates using a mixture of 15 mM 2'-fluoro CTP, 15 mM 2'-fluoro UTP, 5 mM ATP, 5 mM GTP, a mutant T7 polymerase (T7 R&DNA), and other standard reagents are used. The aptamers are then cleaned up with a Zymo RNA cleanup column, following manufacturer's instructions, and eluted on the reaction buffer (e.g. phosphate buffered saline (PBS) with EDTA: 10 mM sodium phosphate, 0.15 M NaCl, 10 mM EDTA, pH 7.2).

Conjugation Reaction:

First, a solution of 4,4'-diamino-2,2'-stilbenedisulfonic acid (0.25 M) and imidazole (0.1 M) in water (pH 6) is prepared. Then, EDC (1-ethyl-3-[3-dimethylaminopropyl] carbodiimide hydrochloride) is weighed in a reaction vial and mixed with an aliquot of an aptamer solution prepared as above. An aliquot of the amine/imidazole solution is added immediately to the reaction vial and vortexed until all the components are dissolved. An additional aliquot of imidazole solution (0.1 M, pH 6) is added to the reaction vial and the reaction mixture is incubated at room temperature for at least 2 hours. Following incubation, the unreacted EDC and its by-products and imidazole are separated from the modified aptamer by dialysis or by using a spin desalting column and a suitable buffer (e.g. 10 mM sodium phosphate, 0.15 M NaCl, 10 mM EDTA, pH 7.2). Additional details about the conjugation protocols are described in "Hermanson G. T. (2008). Bioconjugate Techniques. 2nd Edition. pp. 969-1002, Academic Press, San Diego.", the content of which is incorporated herein by reference.

The produced modified aptamer is conjugated with an active ingredient and can be formulated into a consumer product composition. For example, the produced modified aptamer that is conjugated with 4,4'-diamino-2,2'-stilbenedisulfonic acid at the 5'-end can be formulated in an oral care composition (e.g. dentifrice) to provide teeth whitening benefits when contacted with teeth.

Example 2. Consumer Product Composition

An example of a potential consumer product composition, which is a dentifrice composition, comprising a surfactant and a nucleic acid aptamer of the present invention is shown in the table below. Sample consumer product compositions can be prepared using standard methods known in the art using, e.g., the components listed in the table below.

| Components | Weight % of Composition |
|---|---|
| Sorbitol solution (70%) | 32.577 |
| Sodium hydroxide (50% soln.) | 1.740 |
| Water | QS |
| Saccharin sodium | 0.450 |
| Xanthan gum | 0.300 |
| Sodium fluoride | 0.243 |
| Carboxymethylcellulose | 1.050 |
| Sodium acid pyrophosphate | 3.190 |
| Carbomer | 0.300 |
| Flavor | 1.4 |
| Sodium lauryl sulfate (28% soln.) | 6.000 |
| Mica titanium dioxide | 0.400 |
| Nucleic Acid Aptamer [1] | 0.01-0.1 |
| Silica | 22 |
| Total | 100 |

[1] E.g. the conjugated aptamer of Example 1

Example 3. Aptamer Design

A. Preparation of the Immobilization Field

The immobilization field was prepared by synthesizing a random library of eight nucleotide oligonucleotides with a disulfide group on the 5'-end (immobilization field library) as described elsewhere (PLoS One. 2018 Jan. 5; 13(1): e0190212). In brief, the 8-mer thiolated random oligonucleotide library was dissolved in 50 µL of 1×PBS buffer (pH 7.4) at a final concentration of 10 µM. The surface of a gold coated glass slide with dimensions of 7 mm×10 mm×0.3 mm (Xantec, Germany). was treated with five sequential 10 µL drops of the immobilization field library. The slide was then allowed to incubate for 1 hour in the dark at room temperature in order to facilitate conjugation of the immobilization field library onto the gold surface.

After this incubation period, the immobilization field library was considered to have been conjugated onto the gold surface. The remaining solution was removed, and the surface was allowed to dry at room temperature.

The remaining surface was then blocked with short thiol terminated polyethylene glycol (PEG-SH) with molecular formula: $CH_3O-(CH_2CH_2O)_n-CH_2CH_2SH$ and an average molecular weight of 550 daltons. An aliquot of 50 µL of the PEG-SH solution in 1×PBS buffer at a concentration of 286 µM was applied to the chip and allowed to incubate overnight at room temperature with gentle shaking. This process was repeated in a second blocking step, with an incubation period of 30 minutes at room temperature with gentle shaking.

Following blocking of the chip, the latter was washed with 600 µL of 1×HEPES buffer (10 mM HEPES, pH 7.4, 120 mM NaCl, 5 mM KCl, 5 mM $MgCl_2$) for 5 minutes with shaking at room temperature.

B. Library Preparation

A DNA library of about $10^{15}$ different sequences, containing a random region of 40 nucleotides flanked by two conserved regions, i.e. T7 promoter sequence (SEQ ID NO 223) at the 5'-end (5'-GGGAAGAGAAGGACATATGAT-3') and a 3' reverse primer recognition sequence (SEQ ID NO 224); (5'-TTGACTAGTACATGACCACTT-3'), was transcribed to RNA using a mixture of 3:1 2'-fluoro pyrimidines nucleotides and natural purine nucleotides and a mutant T7 polymerase (T7 R&DNA).

An aliquot of the transcribed selection library comprising about $10^{15}$ RNA sequences was diluted in 50 µL of 1× selection buffer (10 mM cacodylate buffer, 120 mM NaCl, 5 mM KCl, 50 µM $SnF_2$). An equimolar number of oligonucleotides complementary to the conserved regions of the library sequences (T7 promoter primer and 3' reverse primer) or blockers was added and incubated with the selection library in a total volume of 100 µL. This solution was heated for 10 minutes at 45° C. to ensure removal of any secondary or tertiary structures which could interfere with the proper annealing of the blockers to the selection library. The blockers were then allowed to anneal to the selection library by allowing the mixture to equilibrate to room temperature for 15 minutes.

This blocked selection library was then exposed to the immobilization field in five sequential 10 µL drops. The blocked selection library was incubated on the immobilization field for 30 minutes with slow shaking in an incubator at room temperature. The solution remaining on top after this time period was removed and discarded. The chip was washed twice with the addition of 50 µL of selection buffer. The buffer was pipetted over the chip and then discarded.

The blocked selection library sequences which were bound to the immobilization field were recovered from the chip by applying 50 µL of 60% DMSO and incubating for 10 min at room temperature. The solution was removed to a fresh tube, and the process was repeated two more times. The three elution solutions were combined (150 µL in total). The RNA sequences were then cleaned up with a Zymo RNA cleanup column (Zymo Research, Irvine, Calif.), following manufacturer's instructions. The purified selection library was eluted with 35 µL of water and combined with 10 µL of 5× selection buffer and 5 µL of 500 µM $SnF_2$.

C. Aptamer Selection.

A clean unerupted third molar tooth was washed with three successive applications of 1 mL water and dipped into a sample of human saliva collected from several individuals. Saliva was pipetted over regions of the tooth that appeared to not be coated. The 50 µL library solution prepared as described above (section B) was pipetted into a depression on a microscope slide (concavity slides, 3.2 mm thick; United Scientific) and the tooth was placed in this depression. The slide was then placed in a shaking incubator at 50 rpm, 37° C., for 1 hour. The tooth was removed and washed twice with 1 mL each of selection buffer. Then the tooth was placed on a fresh depression slide and 50 µL of 60% DMSO was added to elute bound sequences. This elution process was repeated and the two elution solutions were combined (100 µL in total). The eluted RNA library was cleaned up with a Zymo RNA clean up column, following manufacturer's instructions. The library was reverse transcribed into DNA with Protoscript RT II enzyme and PCR amplified in a two-step process. First, four separate PCR reactions were performed with different numbers of sequential PCR cycles (e.g. 4, 6, 8, and 10 cycles). Then, the products of each of these PCR reactions were analyzed by gel electrophoresis to determine the optimum number of cycles required for amplification, i.e. as high a yield as possible without the appearance of any concatemers of the PCR product. Then, this number of PCR cycles was applied for library amplification to complete the selection round.

The library was split into two aliquots to perform two experiments under the same conditions (Experiment A and Experiment B). The selection process was repeated eleven more times. Dentifrice (Crest Cavity Protection) containing surfactant (sodium lauryl sulfate) was added at a concentration of 0.322% in the selection buffer during selection rounds 6, 9, and 12.

Negative selections against coffee and wine were also performed. During selection rounds 7 and 10, an aliquot of 5 µL of instant coffee was added to the library solution (for a final 1:10 dilution) and the mixture was incubated with the immobilization field for 30 minutes with shaking in an incubator at room temperature. Oligonucleotides with specificity for molecules present in the coffee are not expected to bind the immobilization field. Thus, the solution remaining on top after this time period was removed and discarded. The chip was washed twice with the addition of 50 µL of selection buffer. The buffer was pipetted onto the surface and then discarded. The library sequences which were bound to the immobilization field were recovered from the chip by applying 50 µL of 60% DMSO and incubating for 10 min at room temperature. The solution was removed to a fresh tube, and the process was repeated two more times. The three elution solutions were combined (150 µL in total). The RNA sequences were then cleaned up with a Zymo RNA cleanup column, following manufacturer's instructions. The library was reverse transcribed into DNA with Protoscript RT II enzyme and PCR amplified in a two-step process, as described above, to complete the selection cycle. The same process was performed with wine during selection rounds 8 and 11.

D. Aptamers Sequencing

Figure 2:
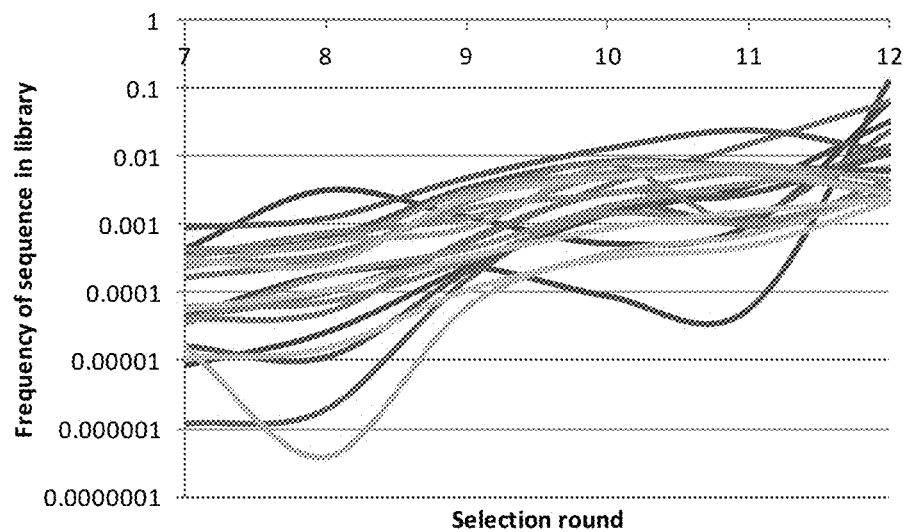
FIG. 2 illustrates the enrichment trajectories of the top twenty sequences in terms of copy number across different selection rounds for Experiment B.

Aliquots of selection rounds 7 to 12 for both experiments were prepared for next generation sequencing (NGS) analysis. A total of more than 23 million sequences were analyzed. The number of sequences captured was much lower for selection rounds 11 and 12 as a function of the increased stringency of selection. One indication that a selection was successful is the observation that the copy number of certain sequences increased over selection rounds (see FIG. 1 and FIG. 2). In the graphs shown in FIGS. 1 and 2, the top 20 sequences based on the frequency on round 12 of the selection process were graphed. For instance, for FIG. 1, the sequences are OC1R-A1 to OC1R-A20 in order from the top line to the bottom line (based on round 12). FIG. 1 shows the enrichment trajectories of the top twenty sequences in terms of copy number across different selection rounds for Experiment A. FIG. 2 shows the enrichment trajectories of the top twenty sequences in terms of copy number across different selection rounds for Experiment B. The top sequences in terms of copy number for every selection experiment are listed in TABLE 1. Interestingly, the top 15 sequences, based on copy number, in selection experiment A were also identified in the top 40 sequences of selection experiment B. Furthermore, the top 2 sequences in both experiments were identical, but in the reverse ranking.

Example 4. RNA Aptamers Binding

DNA oligonucleotides encoding for selected aptamers (OC1R-B1/OC1R-A2, OC1R-B9, and OC1R-B25/OC1R-A9) and one encoding for a negative control aptamer (Neg) were transcribed to RNA using a mixture of 1 mM biotinylated UTP, 15 mM 2'-fluoro CTP, 14 mM 2'-fluoro UTP, 5 mM ATP, 5 mM GTP, a mutant T7 polymerase (T7 R&DNA), and other standard reagents. The modified RNA oligonucleotides were then cleaned up with a Zymo RNA cleanup column, following manufacturer's instructions. An aliquot of 250 µL of 1 µM modified RNA in 1× binding buffer (10 mM cacodylate buffer, 120 mM NaCl, 5 mM KCl, 50 µM $SnF_2$, and 0.322% dentifrice) was placed in the depression of a microscope slide (concavity slides, 3.2 mm thick; United Scientific). Separately, a clean unerupted third molar tooth was washed with water, dried, and coated with human saliva collected fresh from several. The tooth was then placed into the depression of the slide containing the modified RNA and incubated for 30 minutes at room temperature. The tooth was removed from the slide and washed twice with 250 µL of binding buffer.

Figure 3A:
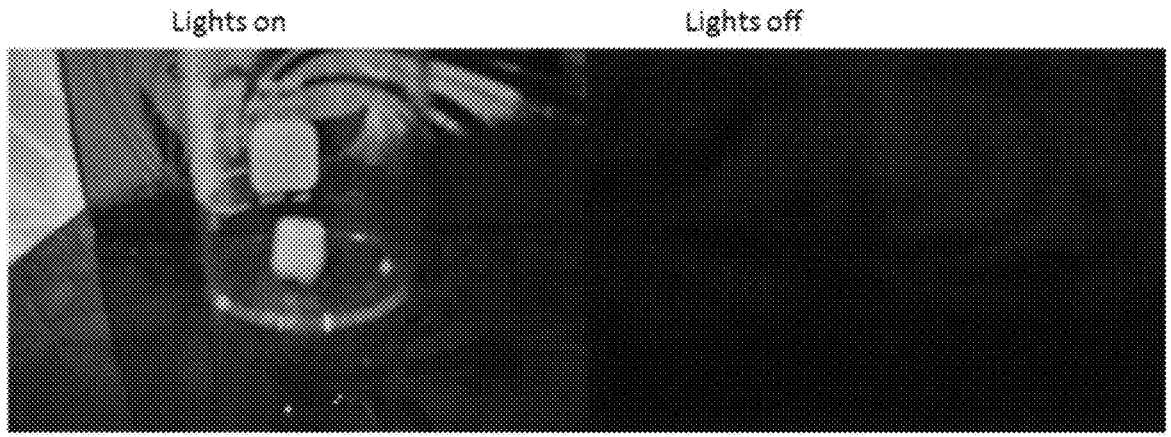
FIG. 3A shows a negative control.
Figure 3B:
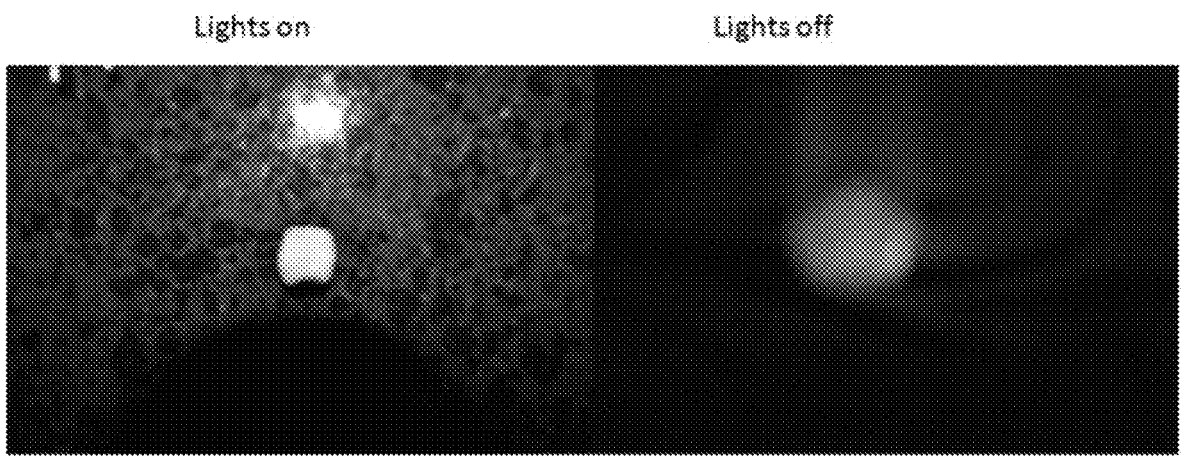
FIG. 3B shows the binding of the aptamer identified as "OC1R-B1" to teeth.
Figure 3C:
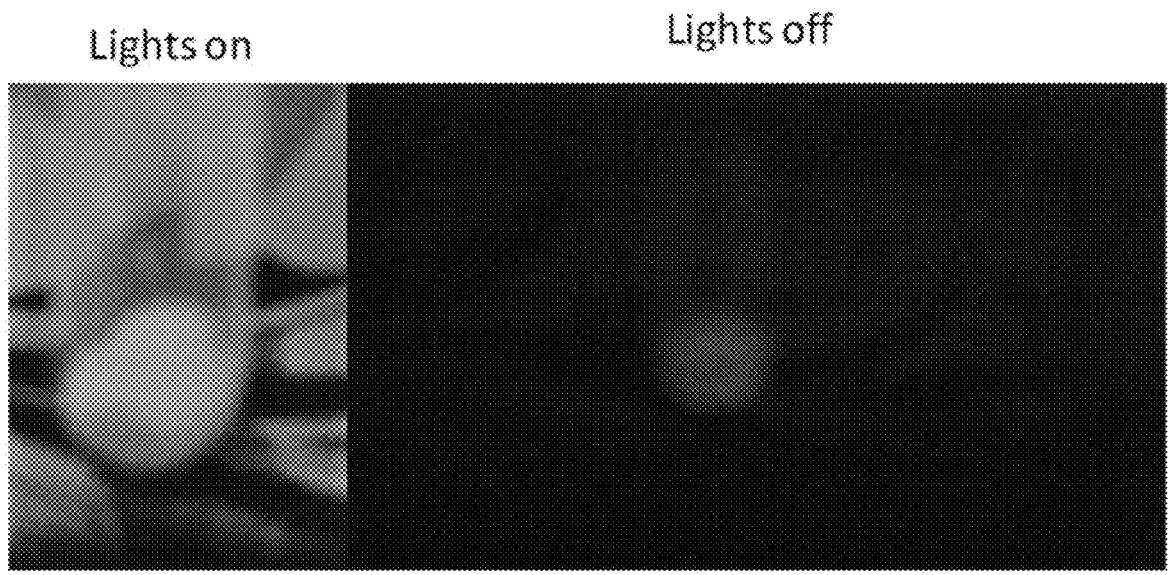
FIG. 3C shows the binding of the aptamer identified as "OC1R-B9" to teeth.
Figure 3D:
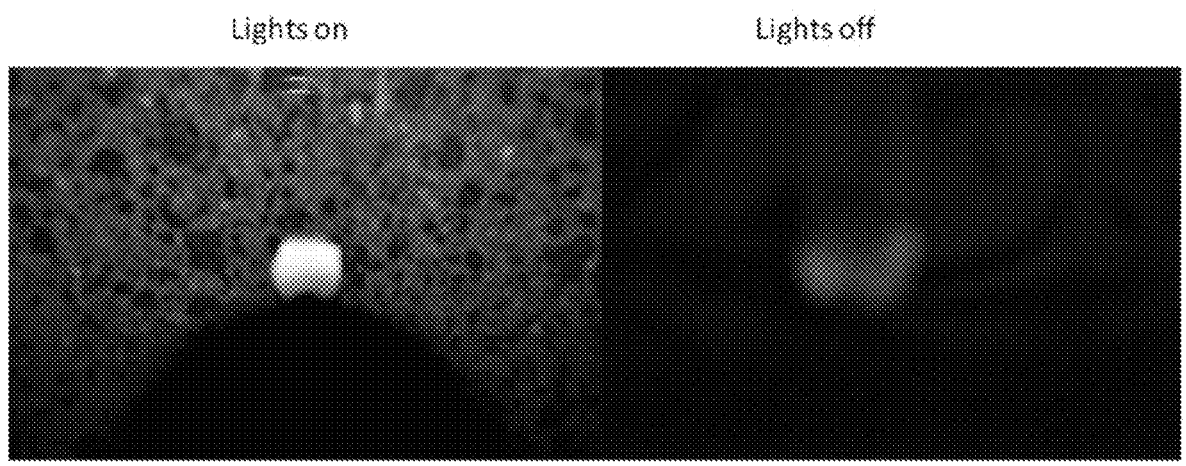
FIG. 3D shows the binding of the aptamer identified as "OC1R-B25/OC1R-A9" to teeth.

A solution of streptavidin-horse radish peroxidase (HRP) in binding buffer was prepared and an aliquot of 250 µL was placed into the depression of a clean slide (concavity slides, 3.2 mm thick; United Scientific). The tooth was also placed into the same depression and incubated for 30 minutes at room temperature. After incubation, the tooth was washed with 2 mL of binding buffer. Finally, to detect aptamer binding, the tooth was immersed into a solution of 10× LumiGLO® (Cell Signaling Technology, Danvers, Mass.) and 10× hydrogen peroxide (50:50 mixture of 20× stocks). Only aptamers that bind to the tooth generated chemoluminescence in darkness (see FIGS. 3A-3D). FIGS. 3A-3D show the binding of different aptamers to teeth as demonstrated by the chemoluminescence of the teeth in darkness. FIG. 3A shows a negative control. FIG. 3B shows the binding of the aptamer identified as "OC1R-B1" to teeth. FIG. 3C shows the binding of the aptamer identified as "OC1R-B9" to teeth. FIG. 3D shows the binding of the aptamer identified as "OC1R-B25/OC1R-A9" to teeth.

Example 5. DNA Aptamers Binding

Figure 4:
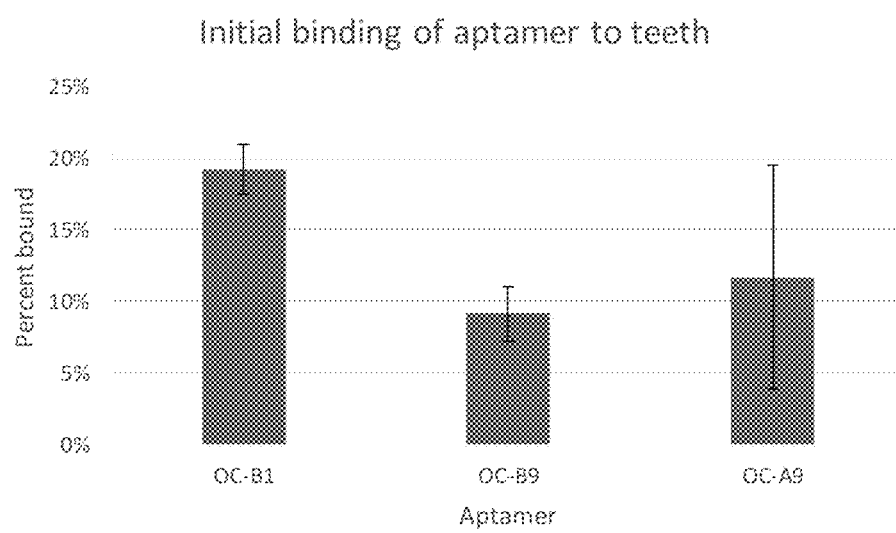
FIG. 4 illustrates the amount of DNA Aptamers bound to teeth.
Figure 5:
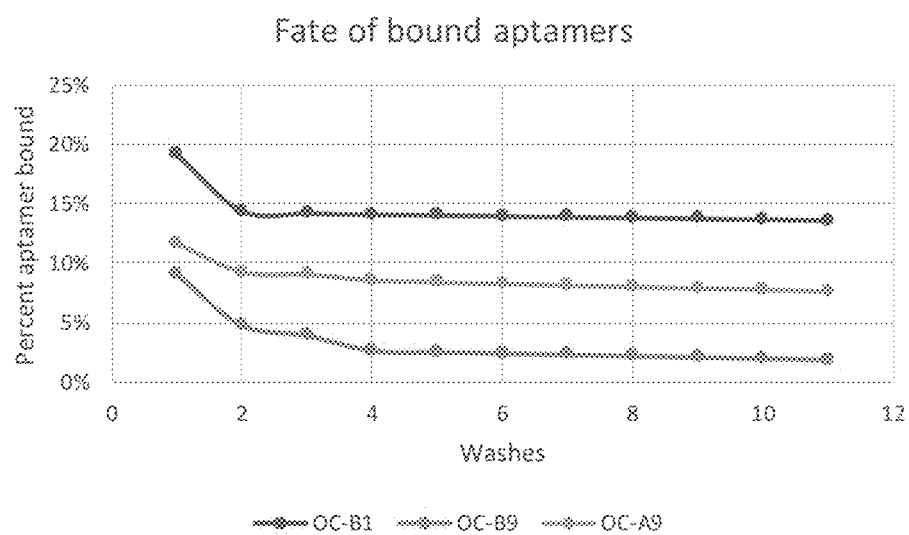
FIG. 5 illustrates the amount of DNA Aptamers bound to teeth after every washing.
Figure 6:
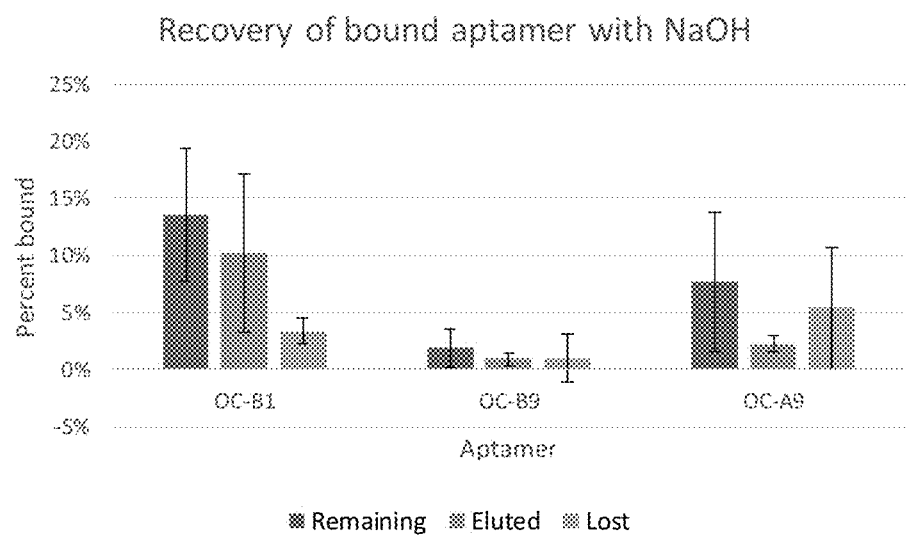
FIG. 6 illustrates the total amount of DNA aptamers bound (remaining), washed (eluted), and unrecovered (lost) from teeth.

Selected DNA aptamers (OC1D-B1/OC1D-A2, OC1D-B9, and OC1D-B25/OC1D-A9) were chemically synthesized with a FAM fluorophore on the 5'end (Eurofins). An aliquot of 250 µL of 1 µM DNA aptamer in 1× binding buffer (10 mM cacodylate buffer, 120 mM NaCl, 5 mM KCl, 50 µM $SnF_2$, and 0.322% toothpaste; pH 7.2) was placed in the depression of a microscope slide (concavity slides, 3.2 mm thick; United Scientific). Separately, a clean unerupted third molar tooth was washed with water, dried, and coated with human saliva collected fresh from several individuals. The tooth was then placed into the depression of the slide containing the DNA aptamer and incubated for 20 minutes at room temperature. The amount of aptamer bound was determined by measuring the fluorescence remaining in the solution after the tooth was removed (see FIG. 4). The tooth was removed from the slide and washed several times with 250 µL of neutral binding buffer. The fluorescence of each wash solution was measured (see FIG. 5). Bound aptamers were recovered by washing the teeth with two aliquots of 250 mM NaOH. The fluorescence of each elution solution was also measured (see FIG. 6). Not all the aptamer incubated with the teeth was recovered probably due to very strong binding or adsorption inside the teeth.

Given that we have shown that the DNA version of aptamers OC1R-B1/OC1R-A2, OC1R-B9, and OC1R-B25/OC1R-A9 also bind effectively to teeth, it stands to reason that the conclusions arrived at within this example would apply to the DNA versions of the remaining selected aptamers (SEQ ID NO: 112 to SEQ ID NO: 222), included herein as part of the invention and listed in TABLE 2.

TABLE 1

List of top sequences from selection experiments A and B. All the pyrimidine nucleotides are fluorinated at the 2' position of the pentose group.

| SEQ ID NO | Name | Total Sequence | Copy Number |
|---|---|---|---|
| 1 | OC1R-B1 or OC1R-A2 | GGGAAGAGAAGGACAUAUGAUUCAUGUGAGAUGA UGUGUGUUCCUAGUUUUAUCUUGCUCUUUGACUA GUACAUGACCACUU | 16160 |
| 2 | OC1R-B2 or OC1R-A1 | GGGAAGAGAAGGACAUAUGAUUAGGCUAACUGUU CAGGGAUUUGAUAUGCAUGAGGAGCACUUGACUA GUACAUGACCACUU | 7945 |
| 3 | OC1R-B3 or OC1R-A19 | GGGAAGAGAAGGACAUAUGAUCCGCUCUAAAGUA CCAACCGCGGGAGCUAAAUGCAAGCCGUUGACUAG UACAUGACCACUU | 7939 |
| 4 | OC1R-B4 | GGGAAGAGAAGGACAUAUGAUUGUGUCAGGCUCU AGAGUCUAGACGGCCGGGGUCCCGGAUUGACUA GUACAUGACCACUU | 4041 |
| 5 | OC1R-B5 | GGGAAGAGAAGGACAUAUGAUCCUUAUGUCUAGC GGCCUUACGCGAUUAGUGGCGUUUUGUUUGACUA GUACAUGACCACUU | 2867 |
| 6 | OC1R-B6 | GGGAAGAGAAGGACAUAUGAUCUUUAUGUAUUAU CAGUCAUACCGGACGCAGCCCGCUGGAUUGACUAG UACAUGACCACUU | 1841 |
| 7 | OC1R-B7 or OC1R-A3 | GGGAAGAGAAGGACAUAUGAUUGUGUUAUUACAC UUCGUGAUUUUCCUUGCUUUUCUAUUUUUGACUA GUACAUGACCACUU | 1464 |
| 8 | OC1R-B8 | GGGAAGAGAAGGACAUAUGAUCCAACAUCUAAAG UACUGGUCGCCUAGGGAGACUGUUCGGUUGACUA GUACAUGACCACUU | 1373 |
| 9 | OC1R-B9 | GGGAAGAGAAGGACAUAUGAUGCUAUAUUCGCAA AAGCAGGCUGAGUGCGGCAGGCGCGUGUUGACUA GUACAUGACCACUU | 851 |
| 10 | OC1R-B10 | GGGAAGAGAAGGACAUAUGAUUCAUUCAUUCGCA ACACAAUUGUAUUCGCAUCUGCGAUUUUUGACUA GUACAUGACCACUU | 759 |
| 11 | OC1R-B11 or OC1R-A11 | GGGAAGAGAAGGACAUAUGAUCUUUCUCUUUUCU AAUAUUUAAUUUAUUGGGUACCAAUUUUUGACUA GUACAUGACCACUU | 561 |
| 12 | OC1R-B12 or OC1R-A7 | GGGAAGAGAAGGACAUAUGAUCUUUGUUUCGCAU ACGUUUUCUUUUUCUCUCUUCUUAUUUUUGACUA GUACAUGACCACUU | 425 |
| 13 | OC1R-B13 or OC1R-A5 | GGGAAGAGAAGGACAUAUGAUUAUUCUGUUCUUC AAAAAUCUUUUAGCGUAUACGCUAUUUUUGACUA GUACAUGACCACUU | 402 |

TABLE 1-continued

List of top sequences from selection experiments A and B. All the pyrimidine nucleotides are fluorinated at the 2' position of the pentose group.

| SEQ ID NO | Name | Total Sequence | Copy Number |
|---|---|---|---|
| 14 | OC1R-B14 | GGGAAGAGAAGGACAUAUGAUUUCCUUAUGUUCG GUCAACAGGGACUGCUGCAGCACCGGCUUGACUAG UACAUGACCACUU | 396 |
| 15 | OC1R-B15 | GGGAAGAGAAGGACAUAUGAUUAAGCGCACUCAA CAGGGUCUAUGAUCCGCGCCGAUCAUGUUGACUAG UACAUGACCACUU | 371 |
| 16 | OC1R-B16 or OC1R-A15 | GGGAAGAGAAGGACAUAUGAUCCGCUUUCCAUUG AGAUUAUAAGCUGUUAGAGACUUAUUUUUGACUA GUACAUGACCACUU | 357 |
| 17 | OC1R-B17 or OC1R-A8 | GGGAAGAGAAGGACAUAUGAUUUUCGAAACGUUU CUUUCAAGUUCUUAAUCAUUCCCAUUUUUGACUA GUACAUGACCACUU | 353 |
| 18 | OC1R-B18 | GGGAAGAGAAGGACAUAUGAUCAUUAGAUGCGCA GUUCGAAGCCGGUACAGCUGGCGCGCGUUGACUAG UACAUGACCACUU | 297 |
| 19 | OC1R-B19 | GGGAAGAGAAGGACAUAUGAUAAAGAAUAACCUU AAAAUAACACCACCGCCUCACAGCAUAUUGACUAG UACAUGACCACUU | 290 |
| 20 | OC1R-B20 or OC1R-A6 | GGGAAGAGAAGGACAUAUGAUAAAUUGAUCUAUU CUUUUCGGUGCUAUUUAUCUUCCAUUUUUGACUA GUACAUGACCACUU | 282 |
| 21 | OC1R-B21 | GGGAAGAGAAGGACAUAUGAUCUACUCGCGCGGC GGACAAAAGCGCAACCCAGCACCCAUGUUGACUAG UACAUGACCACUU | 282 |
| 22 | OC1R-B22 or OC1R-A10 | GGGAAGAGAAGGACAUAUGAUUCUUAGUUUGUAA UUACUUUUCCUUCCUUUUAUUCUAUUUUUGACUA GUACAUGACCACUU | 255 |
| 23 | OC1R-B23 | GGGAAGAGAAGGACAUAUGAUAACCCGCGCAGAC UUACAAGCGCGCAAAAAAAGGGUACGUUUGACUA GUACAUGACCACUU | 227 |
| 24 | OC1R-B24 or OC1R-A23 | GGGAAGAGAAGGACAUAUGAUAUUCCUUUAUGCC GCAUCAUUUUAUUGUUUAUGACAAUUUUUGACUA GUACAUGACCACUU | 209 |
| 25 | OC1R-B25 or OC1R-A9 | GGGAAGAGAAGGACAUAUGAUAUUUCGUACUACU UUUCUUCCAAGCUUCAAUCGCCCAUUUUUGACUAG UACAUGACCACUU | 209 |
| 26 | OC1R-B26 or OC1R-A24 | GGGAAGAGAAGGACAUAUGAUUCACUCAUUCGCA ACACAAUUGUAUUCGCAUCUGCGAUUUUUGACUA GUACAUGACCACUU | 198 |
| 27 | OC1R-B27 or OC1R-A12 | GGGAAGAGAAGGACAUAUGAUAUUAUUCCACAG UUCCUUUAUCCACACAUCUUCUCAUUUUUGACUAG UACAUGACCACUU | 190 |
| 28 | OC1R-B28 | GGGAAGAGAAGGACAUAUGAUAAACUCGUUAUCU AUUCGUUUAUUUGCAUCUCUUUCAUUUUUGACUA GUACAUGACCACUU | 187 |
| 29 | OC1R-B29 | GGGAAGAGAAGGACAUAUGAUCCAACCUCUAAAG UACUGGUCGCCUAGGGAGACUGUUCGGUUGACUA GUACAUGACCACUU | 185 |
| 30 | OC1R-B30 or OC1R-A13 | GGGAAGAGAAGGACAUAUGAUUUCCUUUUUGCUA UUUCCGUUAAUGUAAACUCUCCUAUUUUUGACUA GUACAUGACCACUU | 179 |
| 31 | OC1R-B31 | GGGAAGAGAAGGACAUAUGAUCCUUAUGGCCUAG UAGGGAUCCGGGCGCCGACCAGCGCGAUUGACUAG UACAUGACCACUU | 167 |
| 32 | OC1R-B32 or OC1R-A18 | GGGAAGAGAAGGACAUAUGAUCGUCUGUCUUCUU CGAAUACGUUUUGGGCUAAGCCCAUUUUUGACUA GUACAUGACCACUU | 153 |
| 33 | OC1R-B33 | GGGAAGAGAAGGACAUAUGAUUCAACCAAACUGC CGACGACCGAGGUAUGUCCUUAUGUACUUGACUA GUACAUGACCACUU | 143 |
| 34 | OC1R-B34 | GGGAAGAGAAGGACAUAUGAUUACGGGUCUGAGC AAAAGCGAAGGAAGCAGGCGCAGGGAUUUGACUA GUACAUGACCACUU | 142 |
| 35 | OC1R-B35 or OC1R-A4 | GGGAAGAGAAGGACAUAUGAUUCUCUCAUUCGCA ACACAAUUGUAUUCGCAUCUGCGAUUUUUGACUA GUACAUGACCACUU | 134 |
| 36 | OC1R-B36 | GGGAAGAGAAGGACAUAUGAUGCUCUAAAGUACU AAGCGUUUGCGCCGAUGCCCGGACCGCUUGACUAG UACAUGACCACUU | 127 |
| 37 | OC1R-B37 | GGGAAGAGAAGGACAUAUGAUACUUCAUUAAUGU GAGGCCGUCAGGGGGCAACCUUCGAGCUUGACUAG UACAUGACCACUU | 126 |
| 38 | OC1R-B38 | GGGAAGAGAAGGACAUAUGAUUCCUUAUUCUUGU UACUACUUUCUUUUCCUAUUUUUUUCUUUGACUA GUACAUGACCACUU | 126 |
| 39 | OC1R-B39 or OC1R-A14 | GGGAAGAGAAGGACAUAUGAUCGUUAUUUUCAUU UUCUUGUUCCCCAUAUGCCCAGGCGCAUUGACUAG UACAUGACCACUU | 125 |
| 40 | OC1R-B40 | GGGAAGAGAAGGACAUAUGAUACCAGCGGCUAG AAACGUACAGCUCGCCUGUAACGCCUGUUGACUAG UACAUGACCACUU | 120 |
| 41 | OC1R-B41 | GGGAAGAGAAGGACAUAUGAUCGAUAUGGGUGCG GGAAUGUACGUUCACCGAAUAUGCUCCUUGACUA GUACAUGACCACUU | 107 |

TABLE 1-continued

List of top sequences from selection experiments A and B. All the pyrimidine nucleotides are fluorinated at the 2' position of the pentose group.

| SEQ ID NO | Name | Total Sequence | Copy Number |
|---|---|---|---|
| 42 | OC1R-B42 | GGGAAGAGAAGGACAUAUGAUUAACAGUGCGUAG UCAUAUCGAAUGUUUAUCUUCCUAUUUUUGACUA GUACAUGACCACUU | 95 |
| 43 | OC1R-B43 | GGGAAGAGAAGGACAUAUGAUCAGACUCUCGCCC AAUUCGCAAGGCGUUGCAUUGCGAUUUUUGACUA GUACAUGACCACUU | 94 |
| 44 | OC1R-B44 | GGGAAGAGAAGGACAUAUGAUUUCCAACUCUCCA CGAGAGCAUGGGUCGAAUGACUCAUUUUUGACUA GUACAUGACCACUU | 88 |
| 45 | OC1R-B45 | GGGAAGAGAAGGACAUAUGAUGCAUCGCGCGUCA CUCAACUCGUGAUUACCGAGGGCGCCGUUGACUAG UACAUGACCACUU | 86 |
| 46 | OC1R-B46 | GGGAAGAGAAGGACAUAUGAUCUGAAUCUUUCCG CAGCCCUGUCCUUUUAAAGACAGGUUUUUGACUA GUACAUGACCACUU | 82 |
| 47 | OC1R-B47 | GGGAAGAGAAGGACAUAUGAUUUUGUUACUUACU UCGUCUAUCUUCUGUUGCACACAGUUUUUGACUA GUACAUGACCACUU | 70 |
| 48 | OC1R-B48 | GGGAAGAGAAGGACAUAUGAUUCAAAUCUUCAGC GAUAAUGGCACAAUUUCCGCGCCAUUUUUGACUA GUACAUGACCACUU | 69 |
| 49 | OC1R-B49 | GGGAAGAGAAGGACAUAUGAUUUAUGUGAGAUGA UGUGUGUUCCUAGUUUUAUCUUGCUCUUUGACUA GUACAUGACCACUU | 67 |
| 50 | OC1R-B50 | GGGAAGAGAAGGACAUAUGAUCCACUUUUCCAUU AACUGUUGCGGGCAAGUAGCACCGUUUUUGACUA GUACAUGACCACUU | 62 |
| 51 | OC1R-B51 | GGGAAGAGAAGGACAUAUGAUAGAGAAGACCAUU CGGAAAGAGCUGCGUGUCCUUAUGUACUUGACUA GUACAUGACCACUU | 59 |
| 52 | OC1R-B52 | GGGAAGAGAAGGACAUAUGAUUCUUAUGUAGCAA GCAAAAUGUGCCGCCGAGCCGACGCCAUUGACUAG UACAUGACCACUU | 58 |
| 53 | OC1R-B53 | GGGAAGAGAAGGACAUAUGAUAAGCGCAUAAUAA GCCAGCCAGUUCUUGGCGCGCGGGGUAUUGACUAG UACAUGACCACUU | 56 |
| 54 | OC1R-B54 | GGGAAGAGAAGGACAUAUGAUUAGUCCGCAUUUC UAUUUUCUAUAUGGCUUACUGCCAUUUUUGACUA GUACAUGACCACUU | 56 |
| 55 | OC1R-B55 | GGGAAGAGAAGGACAUAUGAUAUAAAGAACACGC AAAACCACCCGGACACCCGGUGCCGUGUUGACUAG UACAUGACCACUU | 44 |
| 56 | OC1R-B56 | GGGAAGAGAAGGACAUAUGAUACACAGGCGGUGG AGCCGAAGGGCACCGGGACAAACCGACUUGACUAG UACAUGACCACUU | 42 |
| 57 | OC1R-B57 | GGGAAGAGAAGGACAUAUGAUAGUUCCGGCGCAG CAGCGUCCUCACGUUUUACGUGCCCCAUUGACUA GUACAUGACCACUU | 39 |
| 58 | OC1R-B58 | GGGAAGAGAAGGACAUAUGAUGACCGUCGCGAUC GUUUAUAAUGUUCUGGAUCUUUCAUUUUUGACUA GUACAUGACCACUU | 39 |
| 59 | OC1R-B59 | GGGAAGAGAAGGACAUAUGAUAAGUGGGGCCCCG ACGACUUUCCUUCCUCUCUUCCGGCAUUGACUAG UACAUGACCACUU | 37 |
| 60 | OC1R-B60 | GGGAAGAGAAGGACAUAUGAUAUCAACAUACCAA AAUGUCAUUUCCAAUCUUUUCCCAUUUUUGACUA GUACAUGACCACUU | 37 |
| 61 | OC1R-B61 | GGGAAGAGAAGGACAUAUGAUAGCGAACAAACAA GGGUGCCCAGGCCCCCUUCGCACAUCGUUGACUAG UACAUGACCACUU | 36 |
| 62 | OC1R-B62 | GGGAAGAGAAGGACAUAUGAUCCUCUGUAACGCA AAGUCAAGUCGCGCAAGGCCGCCCGCGUUGACUAG UACAUGACCACUU | 35 |
| 63 | OC1R-B63 | GGGAAGAGAAGGACAUAUGAUCUUCAUCUGCGAU UACGGUACACUUUAGUGUAUCGUUUUUUUGACUA GUACAUGACCACUU | 35 |
| 64 | OC1R-B64 | GGGAAGAGAAGGACAUAUGAUGCCUAUGUGCUAG AUGCAGCAGCAACCGCCGGCGACUGGAUUGACUA GUACAUGACCACUU | 35 |
| 65 | OC1R-B65 | GGGAAGAGAAGGACAUAUGAUCCGCGCCCUAACCU UCUGACCAAGCUUCCCUGGCACUUGGUUGACUAGU ACAUGACCACUU | 33 |
| 66 | OC1R-B66 | GGGAAGAGAAGGACAUAUGAUCCUUAUGUAUUAU CAGUCAUACCGGACGCAGCCCGCUGGAUUGACUAG UACAUGACCACUU | 33 |
| 67 | OC1R-B67 | GGGAAGAGAAGGACAUAUGAUCUAAUCUAUACUG GCUGCUAACGCUUUUUCUUUUCCAUUUUUGACUA GUACAUGACCACUU | 33 |
| 68 | OC1R-B68 | GGGAAGAGAAGGACAUAUGAUCAGUUUACGCGGA GUCGUUUGUGUCCAUUUCUUCUCAUUUUUGACUA GUACAUGACCACUU | 32 |
| 69 | OC1R-B69 | GGGAAGAGAAGGACAUAUGAUUCACGUGAGAUGA UGUGUGUUCCUAGUUUUAUCUUGCUCUUUGACUA GUACAUGACCACUU | 32 |
| 70 | OC1R-B70 | GGGAAGAGAAGGACAUAUGAUUCCUUGUGUACCG CUCCGAAUGUGCUCCAGCGCGCCUCGUUGACUAG UACAUGACCACUU | 32 |
| 71 | OC1R-B71 | GGGAAGAGAAGGACAUAUGAUAAGCCGGCCCGGG AACAUGUCACGCGCGCGCAAAGUAGUUGACUAG UACAUGACCACUU | 31 |
| 72 | OC1R-B72 | GGGAAGAGAAGGACAUAUGAUCCUGGAUUUCCGA AAUUAGAGUGCCGUUUCGUUACGGUUUUUGACUA GUACAUGACCACUU | 31 |
| 73 | OC1R-B73 | GGGAAGAGAAGGACAUAUGAUCGUGUCAUCCGCA CAAGGAGGCCUGCAUGGCAGGGACACGUUGACUA GUACAUGACCACUU | 31 |
| 74 | OC1R-B74 | GGGAAGAGAAGGACAUAUGAUGAGUAGACUUUUU GUAUCAUUUUUUUAUCGUAAGAUAUUUUUGACUA GUACAUGACCACUU | 31 |
| 75 | OC1R-B75 | GGGAAGAGAAGGACAUAUGAUCCAUGUGAGAUGA UGUGUGUUCCUAGUUUUAUCUUGCUCUUUGACUA GUACAUGACCACUU | 30 |

TABLE 1-continued

List of top sequences from selection experiments A and B. All the pyrimidine nucleotides are fluorinated at the 2' position of the pentose group.

| SEQ ID NO | Name | Total Sequence | Copy Number |
|---|---|---|---|
| 76 | OC1R-B76 | GGGAAGAGAAGGACAUAUGAUCUUUGCUCUAGAG UGUAGUCUAUGAGGGACAAGGUAGCCAUUGACUA GUACAUGACCACUU | 29 |
| 77 | OC1R-B77 | GGGAAGAGAAGGACAUAUGAUGUUGGUUUUCUUU CUCUUUCUUUUCUUUCUCUUUCUAUUUUUGACUA GUACAUGACCACUU | 29 |
| 78 | OC1R-B78 | GGGAAGAGAAGGACAUAUGAUCAAUCGGGCGGGG GUAAGAGGCGUGCGCAGCGUGGAGGUGUUGACUA GUACAUGACCACUU | 28 |
| 79 | OC1R-B79 | GGGAAGAGAAGGACAUAUGAUCACCGUGGUGCGC AAAGCCGCAACGAGAACUGCGGAAUCGUUGACUA GUACAUGACCACUU | 27 |
| 80 | OC1R-B80 | GGGAAGAGAAGGACAUAUGAUUGCUUUAAGUCUU UUUAUCAUUUUGUUUCCUUCAUUUUUUUUGACUA GUACAUGACCACUU | 26 |
| 81 | OC1R-B81 | GGGAAGAGAAGGACAUAUGAUCGACUAGUUAUAC UGCAAAGGCUAUAAGCGCGAGCGCGCGUUGACUA GUACAUGACCACUU | 25 |
| 82 | OC1R-B82 | GGGAAGAGAAGGACAUAUGAUGAGUAAUAGAUGG CGUACACAAAUCGGAUACGACGAGCGCUUGACUAG UACAUGACCACUU | 25 |
| 83 | OC1R-B83 | GGGAAGAGAAGGACAUAUGAUUUUCGCUUCAAGA UUCCCAACGCCUUGUAAGUCAAGGUUUUGACUA GUACAUGACCACUU | 25 |
| 84 | OC1R-B84 | GGGAAGAGAAGGACAUAUGAUGUGUGAGAUGAGC CCCUGGACCAGACGCACGCUCGCACUGUUGACUAG UACAUGACCACUU | 24 |
| 85 | OC1R-B85 | GGGAAGAGAAGGACAUAUGAUCAGGAUGCGGCGC CGGUAAUUGACUUCCCCCUACGUAGGAUUGACUAG UACAUGACCACUU | 23 |
| 86 | OC1R-B86 | GGGAAGAGAAGGACAUAUGAUCAGGGACCCGGCC GGUGCAUCUCCUUCUUUAGCGUACGCCUUGACUAG UACAUGACCACUU | 22 |
| 87 | OC1R-B87 | GGGAAGAGAAGGACAUAUGAUCUGCUCUAAAGUA CCAACCGCGGGAGCUAAAUGCAAGCCGUUGACUAG UACAUGACCACUU | 22 |
| 88 | OC1R-B88 | GGGAAGAGAAGGACAUAUGAUGAUUGCCAUGCAU UAGGGGGGACGCGCGCGAAAGGGAGAUUGACUA GUACAUGACCACUU | 22 |
| 89 | OC1R-B89 | GGGAAGAGAAGGACAUAUGAUUCGCUCUAAAGUA CCAACCGCGGGAGCUAAAUGCAAGCCGUUGACUAG UACAUGACCACUU | 22 |
| 90 | OC1R-B90 | GGGAAGAGAAGGACAUAUGAUAAAAAACCGGGGU UCUUAAUUUUCAUUGUUCGUCGUACUUUUGACUA GUACAUGACCACUU | 21 |
| 91 | OC1R-B91 | GGGAAGAGAAGGACAUAUGAUAACCCAUUGGUGA AUCGCAACCACAGCCAGCCCGGCGCGAUUGACUA GUACAUGACCACUU | 21 |
| 92 | OC1R-B92 | GGGAAGAGAAGGACAUAUGAUCGAAGUGAGGGA UCGCGCGGGGUGCACCUAAAUAUGGGAUUGACUA GUACAUGACCACUU | 21 |
| 93 | OC1R-B93 | GGGAAGAGAAGGACAUAUGAUAGCCUUAUGUACU AUAGAAGUCAGCUAUCCGCCGCACAAUUUGACUAG UACAUGACCACUU | 20 |
| 94 | OC1R-B94 | GGGAAGAGAAGGACAUAUGAUCGUUGUUUUUCCC AAAGCUCGUUAGCAUUCAUUCCUAUUUUUGACUA GUACAUGACCACUU | 20 |
| 95 | OC1R-B95 | GGGAAGAGAAGGACAUAUGAUGAUCAUCAGCGGA AGCACGAAACGCCACGGGCCGCGGCAUUGACUAG UACAUGACCACUU | 20 |
| 96 | OC1R-B96 | GGGAAGAGAAGGACAUAUGAUUCCUUCCUAUUGA CAAUGCGCCCGGGCCUCUUCAAUUGUAUUGACUAG UACAUGACCACUU | 20 |
| 97 | OC1R-B97 | GGGAAGAGAAGGACAUAUGAUAGUUGCCGCGCGG CGCAAGAUUGGAGAGUCCCGGGCUGUAUUGACUA GUACAUGACCACUU | 18 |
| 98 | OC1R-B98 | GGGAAGAGAAGGACAUAUGAUCAUAAGUUCGUUC AUUCCGUUAACACGCGUAUGGCGUUUUUUGACUA GUACAUGACCACUU | 18 |
| 99 | OC1R-B99 | GGGAAGAGAAGGACAUAUGAUCCUUUGUCUCCAA AUCUUAGGACUGAAUGAGUGCCUAUUUUUGACUA GUACAUGACCACUU | 18 |
| 100 | OC1R-B100 | GGGAAGAGAAGGACAUAUGAUCUUCUUUGAGAAU UCUCUUUUUACAAUUCCGGCGCCGUGAUUGACUAG UACAUGACCACUU | 18 |
| 101 | OC1R-A16 | GGGAAGAGAAGGACAUAUGAUUAGGCUAACUGUU UAGGGAUUUGAUAUGCAUGAGGAGCACUUGACUA GUACAUGACCACUU | 3130 |
| 102 | OC1R-A17 | GGGAAGAGAAGGACAUAUGAUCGUCUGUCUUCUU CGAAUACGUUUUGGGCUAAGCCCAUUUUUGACUA GUACAUGACCACUU | 2970 |
| 103 | OC1R-A20 | GGGAAGAGAAGGACAUAUGAUUAGGCUAACUGCU CAGGGAUUUGAUAUGCAUGAGGAGCACUUGACUA GUACAUGACCACUU | 2753 |
| 104 | OC1R-A21 | GGGAAGAGAAGGACAUAUGAUUAGGCUAACUGUU CAGGGACUUGAUAUGCAUGAGGAGCACUUGACUA GUACAUGACCACUU | 2642 |
| 105 | OC1R-A22 | GGGAAGAGAAGGACAUAUGAUUAGGCUCACUGUU CAGGGAUUUGAUAUGCAUGAGGAGCACUUGACUA GUACAUGACCACUU | 2627 |
| 106 | OC1R-A25 | GGGAAGAGAAGGACAUAUGAUUAGGCUAACUGUU CAGGGAUUUGAUAUGCAUGGGGAGCACUUGACUA GUACAUGACCACUU | 2250 |
| 107 | OC1R-A26 | GGGAAGAGAAGGACAUAUGAUUUCUUCCUAUUGA CGAUGCGCCCGGGCCUCUUCAAUUGUAUUGACUAG UACAUGACCACUU | 2195 |
| 108 | OC1R-A27 | GGGAAGAGAAGGACAUAUGAUUAGGCUAACUGUU CGGGGAUUUGAUAUGCAUGAGGAGCACUUGACUA GUACAUGACCACUU | 2156 |
| 109 | OC1R-A28 | GGGAAGAGAAGGACAUAUGAUUAGGCUAACUGUU CAGGGAUUUGAUAUGCACGAGGAGCACUUGACUA GUACAUGACCACUU | 2074 |

TABLE 1-continued

List of top sequences from selection experiments A and B. All the pyrimidine nucleotides are fluorinated at the 2' position of the pentose group.

| SEQ ID NO | Name | Total Sequence | Copy Number |
|---|---|---|---|
| 110 | OC1R-A29 | GGGAAGAGAAGGACAUAUGAUUAGGUUAACUGUU CAGGGAUUUGAUAUGCAUGAGGAGCACUUGACUA GUACAUGACCACUU | 2042 |
| 111 | OC1R-A30 | GGGAAGAGAAGGACAUAUGAUUAGGCUAACUGUU CAGGGAUUUGAUGUGCAUGAGGAGCACUUGACUA GUACAUGACCACUU | 2031 |

TABLE 2

List of deoxyribonucleotides aptamers based on the top sequences from selection experiments A and B.

| SEQ ID NO | Name | Total Sequence |
|---|---|---|
| 112 | OC1D-B1 or OC1D-A2 | GGGAAGAGAAGGACATATGATTCATGTGAGATGATGTGTGTTCCTAG TTTTATCTTGCTCTTTGACTAGTACATGACCACTT |
| 113 | OC1D-B2 or OC1D-A1 | GGGAAGAGAAGGACATATGATTAGGCTAACTGTTCAGGGATTTGATA TGCATGAGGAGCACTTGACTAGTACATGACCACTT |
| 114 | OC1D-B3 or OC1D-A19 | GGGAAGAGAAGGACATATGATCCGCTCTAAAGTACCAACCGCGGGA GCTAAATGCAAGCCGTTGACTAGTACATGACCACTT |
| 115 | OC1D-B4 | GGGAAGAGAAGGACATATGATTGTGTCAGGCTCTAGAGTCTAGACGG CCGGGGTCCCGGATTTGACTAGTACATGACCACTT |
| 116 | OC1D-B5 | GGGAAGAGAAGGACATATGATCCTTATGTCTAGCGGCCTTACGCGAT TAGTGGCGTTTTGTTTGACTAGTACATGACCACTT |
| 117 | OC1D-B6 | GGGAAGAGAAGGACATATGATCTTTATGTATTATCAGTCATACCGGA CGCAGCCCGCTGGATTGACTAGTACATGACCACTT |
| 118 | OC1D-B7 or OC1D-A3 | GGGAAGAGAAGGACATATGATTGTGTTATTACACTTCGTGATTTTCCT TGCTTTTCTATTTTTGACTAGTACATGACCACTT |
| 119 | OC1D-B8 | GGGAAGAGAAGGACATATGATCCAACATCTAAAGTACTGGTCGCCTA GGGAGACTGTTCGGTTGACTAGTACATGACCACTT |
| 120 | OC1D-B9 | GGGAAGAGAAGGACATATGATGCTATATTCGCAAAAGCAGGCTGAG TGCGGCAGGCGCGTGTTGACTAGTACATGACCACTT |
| 121 | OC1D-B10 | GGGAAGAGAAGGACATATGATTCATTCATTCGCAACACAATTGTATT CGCATCTGCGATTTTGACTAGTACATGACCACTT |
| 122 | OC1D-B11 or OC1D-A11 | GGGAAGAGAAGGACATATGATCTTTCTCTTTTCTAATATTTAATTTAT TGGGTACCAATTTTTGACTAGTACATGACCACTT |
| 123 | OC1D-B12 or OC1D-A7 | GGGAAGAGAAGGACATATGATCTTTGTTTCGCATACGTTTTCTTTTTC TCTCTTCTTATTTTTGACTAGTACATGACCACTT |
| 124 | OC1D-B13 or OC1D-A5 | GGGAAGAGAAGGACATATGATTATTCTGTTCTTCAAAAATCTTTTAG CGTATACGCTATTTTTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 125 | OC1D-B14 | GGGAAGAGAAGGACATATGATTTCCTTATGTTCGGTCAACAGGGACT GCTGCAGCACCGGCTTGACTAGTACATGACCACTT |
| 126 | OC1D-B15 | GGGAAGAGAAGGACATATGATTAAGCGCACTCAACAGGGTCTATGA TCCGCGCCGATCATGTTGACTAGTACATGACCACTT |
| 127 | OC1D-B16 or OC1D-A15 | GGGAAGAGAAGGACATATGATCCGCTTTCCATTGAGATTATAAGCTG TTAGAGACTTATTTTTGACTAGTACATGACCACTT |
| 128 | OC1D-B17 or OC1D-A8 | GGGAAGAGAAGGACATATGATTTTCGAAACGTTTCTTTCAAGTTCTT AATCATTCCCATTTTTGACTAGTACATGACCACTT |
| 129 | OC1D-B18 | GGGAAGAGAAGGACATATGATCATTAGATGCGCAGTTCGAAGCCGG TACAGCTGGCGCGCGTTGACTAGTACATGACCACTT |
| 130 | OC1D-B19 | GGGAAGAGAAGGACATATGATAAAGAATAACCTTAAAATAACACCA CCGCCTCACAGCATATTGACTAGTACATGACCACTT |
| 131 | OC1D-B20 or OC1D-A6 | GGGAAGAGAAGGACATATGATAAATTGATCTATTCTTTTCGGTGCTA TTTATCTTCCATTTTTGACTAGTACATGACCACTT |
| 132 | OC1D-B21 | GGGAAGAGAAGGACATATGATCTACTCGCGCGGCGGACAAAAGCGC AACCCAGCACCCATGTTGACTAGTACATGACCACTT |
| 133 | OC1D-B22 or OC1D-A10 | GGGAAGAGAAGGACATATGATTCTTAGTTTGTAATTACTTTTCCTTCC TTTTATTCTATTTTTGACTAGTACATGACCACTT |
| 134 | OC1D-B23 | GGGAAGAGAAGGACATATGATAACCCGCGCAGACTTACAAGCGCGC AAAAAAAGGGTACGTTTGACTAGTACATGACCACTT |
| 135 | OC1D-B24 or OC1D-A23 | GGGAAGAGAAGGACATATGATATTCCTTTATGCCGCATCATTTTATTG TTTATGACAATTTTTGACTAGTACATGACCACTT |
| 136 | OC1D-B25 or OC1D-A9 | GGGAAGAGAAGGACATATGATATTTCGTACTACTTTTCTTCCAAGCTT CAATCGCCCATTTTTGACTAGTACATGACCACTT |
| 137 | OC1D-B26 or OC1D-A24 | GGGAAGAGAAGGACATATGATTCACTCATTCGCAACACAATTGTATT CGCATCTGCGATTTTTGACTAGTACATGACCACTT |
| 138 | OC1D-B27 or OC1D-A12 | GGGAAGAGAAGGACATATGATATTATTTCCACAGTTCCTTTATCCAC ACATCTTCTCATTTTTGACTAGTACATGACCACTT |
| 139 | OC1D-B28 | GGGAAGAGAAGGACATATGATAAACTCGTTATCTATTCGTTTATTTG CATCTCTTTCATTTTTGACTAGTACATGACCACTT |
| 140 | OC1D-B29 | GGGAAGAGAAGGACATATGATCCAACCTCTAAAGTACTGGTCGCCTA GGGAGACTGTTCGGTTGACTAGTACATGACCACTT |
| 141 | OC1D-B30 OC1D-A13 | GGGAAGAGAAGGACATATGATTTCCTTTTTGCTATTTCCGTTAATGTA AACTCTCCTATTTTTGACTAGTACATGACCACTT |
| 142 | OC1D-B31 | GGGAAGAGAAGGACATATGATCCTTATGGCCTAGTAGGGATCCGGGC GCCGACCAGCGCGATTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 143 | OC1D-B32 OC1D-A18 | GGGAAGAGAAGGACATATGATCGTCTGTCTTCTTCGAATACGTTTTG GGCTAAGCCCATTTTTGACTAGTACATGACCACTT |
| 144 | OC1D-B33 | GGGAAGAGAAGGACATATGATTCAACCAAACTGCCGACGACCGAGG TATGTCCTTATGTACTTGACTAGTACATGACCACTT |
| 145 | OC1D-B34 | GGGAAGAGAAGGACATATGATTACGGGTCTGAGCAAAAGCGAAGGA AGCAGGCGCAGGGATTTGACTAGTACATGACCACTT |
| 146 | OC1D-B35 or OC1D-A4 | GGGAAGAGAAGGACATATGATTCTCTCATTCGCAACACAATTGTATT CGCATCTGCGATTTTTGACTAGTACATGACCACTT |
| 147 | OC1D-B36 | GGGAAGAGAAGGACATATGATGCTCTAAAGTACTAAGCGTTTGCGCC GATGCCCGGACCGCTTGACTAGTACATGACCACTT |
| 148 | OC1D-B37 | GGGAAGAGAAGGACATATGATACTTCATTAATGTGAGGCCGTCAGGG GGCAACCTTCGAGCTTGACTAGTACATGACCACTT |
| 149 | OC1D-B38 | GGGAAGAGAAGGACATATGATTCCTTATTCTTGTTACTACTTTCTTTT CCTATTTTTTCTTTGACTAGTACATGACCACTT |
| 150 | OC1D-B39 or OC1D-A14 | GGGAAGAGAAGGACATATGATCGTTATTTTCATTTTCTTGTTCCCCAT ATGCCCAGGCGCATTGACTAGTACATGACCACTT |
| 151 | OC1D-B40 | GGGAAGAGAAGGACATATGATACCAGCGGCGTAGAAACGTACAGCT CGCCTGTAACGCCTGTTGACTAGTACATGACCACTT |
| 152 | OC1D-B41 | GGGAAGAGAAGGACATATGATCGATATGGGTGCGGGAATGTACGTT CACCGAATATGCTCCTTGACTAGTACATGACCACTT |
| 153 | OC1D-B42 | GGGAAGAGAAGGACATATGATTAACAGTGCGTAGTCATATCGAATGT TTATCTTCCTATTTTGACTAGTACATGACCACTT |
| 154 | OC1D-B43 | GGGAAGAGAAGGACATATGATCAGACTCTCGCCCAATTCGCAAGGC GTTGCATTGCGATTTTGACTAGTACATGACCACTT |
| 155 | OC1D-B44 | GGGAAGAGAAGGACATATGATTTCCAACTCTCCACGAGAGCATGGGT CGAATGACTCATTTTGACTAGTACATGACCACTT |
| 156 | OC1D-B45 | GGGAAGAGAAGGACATATGATGCATCGCGCGTCACTCAACTCGTGAT TACCGAGGGCGCCGTTGACTAGTACATGACCACTT |
| 157 | OC1D-B46 | GGGAAGAGAAGGACATATGATCTGAATCTTTCCGCAGCCCTGTCCTT TTAAAGACAGGTTTTGACTAGTACATGACCACTT |
| 158 | OC1D-B47 | GGGAAGAGAAGGACATATGATTTGTTACTTACTTCGTCTATCTTCTG TTGCACACAGTTTTGACTAGTACATGACCACTT |
| 159 | OC1D-B48 | GGGAAGAGAAGGACATATGATTCAAATCTTCAGCGATAATGGCACA ATTTCCGCGCCATTTTGACTAGTACATGACCACTT |
| 160 | OC1D-B49 | GGGAAGAGAAGGACATATGATTTATGTGAGATGATGTGTGTTCCTAG TTTTATCTTGCTCTTTGACTAGTACATGACCACTT |
| 161 | OC1D-B50 | GGGAAGAGAAGGACATATGATCCACTTTTCCATTAACTGTTGCGGGC AAGTAGCACCGTTTTGACTAGTACATGACCACTT |
| 162 | OC1D-B51 | GGGAAGAGAAGGACATATGATAGAGAAGACCATTCGGAAAGAGCTG CGTGTCCTTATGTACTTGACTAGTACATGACCACTT |
| 163 | OC1D-B52 | GGGAAGAGAAGGACATATGATTCTTATGTAGCAAGCAAATGTGCCG CCGAGCCGACGCCATTGACTAGTACATGACCACTT |
| 164 | OC1D-B53 | GGGAAGAGAAGGACATATGATAAGCGCATAATAAGCCAGCCAGTTC TTGGCGCGCGGGGTATTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 165 | OC1D-B54 | GGGAAGAGAAGGACATATGATTAGTCCGCATTTCTATTTTCTATATGGCTTACTGCCATTTTTGACTAGTACATGACCACTT |
| 166 | OC1D-B55 | GGGAAGAGAAGGACATATGATATAAAGAACACGCAAAACCACCCGGACACCCGGTGCCGTGTTGACTAGTACATGACCACTT |
| 167 | OC1D-B56 | GGGAAGAGAAGGACATATGATACACAGGCGGTGGAGCCGAAGGGCACCGGGACAAACCGACTTGACTAGTACATGACCACTT |
| 168 | OC1D-B57 | GGGAAGAGAAGGACATATGATAGTTCCGGCGCAGCAGCGTCCTCACGTTTTACGTGCCCCATTGACTAGTACATGACCACTT |
| 169 | OC1D-B58 | GGGAAGAGAAGGACATATGATGACCGTCGCGATCGTTTATAATGTTCTGGATCTTTCATTTTTGACTAGTACATGACCACTT |
| 170 | OC1D-B59 | GGGAAGAGAAGGACATATGATAAGTGGGGCCCCGACGACTTTTCCTTCCTCTCTTCCGGCATTGACTAGTACATGACCACTT |
| 171 | OC1D-B60 | GGGAAGAGAAGGACATATGATATCAACATACCAAAATGTCATTTCCAATCTTTTCCCATTTTTGACTAGTACATGACCACTT |
| 172 | OC1D-B61 | GGGAAGAGAAGGACATATGATAGCGAACAAACAAGGGTGCCCAGGCCCCCTTCGCACATCGTTGACTAGTACATGACCACTT |
| 173 | OC1D-B62 | GGGAAGAGAAGGACATATGATCCTCTGTAACGCAAAGTCAAGTCGCGCAAGGCCGCCCGCGTTGACTAGTACATGACCACTT |
| 174 | OC1D-B63 | GGGAAGAGAAGGACATATGATCTTCATCTGCGATTACGGTACACTTTAGTGTATCGTTTTTTGACTAGTACATGACCACTT |
| 175 | OC1D-B64 | GGGAAGAGAAGGACATATGATGCCTATGTGCTAGATGCAGCAGCAACCGCCGGCGACTGGATTGACTAGTACATGACCACTT |
| 176 | OC1D-B65 | GGGAAGAGAAGGACATATGATCCGCGCCCTAACCTTCTGACCAAGCTTCCCTGGCACTTGGTTGACTAGTACATGACCACTT |
| 177 | OC1D-B66 | GGGAAGAGAAGGACATATGATCCTTATGTATTATCAGTCATACCGGACGCAGCCCGCTGGATTGACTAGTACATGACCACTT |
| 178 | OC1D-B67 | GGGAAGAGAAGGACATATGATCTAATCTATACTGGCTGCTAACGCTTTTTCTTTTCCATTTTTGACTAGTACATGACCACTT |
| 179 | OC1D-B68 | GGGAAGAGAAGGACATATGATCAGTTTACGCGGAGTCGTTTGTGTCCATTTCTTCTCATTTTTGACTAGTACATGACCACTT |
| 180 | OC1D-B69 | GGGAAGAGAAGGACATATGATTCACGTGAGATGATGTGTGTTCCTAGTTTTATCTTGCTCTTTGACTAGTACATGACCACTT |
| 181 | OC1D-B70 | GGGAAGAGAAGGACATATGATTCCTTGTGTACCGCTCCGAATGTGCTCCAGCGCGCCTCGGTTGACTAGTACATGACCACTT |
| 182 | OC1D-B71 | GGGAAGAGAAGGACATATGATAAGCCGGCCCGGGAACATGTCACGCGCGCGCGCAAAGTAGTTGACTAGTACATGACCACTT |
| 183 | OC1D-B72 | GGGAAGAGAAGGACATATGATCCTGGATTTCCGAAATTAGAGTGCCGTTTCGTTACGGTTTTTGACTAGTACATGACCACTT |
| 184 | OC1D-B73 | GGGAAGAGAAGGACATATGATCGTGTCATCCGCACAAGGAGGCCTGCATGGCAGGGACACGTTGACTAGTACATGACCACTT |
| 185 | OC1D-B74 | GGGAAGAGAAGGACATATGATGAGTAGACTTTTTGTATCATTTTTTATCGTAAGATATTTTTGACTAGTACATGACCACTT |
| 186 | OC1D-B75 | GGGAAGAGAAGGACATATGATCCATGTGAGATGATGTGTGTTCCTAGTTTTATCTTGCTCTTTGACTAGTACATGACCACTT |
| 187 | OC1D-B76 | GGGAAGAGAAGGACATATGATCTTTGCTCTAGAGTGTAGTCTATGAGGGACAAGGTAGCCATTGACTAGTACATGACCACTT |
| 188 | OC1D-B77 | GGGAAGAGAAGGACATATGATGTTG-GTTTTCTTTCTCTTTCTTTTCTTTCTCTTTCTATTTTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 189 | OC1D-B78 | GGGAAGAGAAGGACATATGATCAATCGGGCGGGGGTAAGAGGCGTG CGCAGCGTGGAGGTGTTGACTAGTACATGACCACTT |
| 190 | OC1D-B79 | GGGAAGAGAAGGACATATGATCACCGTGGTGCGCAAAGCCGCAACG AGAACTGCGGAATCGTTGACTAGTACATGACCACTT |
| 191 | OC1D-B80 | GGGAAGAGAAGGACATATGATTGCTTTAAGTCTTTTTATCATTTTGTT TCCTTCATTTTTTTTGACTAGTACATGACCACTT |
| 192 | OC1D-B81 | GGGAAGAGAAGGACATATGATCGACTAGTTATACTGCAAAGGCTATA AGCGCGAGCGCGCGTTGACTAGTACATGACCACTT |
| 193 | OC1D-B82 | GGGAAGAGAAGGACATATGATGAGTAATAGATGGCGTACACAAATC GGATACGACGAGCGCTTGACTAGTACATGACCACTT |
| 194 | OC1D-B83 | GGGAAGAGAAGGACATATGATTTTCGCTTCAAGATTCCCAACGCCTT GTAAGTCAAGGTTTTTGACTAGTACATGACCACTT |
| 195 | OC1D-B84 | GGGAAGAGAAGGACATATGATGTGTGAGATGAGCCCCTGGACCAGA CGCACGCTCGCACTGTTGACTAGTACATGACCACTT |
| 196 | OC1D-B85 | GGGAAGAGAAGGACATATGATCAGGATGCGGCGCCGGTAATTGACT TCCCCCTACGTAGGATTGACTAGTACATGACCACTT |
| 197 | OC1D-B86 | GGGAAGAGAAGGACATATGATCAGGGACCCGGCCGGTGCATCTCCTT CTTTAGCGTACGCCTTGACTAGTACATGACCACTT |
| 198 | OC1D-B87 | GGGAAGAGAAGGACATATGATCTGCTCTAAAGTACCAACCGCGGGA GCTAAATGCAAGCCGTTGACTAGTACATGACCACTT |
| 199 | OC1D-B88 | GGGAAGAGAAGGACATATGATGATTGCCATGCATTAGGGGGGACG CGCGCGAAAGGGAGATTGACTAGTACATGACCACTT |
| 200 | OC1D-B89 | GGGAAGAGAAGGACATATGATTCGCTCTAAAGTACCAACCGCGGGA GCTAAATGCAAGCCGTTGACTAGTACATGACCACTT |
| 201 | OC1D-B90 | GGGAAGAGAAGGACATATGATAAAAAACCGGGGTTCTTAATTTTCAT TGTTCGTCGTACTTTTGACTAGTACATGACCACTT |
| 202 | OC1D-B91 | GGGAAGAGAAGGACATATGATAACCCATTGGTGAATCGCAACCACA GCCAGCCCGGCGCGATTGACTAGTACATGACCACTT |
| 203 | OC1D-B92 | GGGAAGAGAAGGACATATGATCGAAGTGAGGGGATCGCGCGGGGTG CACCTAAATATGGGATTGACTAGTACATGACCACTT |
| 204 | OC1D-B93 | GGGAAGAGAAGGACATATGATAGCCTTATGTACTATAGAAGTCAGCT ATCCGCCGCACAATTTGACTAGTACATGACCACTT |
| 205 | OC1D-B94 | GGGAAGAGAAGGACATATGATCGTTGTTTTTCCCAAAGCTCGTTAGC ATTCATTCCTATTTTTGACTAGTACATGACCACTT |
| 206 | OC1D-B95 | GGGAAGAGAAGGACATATGATGATCATCAGCGGAAAGCACGAAACG CCACGGGCCGCGGCATTGACTAGTACATGACCACTT |
| 207 | OC1D-B96 | GGGAAGAGAAGGACATATGATTCCTTCCTATTGACAATGCGCCCGGG CCTCTTCAATTGTATTGACTAGTACATGACCACTT |
| 208 | OC1D-B97 | GGGAAGAGAAGGACATATGATAGTTGCCGCGCGGCGCAAGATTGGA GAGTCCCGGGCTGTATTGACTAGTACATGACCACTT |
| 209 | OC1D-B98 | GGGAAGAGAAGGACATATGATCATAAGTTCGTTCATTCCGTTAACAC GCGTATGGCGTTTTTGACTAGTACATGACCACTT |
| 210 | OC1D-B99 | GGGAAGAGAAGGACATATGATCCTTTGTCTCCAAATCTTAGGACTGA ATGAGTGCCTATTTTGACTAGTACATGACCACTT |
| 211 | OC1D-B100 | GGGAAGAGAAGGACATATGATCTTCTTTGAGAATTCTCTTTTTACAAT TCCGGCGCCGTGATTGACTAGTACATGACCACTT |
| 212 | OC1D-A16 | GGGAAGAGAAGGACATATGATTAGGCTAACTGTTTAGGGATTTGATA TGCATGAGGAGCACTTGACTAGTACATGACCACTT |
| 213 | OC1D-A17 | GGGAAGAGAAGGACATATGATCGTCTGTCTTCTTCGAATACGTTTTG GGCTAAGCCCATTTTTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 214 | OC1D-A20 | GGGAAGAGAAGGACATATGATTAGGCTAACTGCTCAGGGATTTGATATGCATGAGGAGCACTTGACTAGTACATGACCACTT |
| 215 | OC1D-A21 | GGGAAGAGAAGGACATATGATTAGGCTAACTGTTCAGGGACTTGATATGCATGAGGAGCACTTGACTAGTACATGACCACTT |
| 216 | OC1D-A22 | GGGAAGAGAAGGACATATGATTAGGCTCACTGTTCAGGGATTTGATATGCATGAGGAGCACTTGACTAGTACATGACCACTT |
| 217 | OC1D-A25 | GGGAAGAGAAGGACATATGATTAGGCTAACTGTTCAGGGATTTGATATGCATGGGGAGCACTTGACTAGTACATGACCACTT |
| 218 | OC1D-A26 | GGGAAGAGAAGGACATATGATTTCTTCCTATTGACGATGCGCCCGGGCCTCTTCAATTGTATTGACTAGTACATGACCACTT |
| 219 | OC1D-A27 | GGGAAGAGAAGGACATATGATTAGGCTAACTGTTCGGGGATTTGATATGCATGAGGAGCACTTGACTAGTACATGACCACTT |
| 220 | OC1D-A28 | GGGAAGAGAAGGACATATGATTAGGCTAACTGTTCAGGGATTTGATATGCACGAGGAGCACTTGACTAGTACATGACCACTT |
| 221 | OC1D-A29 | GGGAAGAGAAGGACATATGATTAGGTTAACTGTTCAGGGATTTGATATGCATGAGGAGCACTTGACTAGTACATGACCACTT |
| 222 | OC1D-A30 | GGGAAGAGAAGGACATATGATTAGGCTAACTGTTCAGGGATTTGATGTGCATGAGGAGCACTTGACTAGTACATGACCACTT |
| 112 | OC1D-B1 or OC1D-A2 | GGGAAGAGAAGGACATATGATTCATGTGAGATGATGTGTGTTCCTAGTTTTATCTTGCTCTTTGACTAGTACATGACCACTT |
| 113 | OC1D-B2 or OC1D-A1 | GGGAAGAGAAGGACATATGATTAGGCTAACTGTTCAGGGATTTGATATGCATGAGGAGCACTTGACTAGTACATGACCACTT |
| 114 | OC1D-B3 or OC1D-A19 | GGGAAGAGAAGGACATATGATCCGCTCTAAAGTACCAACCGCGGGAGCTAAATGCAAGCCGTTGACTAGTACATGACCACTT |
| 115 | OC1D-B4 | GGGAAGAGAAGGACATATGATTGTGTCAGGCTCTAGAGTCTAGACGGCCGGGGTCCCGGATTTGACTAGTACATGACCACTT |
| 116 | OC1D-B5 | GGGAAGAGAAGGACATATGATCCTTATGTCTAGCGGCCTTACGCGATTAGTGGCGTTTTGTTTGACTAGTACATGACCACTT |
| 117 | OC1D-B6 | GGGAAGAGAAGGACATATGATCTTTATGTATTATCAGTCATACCGGACGCAGCCCGCTGGATTGACTAGTACATGACCACTT |
| 118 | OC1D-B7 or OC1D-A3 | GGGAAGAGAAGGACATATGATTGTGTTATTACACTTCGTGATTTTCCTTGCTTTTCTATTTTTGACTAGTACATGACCACTT |
| 119 | OC1D-B8 | GGGAAGAGAAGGACATATGATCCAACATCTAAAGTACTGGTCGCCTAGGGAGACTGTTCGGTTGACTAGTACATGACCACTT |
| 120 | OC1D-B9 | GGGAAGAGAAGGACATATGATGCTATATTCGCAAAAGCAGGCTGAGTGCGGCAGGCGCGTGTTGACTAGTACATGACCACTT |
| 121 | OC1D-B10 | GGGAAGAGAAGGACATATGATTCATTCATTCGCAACACAATTGTATTCGCATCTGCGATTTTTGACTAGTACATGACCACTT |
| 122 | OC1D-B11 or OC1D-A11 | GGGAAGAGAAGGACATATGATCTTTCTCTTTTCTAATATTTAATTTATTGGGTACCAATTTTTGACTAGTACATGACCACTT |

TABLE 2-continued

List of deoxyribonucleotides aptamers based on the top sequences from selection experiments A and B.

| SEQ ID NO | Name | Total Sequence |
|---|---|---|
| 123 | OC1D-B12 or OC1D-A7 | GGGAAGAGAAGGACATATGATCTTTGTTTCGCATACGTTTTCTTTTTC TCTCTTCTTATTTTTGACTAGTACATGACCACTT |
| 124 | OC1D-B13 or OC1D-A5 | GGGAAGAGAAGGACATATGATTATTCTGTTCTTCAAAAATCTTTTAG CGTATACGCTATTTTTGACTAGTACATGACCACTT |
| 125 | OC1D-B14 | GGGAAGAGAAGGACATATGATTTCCTTATGTTCGGTCAACAGGGACT GCTGCAGCACCGGCTTGACTAGTACATGACCACTT |
| 126 | OC1D-B15 | GGGAAGAGAAGGACATATGATTAAGCGCACTCAACAGGGTCTATGA TCCGCGCCGATCATGTTGACTAGTACATGACCACTT |
| 127 | OC1D-B16 or OC1D-A15 | GGGAAGAGAAGGACATATGATCCGCTTTCCATTGAGATTATAAGCTG TTAGAGACTTATTTTTGACTAGTACATGACCACTT |
| 128 | OC1D-B17 or OC1D-A8 | GGGAAGAGAAGGACATATGATTTTCGAAACGTTTCTTTCAAGTTCTT AATCATTCCCATTTTTGACTAGTACATGACCACTT |
| 129 | OC1D-B18 | GGGAAGAGAAGGACATATGATCATTAGATGCGCAGTTCGAAGCCGG TACAGCTGGCGCGCGTTGACTAGTACATGACCACTT |
| 130 | OC1D-B19 | GGGAAGAGAAGGACATATGATAAAGAATAACCTTAAAATAACACCA CCGCCTCACAGCATATTGACTAGTACATGACCACTT |

What is claimed is:

1. A consumer product composition comprising a surfactant and a nucleic acid aptamer comprising at least one oligonucleotide with at least 50% nucleotide sequence identity to: SEQ ID NO 1-10, SEQ ID NO 13, SEQ ID NO 25, SEQ ID NO 26, SEQ ID NO 28, SEQ ID NO 29, SEQ ID NO 35, SEQ ID NO 49, SEQ ID NO 66, SEQ ID NO 69, SEQ ID NO 75, SEQ ID NO 87, SEQ ID NO 89, SEQ ID NO 102-106, SEQ ID NO 108-121, SEQ ID NO 124, SEQ ID NO 136, SEQ ID NO 137, SEQ ID NO 139, SEQ ID NO 140, SEQ ID NO 146, SEQ ID NO 160, SEQ ID NO 177, SEQ ID NO 180, SEQ ID NO 186, SEQ ID NO 198, SEQ ID NO 200, SEQ ID NO 212, SEQ ID NO 214-217, SEQ ID NO 219-222, and mixtures thereof.

2. The consumer product composition of claim 1, wherein said surfactant is selected from the group consisting of anionic surfactant, amphoteric surfactant, nonionic surfactant, zwitterionic surfactant, cationic surfactant, and mixtures thereof.

3. The consumer product composition of claim 1, wherein said surfactant comprises an anionic surfactant selected from the group consisting of alkyl sulfates, alkyl ether sulfates, alkyl sulfonates, alkyl sarcosinates, and mixtures thereof.

4. The consumer product composition of claim 1, wherein said surfactant comprises an amphoteric surfactant selected from the group consisting of betaines.

5. The consumer product composition of claim 1, wherein said surfactant comprises a nonionic surfactant selected from the group consisting of poloxamers, polyoxyethlyene, polyoxyethylene sorbitan esters, fatty alcohol ethoxylates, polyethylene oxide condensates of alkyl phenols, ethylene oxide condensates of propylene oxide and ethylene diamine, ethylene oxide condensates of aliphatic alcohols, tertiary amine oxides, tertiary phosphine oxides, dialkyl sulfoxides, and mixtures thereof.

6. The consumer product composition of claim 1, wherein said surfactant comprises a cationic surfactant selected from the group consisting of quaternary ammonium compounds.

7. The consumer product composition of claim 1, wherein said nucleic acid aptamer has a binding affinity for an epitope of a surface.

8. The consumer product composition of claim 7, wherein said surface is selected from the group consisting of hair, skin, teeth, internal body parts or organs, gums, tongues, throat soft tissue, microorganisms, fabrics, dishware, hard surfaces, tissues or paper towels, and components of absorbent articles.

9. The consumer product composition of claim 1, wherein said oligonucleotide comprises oligonucleotide selected from the group consisting of SEQ ID NO 1, SEQ ID NO 9, SEQ ID NO 25, SEQ ID NO 112, SEQ ID NO 120, and SEQ ID NO 136.

10. The consumer product composition of claim 1, wherein said oligonucleotide comprises non-natural nucleobases.

11. The consumer product composition of claim 1, wherein said non-natural nucleobases are selected from the group comprising hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, and mixtures thereof.

12. The consumer product composition of claim 10, wherein the nucleosides of the oligonucleotide are linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, and mixtures thereof.

13. The consumer product composition of claim 1, where said derivatives of ribonucleotides or said derivatives of deoxyribonucleotides are selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

14. The consumer product composition of claim 1, wherein said consumer product composition further comprises a polymeric material, wherein said polymeric material is covalently attached to said nucleic acid aptamer.

15. The consumer product composition of claim 14, wherein said polymeric material is polyethylene glycol.

16. The consumer product composition of claim 1, wherein nucleotides at the 5'- and 3'-ends of said oligonucleotide are inverted.

17. The consumer product composition of claim 1, wherein at least one nucleotide of said oligonucleotide is fluorinated at the 2' position of the pentose group.

18. The consumer product composition of claim 1, wherein the pyrimidine nucleotides of the oligonucleotide are fluorinated at the 2' position of the pentose group.

19. The consumer product composition of claim 1, wherein said consumer product composition further comprises an active ingredient.

20. The consumer product composition of claim 19, wherein said nucleic acid aptamer is covalently or non-covalently attached to said active ingredient.

21. The consumer product composition of claim 19, wherein said active ingredient is selected from the group consisting of: perfumes, perfume microcapsules, optical brighteners, dyes, insect repellants, silicones, waxes, flavors, vitamins, sunscreen agents, anti-acne agents, fabric conditioning agents, hair conditioning agents, skin care agents, enzymes, anti-bacterial agents, bleaches, whitening agents, anti-stain agents, anti-cavity agents, anti-erosion agents, anti-tartar agents, anti-calculus agents, anti-plaque agents, teeth remineralizing agents, anti-fracture agents, strengthening agents, abrasion resistance agents, anti-gingivitis agents, anti-microbial agents, anti-bacterial agents, anti-fungal agents, anti-yeast agents, anti-viral, anti-malodor agents, breath freshening agents, sensates, taste enhancement agents, olfactory enhancement agents, anti-adherence agents, smoothness agents, surface modification agents, anti-tooth pain agents, anti-sensitivity agents, anti-inflammatory agents, gum protecting agents, periodontal actives, tissue regeneration agents, anti-blood coagulation agents, anti-clot stabilizer agents, salivary stimulant agents, salivary rheology modification agents, enhanced retention agents, soft/hard tissue targeted agents, tooth/soft tissue cleaning agents, antioxidants, pH modifying agents, H-2 antagonists, analgesics, natural extracts, essential oils, cations, phosphates, fluoride ion sources, peptides, nutrients, and mixtures thereof.

22. The consumer product composition of claim 19, wherein said active ingredient is selected from the group consisting of perfumes, perfume microcapsules, fabric conditioning agents, hair conditioning agents, anti-acne agents, sunscreen agents, dyes, and optical brighteners.

23. The consumer product composition of claim 19, wherein said active ingredient is 4,4'-diamino-2,2'-stilbene-disulfonic acid.

24. The consumer product composition of claim 1, wherein said nucleic acid aptamer is covalently or non-covalently attached to a nanomaterial.

25. The consumer product composition of claim 1, wherein said composition comprises two different nucleic acid aptamers, wherein said two different nucleic acid aptamers have binding affinities for different epitopes of a surface.

26. The consumer product composition of claim 1, wherein said composition comprises from about 0.1% to about 25%, by weight of said composition, of said surfactant.

27. A method for treating a surface, said method comprising the step of contacting said surface with a consumer product composition according to claim 1.

28. The method of claim 27, wherein said surface has an epitope, wherein said nucleic acid aptamer of said consumer product composition has a binding affinity for said epitope of said surface.

29. The method of claim 27, wherein said surface is selected from the group consisting of hair, skin, teeth, internal body parts or organs, gums, tongues, throat soft tissue, microorganisms, fabrics, dishware, hard surfaces, tissues or paper towels, and components of absorbent articles.

30. A method for delivering an active ingredient to a surface, said method comprising the step of contacting said surface with a consumer product composition according to claim 19.

31. The method of claim 30, wherein said surface has an epitope, wherein said nucleic acid aptamer of said consumer product composition has a binding affinity for said epitope of said surface.

32. The method of claim 30, wherein said surface is selected from the group consisting of hair, skin, teeth, internal body parts or organs, gums, tongues, throat soft tissue, microorganisms, fabrics, dishware, hard surfaces, tissues or paper towels, and components of absorbent articles.

* * * * *

SEQUENCE LISTING

<160> NUMBER OF SEQ ID NOS: 224

<210> SEQ ID NO 1
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 1
gggaagagaa ggacauauga uucaugugag augaugugug uuccuaguuu uaucuugcuc    60
uuugacuagu acaugaccac uu    82

<210> SEQ ID NO 2
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 2
gggaagagaa ggacauauga uuaggcuaac uguucaggga uuugauaugc augaggagca    60
cuugacuagu acaugaccac uu    82

<210> SEQ ID NO 3
<211> LENGTH: 82
<212> TYPE: RNA
<213> ORGANISM: Artificial Sequence

```
<220> FEATURE:
<223> OTHER INFORMATION: Synthetic aptamer sequence

<400> SEQUENCE: 3
gggaagagaa ggacauauga uccgcucuaa aguaccaacc gcgggagcua aaugcaagcc    60
guugacuagu acaugaccac uu                                            82

<210> SEQ ID NO 4
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 4
gggaagagaa ggacauauga uugugucagg cucuagaguc uagacggccg ggucccgga    60 uuugacuagu acaugaccac uu                                            82

<210> SEQ ID NO 5
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 5
gggaagagaa ggacauauga uccuuauguc uagcggccuu acgcgauuag uggcguuuug    60
uuugacuagu acaugaccac uu                                            82

<210> SEQ ID NO 6
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 6
gggaagagaa ggacauauga ucuuuaugua uuaucaguca uaccggacgc agcccgcugg    60
auugacuagu acaugaccac uu                                            82

<210> SEQ ID NO 7
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 7
gggaagagaa ggacauauga uuguguuauu acacuucgug auuuuccuug cuuuucuauu    60
uuugacuagu acaugaccac uu                                            82

<210> SEQ ID NO 8
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 8
gggaagagaa ggacauauga uccaacaucu aaaguacugg ucgccuaggg agacuguucg    60
guugacuagu acaugaccac uu                                            82
```

```
<210> SEQ ID NO 9
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 9
gggaagagaa ggacauauga ugcuauauuc gcaaaagcag gcugagugcg gcaggcgcgu      60
guugacuagu acaugaccac uu                                              82

<210> SEQ ID NO 10
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 10
gggaagagaa ggacauauga uucauucauu cgcaacacaa uguauucgc aucugcgauu      60 uuugacuagu acaugaccac uu                                              82

<210> SEQ ID NO 11
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 11
gggaagagaa ggacauauga ucuuucucuu uucuaauauu uaauuauug gguaccaauu      60 uuugacuagu acaugaccac uu                                              82

<210> SEQ ID NO 12
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 12
gggaagagaa ggacauauga ucuuuguuuc gcauacguuu ucuuuucuc ucuucuuauu      60 uuugacuagu acaugaccac uu                                              82

<210> SEQ ID NO 13
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 13
gggaagagaa ggacauauga uuauucuguu cuucaaaaau cuuuuagcgu auacgcuauu      60
uuugacuagu acaugaccac uu                                              82

<210> SEQ ID NO 14
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 14
```
gggaagagaa ggacauauga uuccuuaug uucggucaac agggacugcu gcagcaccgg    60
cuugacuagu acaugaccac uu                                            82

<210> SEQ ID NO 15
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 15
gggaagagaa ggacauauga uuaagcgcac ucaacagggu cuaugauccg cgccgaucau    60
guugacuagu acaugaccac uu                                            82

<210> SEQ ID NO 16
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 16
gggaagagaa ggacauauga uccgcuuucc auugagauua uaagcuguua gagacuuauu    60
uuugacuagu acaugaccac uu                                            82

<210> SEQ ID NO 17
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 17
gggaagagaa ggacauauga uuuucgaaac guuucuuuca aguucuuaau cauucccauu    60
uuugacuagu acaugaccac uu                                            82

<210> SEQ ID NO 18
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 18
gggaagagaa ggacauauga ucauuagaug cgcaguucga agccgguaca gcuggcgcgc    60
guugacuagu acaugaccac uu                                            82

<210> SEQ ID NO 19
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 19
gggaagagaa ggacauauga uaaagaauaa ccuuaaaaua acaccaccgc cucacagcau    60
auugacuagu acaugaccac uu                                            82

<210> SEQ ID NO 20
<211> LENGTH: 82
<212> TYPE: RNA

<213> ORGANISM: Artificial Sequence
<220> FEATURE:
<223> OTHER INFORMATION: Synthetic aptamer sequence

<400> SEQUENCE: 20
gggaagagaa ggacauauga uaaauugauc uauucuuuuc ggugcuauuu aucuuccauu    60
uuugacuagu acaugaccac uu                                             82

<210> SEQ ID NO 21
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 21
gggaagagaa ggacauauga ucuacucgcg cggcggacaa aagcgcaacc cagcacccau    60
guugacuagu acaugaccac uu                                             82

<210> SEQ ID NO 22
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 22
gggaagagaa ggacauauga uucuuaguuu guaauuacuu uccuuccuu uauucuauu      60 uuugacuagu acaugaccac uu                                             82

<210> SEQ ID NO 23
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 23
gggaagagaa ggacauauga uaacccgcgc agacuuacaa gcgcgcaaaa aaagggguacg   60 uuugacuagu acaugaccac uu                                             82

<210> SEQ ID NO 24
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 24
gggaagagaa ggacauauga uauuccuuua ugccgcauca uuuuauuguu uaugacaauu    60
uuugacuagu acaugaccac uu                                             82

<210> SEQ ID NO 25
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 25
gggaagagaa ggacauauga uauuucguac uacuuuucuu ccaagcuuca aucgcccauu    60
uuugacuagu acaugaccac uu                                             82

```
<210> SEQ ID NO 26
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 26
gggaagagaa ggacauauga uucacucauu cgcaacacaa uuguauucgc aucugcgauu    60
uuugacuagu acaugaccac uu                                            82

<210> SEQ ID NO 27
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 27
gggaagagaa ggacauauga uauuauuccc acaguccuu uaccacaca ucuucucauu     60 uuugacuagu acaugaccac uu                                            82

<210> SEQ ID NO 28
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 28
gggaagagaa ggacauauga uaaacucguu aucuauucgu uuauuugcau cucuuucauu    60
uuugacuagu acaugaccac uu                                            82

<210> SEQ ID NO 29
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 29
gggaagagaa ggacauauga uccaaccucu aaaguacugg ucgccuaggg agacuguucg    60
guugacuagu acaugaccac uu                                            82

<210> SEQ ID NO 30
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 30 gggaagaa ggacauauga uuuccuuuuu gcuauuuccg uuaauguaaa cucuccuauu      60
uuugacuagu acaugaccac uu                                            82

<210> SEQ ID NO 31
<211> LENGTH: 82
<212> TYPE: RNA
<213> ORGANISM: Artificial Sequence
<220> FEATURE:
<223> OTHER INFORMATION: Synthetic aptamer sequence
```

```
<400> SEQUENCE: 31
gggaagagaa ggacauauga uccuuauggc cuaguaggga uccgggcgcc gaccagcgcg    60
auugacuagu acaugaccac uu                                            82

<210> SEQ ID NO 32
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 32
gggaagagaa ggacauauga ucgucugucu ucuucgaaua cguuugggc uaagcccauu     60 uuugacuagu acaugaccac uu                                            82

<210> SEQ ID NO 33
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 33
gggaagagaa ggacauauga uucaaccaaa cugccgacga ccgagguaug uccuuaugua    60
cuugacuagu acaugaccac uu                                            82

<210> SEQ ID NO 34
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 34
gggaagagaa ggacauauga uuacgggucu gagcaaaagc gaaggaagca ggcgcaggga    60
uuugacuagu acaugaccac uu                                            82

<210> SEQ ID NO 35
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 35
gggaagagaa ggacauauga uucucucauu cgcaacacaa uuguauucgc aucugcgauu    60
uuugacuagu acaugaccac uu                                            82

<210> SEQ ID NO 36
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 36
gggaagagaa ggacauauga ugcucuaaag uacuaagcgu uugcgccgau gcccggaccg    60
cuugacuagu acaugaccac uu                                            82

<210> SEQ ID NO 37
<211> LENGTH: 82
```

```
<212> TYPE: RNA
<213> ORGANIZM: Artificial Sequence
<220> FEATURE:
<223> OTHER INFORMATION: Synthetic aptamer sequence

<400> SEQUENCE: 37
gggaagagaa ggacauauga uacuucauua augugaggcc gucaggggc aaccuucgag    60 cuugacuagu acaugaccac uu                                            82

<210> SEQ ID NO 38
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 38
gggaagagaa ggacauauga uuccuuauuc uguuacuac uuucuuucc uauuuuuuc      60 uuugacuagu acaugaccac uu                                            82

<210> SEQ ID NO 39
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 39
gggaagagaa ggacauauga ucguuauuuu cauuuucuug uuccccauau gcccaggcgc   60
auugacuagu acaugaccac uu                                            82

<210> SEQ ID NO 40
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 40
gggaagagaa ggacauauga uaccagcggc guagaaacgu acagcucgcc uguaacgccu   60
guugacuagu acaugaccac uu                                            82

<210> SEQ ID NO 41
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 41
gggaagagaa ggacauauga ucgauauggg ugcgggaaug uacguucacc gaauaugcuc   60
cuugacuagu acaugaccac uu                                            82

<210> SEQ ID NO 42
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 42
gggaagagaa ggacauauga uuaacagugc guagucauau cgaauguuua ucuuccuauu   60
```
uuugacuagu acaugaccac uu                                                    82

<210> SEQ ID NO 43
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 43
gggaagagaa ggacauauga ucagacucuc gcccaauucg caaggcguug cauugcgauu      60
uuugacuagu acaugaccac uu                                                    82

<210> SEQ ID NO 44
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 44
gggaagagaa ggacauauga uuccaacuc uccacgagag caugggucga augacucauu       60
uuugacuagu acaugaccac uu                                                    82

<210> SEQ ID NO 45
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 45
gggaagagaa ggacauauga ugcaucgcgc gucacucaac ucgugauuac cgagggcgcc     60
guugacuagu acaugaccac uu                                                    82

<210> SEQ ID NO 46
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 46
gggaagagaa ggacauauga ucugaaucuu uccgcagccc uguccuuuua aagacagguu    60
uuugacuagu acaugaccac uu                                                    82

<210> SEQ ID NO 47
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 47
gggaagagaa ggacauauga uuuuguuacu uacuucgucu aucuucuguu gcacacaguu     60
uuugacuagu acaugaccac uu                                                    82

<210> SEQ ID NO 48
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 48
gggaagagaa ggacauauga uucaaaucuu cagcgauaau ggcacaauuu ccgcgccauu    60
uuugacuagu acaugaccac uu    82

<210> SEQ ID NO 49
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 49
gggaagagaa ggacauauga uuuaugugag augaugugug uuccuaguuu uaucuugcuc    60
uuugacuagu acaugaccac uu    82

<210> SEQ ID NO 50
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 50
gggaagagaa ggacauauga uccacuuuuc cauuaacugu ugcgggcaag uagcaccguu    60
uuugacuagu acaugaccac uu    82

<210> SEQ ID NO 51
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 51
gggaagagaa ggacauauga uagagaagac cauucggaaa gagcugcgug uccuuaugua    60
cuugacuagu acaugaccac uu    82

<210> SEQ ID NO 52
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 52
gggaagagaa ggacauauga uucuuaugua gcaagcaaaa ugugccgccg agccgacgcc    60
auugacuagu acaugaccac uu    82

<210> SEQ ID NO 53
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 53
gggaagagaa ggacauauga uaagcgcaua auaagccagc caguucuugg cgcgcggggu    60
auugacuagu acaugaccac uu    82

<210> SEQ ID NO 54

```
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 54
gggaagagaa ggacauauga uuaguccgca uuucuauuuu cuauauggcu uacugccauu    60
uuugacuagu acaugaccac uu                                            82

<210> SEQ ID NO 55
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 55
gggaagagaa ggacauauga uauaaagaac acgcaaaacc acccggacac ccggugccgu    60
guugacuagu acaugaccac uu                                            82

<210> SEQ ID NO 56
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 56
gggaagagaa ggacauauga uacacaggcg guggagccga agggcaccgg gacaaaccga    60
cuugacuagu acaugaccac uu                                            82

<210> SEQ ID NO 57
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 57
gggaagagaa ggacauauga uaguuccggc gcagcagcgu ccucacguuu uacgugcccc    60
auugacuagu acaugaccac uu                                            82

<210> SEQ ID NO 58
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 58
gggaagagaa ggacauauga ugaccgucgc gaucguuuau aauguucugg aucuuucauu    60
uuugacuagu acaugaccac uu                                            82

<210> SEQ ID NO 59
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 59
gggaagagaa ggacauauga uaaguggggc cccgacgacu uuccuuccu cucuuccggc     60
```

```
auugacuagu acaugaccac uu                                              82

<210> SEQ ID NO 60
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 60
gggaagagaa ggacauauga uaucaacaua ccaaaauguc auuccaauc uuuucccauu     60 uuugacuagu acaugaccac uu                                              82

<210> SEQ ID NO 61
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 61
gggaagagaa ggacauauga uagcgaacaa acaagggugc ccaggccccc uucgcacauc     60
guugacuagu acaugaccac uu                                              82

<210> SEQ ID NO 62
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 62
gggaagagaa ggacauauga uccucuguaa cgcaaaguca agucgcgcaa ggccgcccgc     60
guugacuagu acaugaccac uu                                              82

<210> SEQ ID NO 63
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 63
gggaagagaa ggacauauga ucuucaucug cgauuacggu acacuuuagu guaucguuuu     60
uuugacuagu acaugaccac uu                                              82

<210> SEQ ID NO 64
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 64
gggaagagaa ggacauauga ugccuaugug cuagaugcag cagcaaccgc cggcgacugg     60
auugacuagu acaugaccac uu                                              82

<210> SEQ ID NO 65
<211> LENGTH: 82
<212> TYPE: RNA
<213> ORGANISM: Artificial Sequence
<220> FEATURE:
```

<223> OTHER INFORMATION: Synthetic aptamer sequence

<400> SEQUENCE: 65
gggaagagaa ggacauauga uccgcgcccu aaccuucuga ccaagcuucc cuggcacuug    60
guugacuagu acaugaccac uu    82

<210> SEQ ID NO 66
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 66
gggaagagaa ggacauauga uccuuaugua uuaucaguca uaccggacgc agcccgcugg    60
auugacuagu acaugaccac uu    82

<210> SEQ ID NO 67
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 67
gggaagagaa ggacauauga ucuaaucuau acuggcugcu aacgcuuuuu cuuuccauu    60 uuugacuagu acaugaccac uu    82

<210> SEQ ID NO 68
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 68
gggaagagaa ggacauauga ucaguuuacg cggagucguu uguguccauu ucuucucauu    60
uuugacuagu acaugaccac uu    82

<210> SEQ ID NO 69
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 69
gggaagagaa ggacauauga uucacgugag augaugugug uuccuaguuu uaucuugcuc    60
uuugacuagu acaugaccac uu    82

<210> SEQ ID NO 70
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 70
gggaagagaa ggacauauga uuccuugugu accgcuccga augugcucca gcgcgccucg    60
guugacuagu acaugaccac uu    82

```
<210> SEQ ID NO 71
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 71
gggaagagaa ggacauauga uaagccggcc cgggaacaug ucacgcgcgc gcgcaaagua    60
guugacuagu acaugaccac uu                                            82

<210> SEQ ID NO 72
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 72
gggaagagaa ggacauauga uccuggauuu ccgaaauuag agugccguuu cguuacgguu    60
uuugacuagu acaugaccac uu                                            82

<210> SEQ ID NO 73
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 73
gggaagagaa ggacauauga ucgugucauc cgcacaagga ggccugcaug gcagggacac    60
guugacuagu acaugaccac uu                                            82

<210> SEQ ID NO 74
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 74
gggaagagaa ggacauauga ugaguagacu uuuguauca uuuuuuuauc guaagauauu     60
uuugacuagu acaugaccac uu                                            82

<210> SEQ ID NO 75
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 75
gggaagagaa ggacauauga uccaugugag augaugugug uuccuaguuu uaucuugcuc    60
uuugacuagu acaugaccac uu                                            82

<210> SEQ ID NO 76
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 76
```
gggaagagaa ggacauauga ucuuugcucu agaguguagu cuaugaggga caagguagcc    60
auugacuagu acaugaccac uu    82

<210> SEQ ID NO 77
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 77
gggaagagaa ggacauauga uguugguuuu cuuucucuuu cuuuucuuuc ucuuucuauu    60
uuugacuagu acaugaccac uu    82

<210> SEQ ID NO 78
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 78
gggaagagaa ggacauauga ucaaucgggc ggggguaaga ggcgugcgca gcguggaggu    60
guugacuagu acaugaccac uu    82

<210> SEQ ID NO 79
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 79
gggaagagaa ggacauauga ucaccguggu gcgcaaagcc gcaacgagaa cugcggaauc    60
guugacuagu acaugaccac uu    82

<210> SEQ ID NO 80
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 80
gggaagagaa ggacauauga uugcuuuaag ucuuuuauc auuuuguuuc cuucauuuuu    60
uuugacuagu acaugaccac uu    82

<210> SEQ ID NO 81
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 81
gggaagagaa ggacauauga ucgacuaguu auacugcaaa ggcuauaagc gcgagcgcgc    60
guugacuagu acaugaccac uu    82

<210> SEQ ID NO 82
<211> LENGTH: 82
<212> TYPE: RNA
<213> ORGANISM: Artificial Sequence

```
<220> FEATURE:
<223> OTHER INFORMATION: Synthetic aptamer sequence

<400> SEQUENCE: 82
gggaagagaa ggacauauga ugaguaauag auggcguaca caaaucggau acgacgagcg      60
cuugacuagu acaugaccac uu                                              82

<210> SEQ ID NO 83
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 83
gggaagagaa ggacauauga uuuucgcuuc aagauuccca acgccuugua agucaagguu      60
uuugacuagu acaugaccac uu                                              82

<210> SEQ ID NO 84
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 84
gggaagagaa ggacauauga ugugugagau gagccccugg accagacgca cgcucgcacu      60
guugacuagu acaugaccac uu                                              82

<210> SEQ ID NO 85
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 85
gggaagagaa ggacauauga ucaggaugcg gcgccgguaa uugacuuccc ccuacguagg      60
auugacuagu acaugaccac uu                                              82

<210> SEQ ID NO 86
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 86
gggaagagaa ggacauauga ucagggaccc ggccggugca ucuccuucuu uagcguacgc      60
cuugacuagu acaugaccac uu                                              82

<210> SEQ ID NO 87
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 87
gggaagagaa ggacauauga ucugcucuaa aguaccaacc gcgggagcua aaugcaagcc      60
guugacuagu acaugaccac uu                                              82
```

```
<210> SEQ ID NO 88
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 88
gggaagagaa ggacauauga ugauugccau gcauuagggg gggacgcgcg cgaaagggag    60
auugacuagu acaugaccac uu                                            82

<210> SEQ ID NO 89
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 89
gggaagagaa ggacauauga uucgcucuaa aguaccaacc gcgggagcua aaugcaagcc    60
guugacuagu acaugaccac uu                                            82

<210> SEQ ID NO 90
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 90
gggaagagaa ggacauauga uaaaaaaccg ggguucuuaa uuuucauugu ucgucguacu    60
uuugacuagu acaugaccac uu                                            82

<210> SEQ ID NO 91
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 91
gggaagagaa ggacauauga uaacccauug gugaaucgca accacagcca gcccggcgcg    60
auugacuagu acaugaccac uu                                            82

<210> SEQ ID NO 92
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 92
gggaagagaa ggacauauga ucgaagugag gggaucgcgc ggggugcacc uaaauauggg    60
auugacuagu acaugaccac uu                                            82

<210> SEQ ID NO 93
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 93
```

-continued gggaagagaa ggacauauga uagccuuaug uacuauagaa gucagcuauc cgccgcacaa    60
uuugacuagu acaugaccac uu    82

<210> SEQ ID NO 94
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 94
gggaagagaa ggacauauga ucguuguuuu ucccaaagcu cguuagcauu cauuccuauu    60
uuugacuagu acaugaccac uu    82

<210> SEQ ID NO 95
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 95
gggaagagaa ggacauauga ugaucaucag cggaaagcac gaaacgccac gggccgcggc    60
auugacuagu acaugaccac uu    82

<210> SEQ ID NO 96
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 96
gggaagagaa ggacauauga uuccuuccua uugacaaugc gcccgggccu cuucaauugu    60
auugacuagu acaugaccac uu    82

<210> SEQ ID NO 97
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 97
gggaagagaa ggacauauga uaguugccgc gcggcgcaag auuggagagu cccgggcugu    60
auugacuagu acaugaccac uu    82

<210> SEQ ID NO 98
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 98
gggaagagaa ggacauauga ucauaaguuc guucauuccg uuaacacgcg uauggcguuu    60
uuugacuagu acaugaccac uu    82

<210> SEQ ID NO 99
<211> LENGTH: 82
<212> TYPE: RNA

```
<213> ORGANISM: Artificial Sequence
<220> FEATURE:
<223> OTHER INFORMATION: Synthetic aptamer sequence

<400> SEQUENCE: 99
gggaagagaa ggacauauga uccuuugucu ccaaaucuua ggacugaaug agugccuauu      60
uuugacuagu acaugaccac uu                                              82

<210> SEQ ID NO 100
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 100
gggaagagaa ggacauauga ucuucuuuga gaauucucuu uuuacaauuc cggcgccgug      60
auugacuagu acaugaccac uu                                              82

<210> SEQ ID NO 101
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 101
gggaagagaa ggacauauga uuaggcuaac uguuuaggga uuugauaugc augaggagca      60
cuugacuagu acaugaccac uu                                              82

<210> SEQ ID NO 102
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 102
gggaagagaa ggacauauga uuaggcuaac uguucaggga guugauaugc augaggagca      60
cuugacuagu acaugaccac uu                                              82

<210> SEQ ID NO 103
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 103
gggaagagaa ggacauauga uuaggcuaac ugcucaggga uuugauaugc augaggagca      60
cuugacuagu acaugaccac uu                                              82

<210> SEQ ID NO 104
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 104
gggaagagaa ggacauauga uuaggcuaac uguucaggga cuugauaugc augaggagca      60
cuugacuagu acaugaccac uu                                              82
```

```
<210> SEQ ID NO 105
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 105
gggaagagaa ggacauauga uuaggcucac uguucaggga uuugauaugc augaggagca    60
cuugacuagu acaugaccac uu                                            82

<210> SEQ ID NO 106
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 106
gggaagagaa ggacauauga uuaggcuaac uguucaggga uuugauaugc augggagca    60 cuugacuagu acaugaccac uu                                            82

<210> SEQ ID NO 107
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 107
gggaagagaa ggacauauga uuucuuccua uugacgaugc gcccgggccu cuucaauugu    60
auugacuagu acaugaccac uu                                            82

<210> SEQ ID NO 108
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 108
gggaagagaa ggacauauga uuaggcuaac uguucgggga uuugauaugc augaggagca    60
cuugacuagu acaugaccac uu                                            82

<210> SEQ ID NO 109
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 109
gggaagagaa ggacauauga uuaggcuaac uguucaggga uuugauaugc acgaggagca    60
cuugacuagu acaugaccac uu                                            82

<210> SEQ ID NO 110
<211> LENGTH: 82
<212> TYPE: RNA
<213> ORGANISM: Artificial Sequence
<220> FEATURE:
<223> OTHER INFORMATION: Synthetic aptamer sequence
```

```
<400> SEQUENCE: 110
gggaagagaa ggacauauga uuagguuaac uguucaggga uuugauaugc augaggagca    60
cuugacuagu acaugaccac uu                                            82

<210> SEQ ID NO 111
<211> LENGTH: 82
<212> TYPE: RNA
<213> ORGANISM: Artificial Sequence
<220> FEATURE:
<223> OTHER INFORMATION: Synthetic aptamer sequence

<400> SEQUENCE: 111
gggaagagaa ggacauauga uuaggcuaac uguucaggga uuugaugugc augaggagca    60
cuugacuagu acaugaccac uu                                            82

<210> SEQ ID NO 112
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 112
gggaagagaa ggacatatga ttcatgtgag atgatgtgtg ttcctagttt tatcttgctc    60
tttgactagt acatgaccac tt                                            82

<210> SEQ ID NO 113
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 113
gggaagagaa ggacatatga ttaggctaac tgttcaggga tttgatatgc atgaggagca    60
cttgactagt acatgaccac tt                                            82

<210> SEQ ID NO 114
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 114
gggaagagaa ggacatatga tccgctctaa agtaccaacc gcgggagcta aatgcaagcc    60
gttgactagt acatgaccac tt                                            82

<210> SEQ ID NO 115
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 115
gggaagagaa ggacatatga ttgtgtcagg ctctagagtc tagacggccg gggtcccgga    60
tttgactagt acatgaccac tt                                            82

<210> SEQ ID NO 116
<211> LENGTH: 82
```

```
<212> TYPE: DNA
<213> ORGANISM: Artificial Sequence
<220> FEATURE:
<223> OTHER INFORMATION: Synthetic aptamer sequence

<400> SEQUENCE: 116
gggaagagaa ggacatatga tccttatgtc tagcggcctt acgcgattag tggcgttttg    60
tttgactagt acatgaccac tt                                             82

<210> SEQ ID NO 117
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 117
gggaagagaa ggacatatga tctttatgta ttatcagtca taccggacgc agcccgctgg    60
attgactagt acatgaccac tt                                             82

<210> SEQ ID NO 118
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 118
gggaagagaa ggacatatga ttgtgttatt acacttcgtg attttccttg cttttctatt    60
tttgactagt acatgaccac tt                                             82

<210> SEQ ID NO 119
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 119
gggaagagaa ggacatatga tccaacatct aaagtactgg tcgcctaggg agactgttcg    60
gttgactagt acatgaccac tt                                             82

<210> SEQ ID NO 120
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 120
gggaagagaa ggacatatga tgctatattc gcaaaagcag gctgagtgcg gcaggcgcgt    60
gttgactagt acatgaccac tt                                             82

<210> SEQ ID NO 121
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 121
gggaagagaa ggacatatga ttcattcatt cgcaacacaa ttgtattcgc atctgcgatt    60
```
tttgactagt acatgaccac tt                                                    82

<210> SEQ ID NO 122
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 122
gggaagagaa ggacatatga tctttctctt ttctaatatt taatttattg ggtaccaatt          60
tttgactagt acatgaccac tt                                                    82

<210> SEQ ID NO 123
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 123
gggaagagaa ggacatatga tctttgtttc gcatacgttt cttttttctc tcttcttatt          60
tttgactagt acatgaccac tt                                                    82

<210> SEQ ID NO 124
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 124
gggaagagaa ggacatatga ttattctgtt cttcaaaaat cttttagcgt atacgctatt          60
tttgactagt acatgaccac tt                                                    82

<210> SEQ ID NO 125
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 125
gggaagagaa ggacatatga tttccttatg ttcggtcaac agggactgct gcagcaccgg          60
cttgactagt acatgaccac tt                                                    82

<210> SEQ ID NO 126
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 126
gggaagagaa ggacatatga ttaagcgcac tcaacagggt ctatgatccg cgccgatcat          60
gttgactagt acatgaccac tt                                                    82

<210> SEQ ID NO 127
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 127
gggaagagaa ggacatatga tccgctttcc attgagatta taagctgtta gagacttatt    60
tttgactagt acatgaccac tt    82

<210> SEQ ID NO 128
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 128
gggaagagaa ggacatatga ttttcgaaac gtttctttca agttcttaat cattcccatt    60
tttgactagt acatgaccac tt    82

<210> SEQ ID NO 129
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 129
gggaagagaa ggacatatga tcattagatg cgcagttcga agccggtaca gctggcgcgc    60
gttgactagt acatgaccac tt    82

<210> SEQ ID NO 130
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 130
gggaagagaa ggacatatga taaagaataa ccttaaaata acaccaccgc ctcacagcat    60
attgactagt acatgaccac tt    82

<210> SEQ ID NO 131
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 131
gggaagagaa ggacatatga taaattgatc tattcttttc ggtgctattt atcttccatt    60
tttgactagt acatgaccac tt    82

<210> SEQ ID NO 132
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 132
gggaagagaa ggacatatga tctactcgcg cggcggacaa aagcgcaacc cagcacccat    60
gttgactagt acatgaccac tt    82

<210> SEQ ID NO 133

<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 133
gggaagagaa ggacatatga ttcttagttt gtaattactt ttccttcctt ttattctatt     60
tttgactagt acatgaccac tt                                              82

<210> SEQ ID NO 134
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 134
gggaagagaa ggacatatga taacccgcgc agacttacaa gcgcgcaaaa aaagggtacg     60
tttgactagt acatgaccac tt                                              82

<210> SEQ ID NO 135
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 135
gggaagagaa ggacatatga tattccttta tgccgcatca ttttattgtt tatgacaatt     60
tttgactagt acatgaccac tt                                              82

<210> SEQ ID NO 136
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 136
gggaagagaa ggacatatga tatttcgtac tactttttctt ccaagcttca atcgcccatt    60
tttgactagt acatgaccac tt                                              82

<210> SEQ ID NO 137
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 137
gggaagagaa ggacatatga ttcactcatt cgcaacacaa ttgtattcgc atctgcgatt     60
tttgactagt acatgaccac tt                                              82

<210> SEQ ID NO 138
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 138
gggaagagaa ggacatatga tattatttcc acagttcctt tatccacaca tcttctcatt     60

```
tttgactagt acatgaccac tt                                              82

<210> SEQ ID NO 139
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 139
gggaagagaa ggacatatga taaactcgtt atctattcgt ttatttgcat ctctttcatt    60
tttgactagt acatgaccac tt                                              82

<210> SEQ ID NO 140
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 140
gggaagagaa ggacatatga tccaacctct aaagtactgg tcgcctaggg agactgttcg    60
gttgactagt acatgaccac tt                                              82

<210> SEQ ID NO 141
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 141
gggaagagaa ggacatatga tttccttttt gctatttccg ttaatgtaaa ctctcctatt    60
tttgactagt acatgaccac tt                                              82

<210> SEQ ID NO 142
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 142
gggaagagaa ggacatatga tccttatggc ctagtaggga tccgggcgcc gaccagcgcg    60
attgactagt acatgaccac tt                                              82

<210> SEQ ID NO 143
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 143
gggaagagaa ggacatatga tcgtctgtct tcttcgaata cgttttgggc taagcccatt    60
tttgactagt acatgaccac tt                                              82

<210> SEQ ID NO 144
<211> LENGTH: 82
<212> TYPE: DNA
<213> ORGANISM: Artificial Sequence
<220> FEATURE:
```

<223> OTHER INFORMATION: Synthetic aptamer sequence

<400> SEQUENCE: 144
gggaagagaa ggacatatga ttcaaccaaa ctgccgacga ccgaggtatg tccttatgta    60
cttgactagt acatgaccac tt    82

<210> SEQ ID NO 145
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 145
gggaagagaa ggacatatga ttacgggtct gagcaaaagc gaaggaagca ggcgcaggga    60
tttgactagt acatgaccac tt    82

<210> SEQ ID NO 146
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 146
gggaagagaa ggacatatga ttctctcatt cgcaacacaa ttgtattcgc atctgcgatt    60
tttgactagt acatgaccac tt    82

<210> SEQ ID NO 147
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 147
gggaagagaa ggacatatga tgctctaaag tactaagcgt ttgcgccgat gcccggaccg    60
cttgactagt acatgaccac tt    82

<210> SEQ ID NO 148
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 148
gggaagagaa ggacatatga tacttcatta atgtgaggcc gtcaggggc aaccttcgag    60 cttgactagt acatgaccac tt    82

<210> SEQ ID NO 149
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 149
gggaagagaa ggacatatga ttccttattc ttgttactac tttcttttcc tatttttttc    60
tttgactagt acatgaccac tt    82

```
<210> SEQ ID NO 150
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 150
gggaagagaa ggacatatga tcgttatttt cattttcttg ttccccatat gcccaggcgc    60
attgactagt acatgaccac tt                                             82

<210> SEQ ID NO 151
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 151
gggaagagaa ggacatatga taccagcggc gtagaaacgt acagctcgcc tgtaacgcct    60
gttgactagt acatgaccac tt                                             82

<210> SEQ ID NO 152
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 152
gggaagagaa ggacatatga tcgatatggg tgcgggaatg tacgttcacc gaatatgctc    60
cttgactagt acatgaccac tt                                             82

<210> SEQ ID NO 153
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 153
gggaagagaa ggacatatga ttaacagtgc gtagtcatat cgaatgttta tcttcctatt    60
tttgactagt acatgaccac tt                                             82

<210> SEQ ID NO 154
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 154
gggaagagaa ggacatatga tcagactctc gcccaattcg caaggcgttg cattgcgatt    60
tttgactagt acatgaccac tt                                             82

<210> SEQ ID NO 155
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 155
```

```
gggaagagaa ggacatatga tttccaactc tccacgagag catgggtcga atgactcatt    60
tttgactagt acatgaccac tt                                            82
```

<210> SEQ ID NO 156
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 156

```
gggaagagaa ggacatatga tgcatcgcgc gtcactcaac tcgtgattac cgagggcgcc    60
gttgactagt acatgaccac tt                                            82
```

<210> SEQ ID NO 157
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 157

```
gggaagagaa ggacatatga tctgaatctt tccgcagccc tgtccttttta aagacaggtt   60 tttgactagt acatgaccac tt                                            82
```

<210> SEQ ID NO 158
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 158

```
gggaagagaa ggacatatga ttttgttact tacttcgtct atcttctgtt gcacacagtt    60
tttgactagt acatgaccac tt                                            82
```

<210> SEQ ID NO 159
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 159

```
gggaagagaa ggacatatga ttcaaatctt cagcgataat ggcacaattt ccgcgccatt    60
tttgactagt acatgaccac tt                                            82
```

<210> SEQ ID NO 160
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 160

```
gggaagagaa ggacatatga tttatgtgag atgatgtgtg ttcctagttt tatcttgctc    60
tttgactagt acatgaccac tt                                            82
```

<210> SEQ ID NO 161
<211> LENGTH: 82
<212> TYPE: DNA
<213> ORGANISM: Artificial Sequence

```
<220> FEATURE:
<223> OTHER INFORMATION: Synthetic aptamer sequence

<400> SEQUENCE: 161
gggaagagaa ggacatatga tccactttc cattaactgt tgcgggcaag tagcaccgtt      60
tttgactagt acatgaccac tt                                              82

<210> SEQ ID NO 162
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 162
gggaagagaa ggacatatga tagagaagac cattcggaaa gagctgcgtg tccttatgta    60
cttgactagt acatgaccac tt                                              82

<210> SEQ ID NO 163
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 163
gggaagagaa ggacatatga ttcttatgta gcaagcaaaa tgtgccgccg agccgacgcc    60
attgactagt acatgaccac tt                                              82

<210> SEQ ID NO 164
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 164
gggaagagaa ggacatatga taagcgcata ataagccagc cagttcttgg cgcgcggggt    60
attgactagt acatgaccac tt                                              82

<210> SEQ ID NO 165
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 165
gggaagagaa ggacatatga ttagtccgca tttctatttt ctatatggct tactgccatt    60
tttgactagt acatgaccac tt                                              82

<210> SEQ ID NO 166
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 166
gggaagagaa ggacatatga tataaagaac acgcaaaacc acccggacac ccggtgccgt    60
gttgactagt acatgaccac tt                                              82
```

<210> SEQ ID NO 167
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 167
gggaagagaa ggacatatga tacacaggcg gtggagccga agggcaccgg gacaaaccga    60
cttgactagt acatgaccac tt                                             82

<210> SEQ ID NO 168
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 168
gggaagagaa ggacatatga tagttccggc gcagcagcgt cctcacgttt tacgtgcccc    60
attgactagt acatgaccac tt                                             82

<210> SEQ ID NO 169
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 169
gggaagagaa ggacatatga tgaccgtcgc gatcgtttat aatgttctgg atctttcatt    60
tttgactagt acatgaccac tt                                             82

<210> SEQ ID NO 170
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 170
gggaagagaa ggacatatga taagtggggc cccgacgact tttccttcct ctcttccggc    60
attgactagt acatgaccac tt                                             82

<210> SEQ ID NO 171
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 171
gggaagagaa ggacatatga tatcaacata ccaaaatgtc atttccaatc ttttcccatt    60
tttgactagt acatgaccac tt                                             82

<210> SEQ ID NO 172
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 172

```
gggaagagaa ggacatatga tagcgaacaa acaagggtgc ccaggccccc ttcgcacatc    60
gttgactagt acatgaccac tt                                            82

<210> SEQ ID NO 173
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 173
gggaagagaa ggacatatga tcctctgtaa cgcaaagtca agtcgcgcaa ggccgcccgc    60
gttgactagt acatgaccac tt                                            82

<210> SEQ ID NO 174
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 174
gggaagagaa ggacatatga tcttcatctg cgattacggt acactttagt gtatcgtttt    60
tttgactagt acatgaccac tt                                            82

<210> SEQ ID NO 175
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 175
gggaagagaa ggacatatga tgcctatgtg ctagatgcag cagcaaccgc cggcgactgg    60
attgactagt acatgaccac tt                                            82

<210> SEQ ID NO 176
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 176
gggaagagaa ggacatatga tccgcgccct aaccttctga ccaagcttcc ctggcacttg    60
gttgactagt acatgaccac tt                                            82

<210> SEQ ID NO 177
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 177
gggaagagaa ggacatatga tccttatgta ttatcagtca taccggacgc agcccgctgg    60
attgactagt acatgaccac tt                                            82

<210> SEQ ID NO 178
<211> LENGTH: 82
<212> TYPE: DNA
```

<213> ORGANISM: Artificial Sequence
<220> FEATURE:
<223> OTHER INFORMATION: Synthetic aptamer sequence

<400> SEQUENCE: 178
gggaagagaa ggacatatga tctaatctat actggctgct aacgcttttt cttttccatt    60
tttgactagt acatgaccac tt                                             82

<210> SEQ ID NO 179
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 179
gggaagagaa ggacatatga tcagtttacg cggagtcgtt tgtgtccatt tcttctcatt    60
tttgactagt acatgaccac tt                                             82

<210> SEQ ID NO 180
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 180
gggaagagaa ggacatatga ttcacgtgag atgatgtgtg ttcctagttt tatcttgctc    60
tttgactagt acatgaccac tt                                             82

<210> SEQ ID NO 181
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 181
gggaagagaa ggacatatga ttccttgtgt accgctccga atgtgctcca gcgcgcctcg    60
gttgactagt acatgaccac tt                                             82

<210> SEQ ID NO 182
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 182
gggaagagaa ggacatatga taagccggcc cgggaacatg tcacgcgcgc gcgcaaagta    60
gttgactagt acatgaccac tt                                             82

<210> SEQ ID NO 183
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 183
gggaagagaa ggacatatga tcctggattt ccgaaattag agtgccgttt cgttacggtt    60
tttgactagt acatgaccac tt                                             82

<210> SEQ ID NO 184
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 184
gggaagagaa ggacatatga tcgtgtcatc cgcacaagga ggcctgcatg gcagggacac    60
gttgactagt acatgaccac tt                                            82

<210> SEQ ID NO 185
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 185
gggaagagaa ggacatatga tgagtagact ttttgtatca tttttttatc gtaagatatt    60
tttgactagt acatgaccac tt                                            82

<210> SEQ ID NO 186
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 186
gggaagagaa ggacatatga tccatgtgag atgatgtgtg ttcctagttt tatcttgctc    60
tttgactagt acatgaccac tt                                            82

<210> SEQ ID NO 187
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 187
gggaagagaa ggacatatga tctttgctct agagtgtagt ctatgaggga caaggtagcc    60
attgactagt acatgaccac tt                                            82

<210> SEQ ID NO 188
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 188
gggaagagaa ggacatatga tgttggtttt ctttctcttt cttttctttc tctttctatt    60
tttgactagt acatgaccac tt                                            82

<210> SEQ ID NO 189
<211> LENGTH: 82
<212> TYPE: DNA
<213> ORGANISM: Artificial Sequence
<220> FEATURE:
<223> OTHER INFORMATION: Synthetic aptamer sequence

```
<400> SEQUENCE: 189
gggaagagaa ggacatatga tcaatcgggc gggggtaaga ggcgtgcgca gcgtggaggt    60
gttgactagt acatgaccac tt                                             82

<210> SEQ ID NO 190
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 190
gggaagagaa ggacatatga tcaccgtggt gcgcaaagcc gcaacgagaa ctgcggaatc    60
gttgactagt acatgaccac tt                                             82

<210> SEQ ID NO 191
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 191
gggaagagaa ggacatatga ttgctttaag tctttttatc attttgtttc cttcattttt    60
tttgactagt acatgaccac tt                                             82

<210> SEQ ID NO 192
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 192
gggaagagaa ggacatatga tcgactagtt atactgcaaa ggctataagc gcgagcgcgc    60
gttgactagt acatgaccac tt                                             82

<210> SEQ ID NO 193
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 193
gggaagagaa ggacatatga tgagtaatag atggcgtaca caaatcggat acgacgagcg    60
cttgactagt acatgaccac tt                                             82

<210> SEQ ID NO 194
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 194
gggaagagaa ggacatatga ttttcgcttc aagattccca acgccttgta agtcaaggtt    60
tttgactagt acatgaccac tt                                             82

<210> SEQ ID NO 195
<211> LENGTH: 82
```

```
<212> TYPE: DNA
<213> ORGANISM: Artificial Sequence
<220> FEATURE:
<223> OTHER INFORMATION: Synthetic aptamer sequence

<400> SEQUENCE: 195
gggaagagaa ggacatatga tgtgtgagat gagcccctgg accagacgca cgctcgcact    60
gttgactagt acatgaccac tt                                             82

<210> SEQ ID NO 196
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 196
gggaagagaa ggacatatga tcaggatgcg gcgccggtaa ttgacttccc cctacgtagg    60
attgactagt acatgaccac tt                                             82

<210> SEQ ID NO 197
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 197
gggaagagaa ggacatatga tcagggaccc ggccggtgca tctccttctt tagcgtacgc    60
cttgactagt acatgaccac tt                                             82

<210> SEQ ID NO 198
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 198
gggaagagaa ggacatatga tctgctctaa agtaccaacc gcgggagcta aatgcaagcc    60
gttgactagt acatgaccac tt                                             82

<210> SEQ ID NO 199
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 199
gggaagagaa ggacatatga tgattgccat gcattagggg gggacgcgcg cgaaagggag    60
attgactagt acatgaccac tt                                             82

<210> SEQ ID NO 200
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 200
gggaagagaa ggacatatga ttcgctctaa agtaccaacc gcgggagcta aatgcaagcc    60
```

```
gttgactagt acatgaccac tt                                              82
```

<210> SEQ ID NO 201
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 201

```
gggaagagaa ggacatatga taaaaaaccg gggttcttaa ttttcattgt tcgtcgtact     60
tttgactagt acatgaccac tt                                              82
```

<210> SEQ ID NO 202
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 202

```
gggaagagaa ggacatatga taacccattg gtgaatcgca accacagcca gcccggcgcg     60
attgactagt acatgaccac tt                                              82
```

<210> SEQ ID NO 203
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 203

```
gggaagagaa ggacatatga tcgaagtgag gggatcgcgc ggggtgcacc taaatatggg     60
attgactagt acatgaccac tt                                              82
```

<210> SEQ ID NO 204
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 204

```
gggaagagaa ggacatatga tagccttatg tactatagaa gtcagctatc cgccgcacaa     60
tttgactagt acatgaccac tt                                              82
```

<210> SEQ ID NO 205
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 205

```
gggaagagaa ggacatatga tcgttgtttt tcccaaagct cgttagcatt cattcctatt     60
tttgactagt acatgaccac tt                                              82
```

<210> SEQ ID NO 206
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 206
gggaagagaa ggacatatga tgatcatcag cggaaagcac gaaacgccac gggccgcggc    60
attgactagt acatgaccac tt    82

<210> SEQ ID NO 207
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 207
gggaagagaa ggacatatga ttccttccta ttgacaatgc gcccgggcct cttcaattgt    60
attgactagt acatgaccac tt    82

<210> SEQ ID NO 208
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 208
gggaagagaa ggacatatga tagttgccgc gcggcgcaag attggagagt cccgggctgt    60
attgactagt acatgaccac tt    82

<210> SEQ ID NO 209
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 209
gggaagagaa ggacatatga tcataagttc gttcattccg ttaacacgcg tatggcgttt    60
tttgactagt acatgaccac tt    82

<210> SEQ ID NO 210
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 210
gggaagagaa ggacatatga tcctttgtct ccaaatctta ggactgaatg agtgcctatt    60
tttgactagt acatgaccac tt    82

<210> SEQ ID NO 211
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 211
gggaagagaa ggacatatga tcttctttga gaattctctt tttacaattc cggcgccgtg    60
attgactagt acatgaccac tt    82

<210> SEQ ID NO 212

```
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 212
gggaagagaa ggacatatga ttaggctaac tgtttaggga tttgatatgc atgaggagca    60
cttgactagt acatgaccac tt                                             82

<210> SEQ ID NO 213
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 213
gggaagagaa ggacatatga tcgtctgtct tcttcgaata cgttttgggc taagcccatt    60
tttgactagt acatgaccac tt                                             82

<210> SEQ ID NO 214
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 214
gggaagagaa ggacatatga ttaggctaac tgctcaggga tttgatatgc atgaggagca    60
cttgactagt acatgaccac tt                                             82

<210> SEQ ID NO 215
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 215
gggaagagaa ggacatatga ttaggctaac tgttcaggga cttgatatgc atgaggagca    60
cttgactagt acatgaccac tt                                             82

<210> SEQ ID NO 216
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 216
gggaagagaa ggacatatga ttaggctcac tgttcaggga tttgatatgc atgaggagca    60
cttgactagt acatgaccac tt                                             82

<210> SEQ ID NO 217
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 217
gggaagagaa ggacatatga ttaggctaac tgttcaggga tttgatatgc atggggagca    60
```

```
cttgactagt acatgaccac tt                                                82

<210> SEQ ID NO 218
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 218
gggaagagaa ggacatatga tttcttccta ttgacgatgc gcccgggcct cttcaattgt       60
attgactagt acatgaccac tt                                                82

<210> SEQ ID NO 219
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 219
gggaagagaa ggacatatga ttaggctaac tgttcgggga tttgatatgc atgaggagca       60
cttgactagt acatgaccac tt                                                82

<210> SEQ ID NO 220
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 220
gggaagagaa ggacatatga ttaggctaac tgttcaggga tttgatatgc acgaggagca       60
cttgactagt acatgaccac tt                                                82

<210> SEQ ID NO 221
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 221
gggaagagaa ggacatatga ttaggttaac tgttcaggga tttgatatgc atgaggagca       60
cttgactagt acatgaccac tt                                                82

<210> SEQ ID NO 222
<211> LENGTH: 82
<212> TYPE: DNA
<213> ORGANISM: Artificial Sequence
<220> FEATURE:
<223> OTHER INFORMATION: Synthetic aptamer sequence

<400> SEQUENCE: 222
gggaagagaa ggacatatga ttaggctaac tgttcaggga tttgatgtgc atgaggagca       60
cttgactagt acatgaccac tt                                                82

<210> SEQ ID NO 223
<211> LENGTH: 21
<212> TYPE: DNA
<213> ORGANISM: Artificial Sequence
<220> FEATURE:
```

```
<223> OTHER INFORMATION: T7 Promoter Sequence

<400> SEQUENCE: 223
gggaagagaa ggacatatga t                                              21

<210> SEQ ID NO 224
<211> LENGTH: 21
<212> TYPE: DNA
<213> ORGANISM: Artificial Sequence
<220> FEATURE:
<223> OTHER INFORMATION: Reverse Primer Recognition Sequence

<400> SEQUENCE: 224
ttgactagta catgaccact t                                              21
```